(12) United States Patent
Abo et al.

(10) Patent No.: US 8,536,310 B2
(45) Date of Patent: Sep. 17, 2013

(54) ANTIBODIES TO CLL-1

(75) Inventors: Arie Abo, Oakland, CA (US); Wouter Korver, Menlo Park, CA (US)

(73) Assignee: Arca Biopharma, Inc., Broomfield, CO (US)

( * ) Notice: Subject to any disclaimer, the term of this patent is extended or adjusted under 35 U.S.C. 154(b) by 112 days.

(21) Appl. No.: 12/738,546

(22) PCT Filed: Oct. 3, 2008

(86) PCT No.: PCT/US2008/078702
§ 371 (c)(1),
(2), (4) Date: Jul. 12, 2010

(87) PCT Pub. No.: WO2009/051974
PCT Pub. Date: Apr. 23, 2009

(65) Prior Publication Data
US 2010/0285037 A1      Nov. 11, 2010

Related U.S. Application Data

(60) Provisional application No. 60/980,567, filed on Oct. 17, 2007.

(51) Int. Cl.
*C12P 21/08*      (2006.01)
(52) U.S. Cl.
USPC ..................................................... 530/387.3
(58) Field of Classification Search
None
See application file for complete search history.

(56) References Cited

U.S. PATENT DOCUMENTS

| | | | |
|---|---|---|---|
| 2006/0177451 A1 | 8/2006 | Van den Oudenrijn | 424/155.1 |
| 2007/0141025 A1 | 6/2007 | Epstein et al. | 424/85.1 |
| 2009/0181009 A1 | 7/2009 | Abo et al. | 424/130.1 |

FOREIGN PATENT DOCUMENTS

| WO | WO 00/44788 | 8/2000 |
|---|---|---|
| WO | WO 2004/056312 | 8/2004 |
| WO | WO 2008/047723 | 4/2008 |
| WO | WO 2009/051957 | 4/2009 |
| WO | WO 2009/064944 | 5/2009 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
[Fundamental Immunology p. 242 (William E. Paul, M.D. ed., 3d ed; 1993)].*
Bakker et al., "C-Type Lectin-Like Molecule-1: A Novel Myeloid Cell Surface Marker Associated with Acute Myeloid Leukemia," *Cancer Res.*, 64:8443-8450, 2004.
Canziani et al., "Kinetic screening of antibodies from crude hybridoma samples using Biacore," *Anal. Biochem.*, 325:301-307, 2004.
Marshall et al., "Identification and Characterization of a Novel Human Myeloid Inhibitory C-type Lectin-like Receptor (MICL) That Is Predominantly Expressed on Granulocytes and Monocytes," *J. Biol. Chem.*, 279:14792-14802, 2004.
Ravtek and Lanier, "Immune Inhibitory Receptors," *Science*, 290:84-89, 2000.
Schultz et al., "Severe defects in immunity and hematopoiesis caused by SHP-1 protein-tyrosine-phosphatase deficiency," *Trends Biotechnol.*, 15:302-307, 1997.
Supplementary European Search Report issued in European Application No. EP 08 84 0487, dated Jun. 9, 2011.
Van Rhenen et al., "The novel AML stem cell associated antigen CLL-1 aids in discrimation between normal and leukemic stem cells," *Blood*, 110(7):2659-2666, 2007.

* cited by examiner

*Primary Examiner* — Brad Duffy
(74) *Attorney, Agent, or Firm* — Fulbright & Jaworski LLP

(57) ABSTRACT

Anti-CLL-1 antibodies and antigen-binding fragments thereof, as well as pharmaceutical compositions comprising such antibodies and antigen-binding fragments are described. Also described are methods of using such antibodies and antigen-binding regions to bind CLL-1 and treat diseases, such as hematologic malignancies, which are characterized by expression of CLL-1.

10 Claims, 10 Drawing Sheets

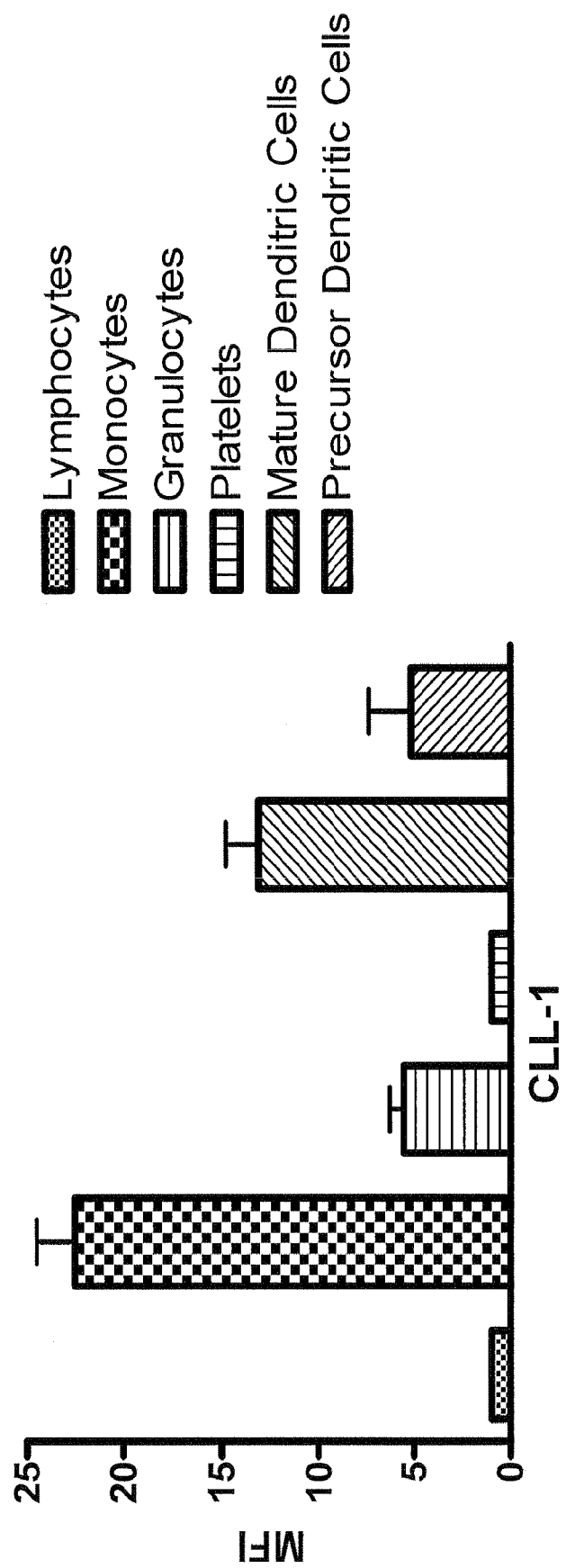

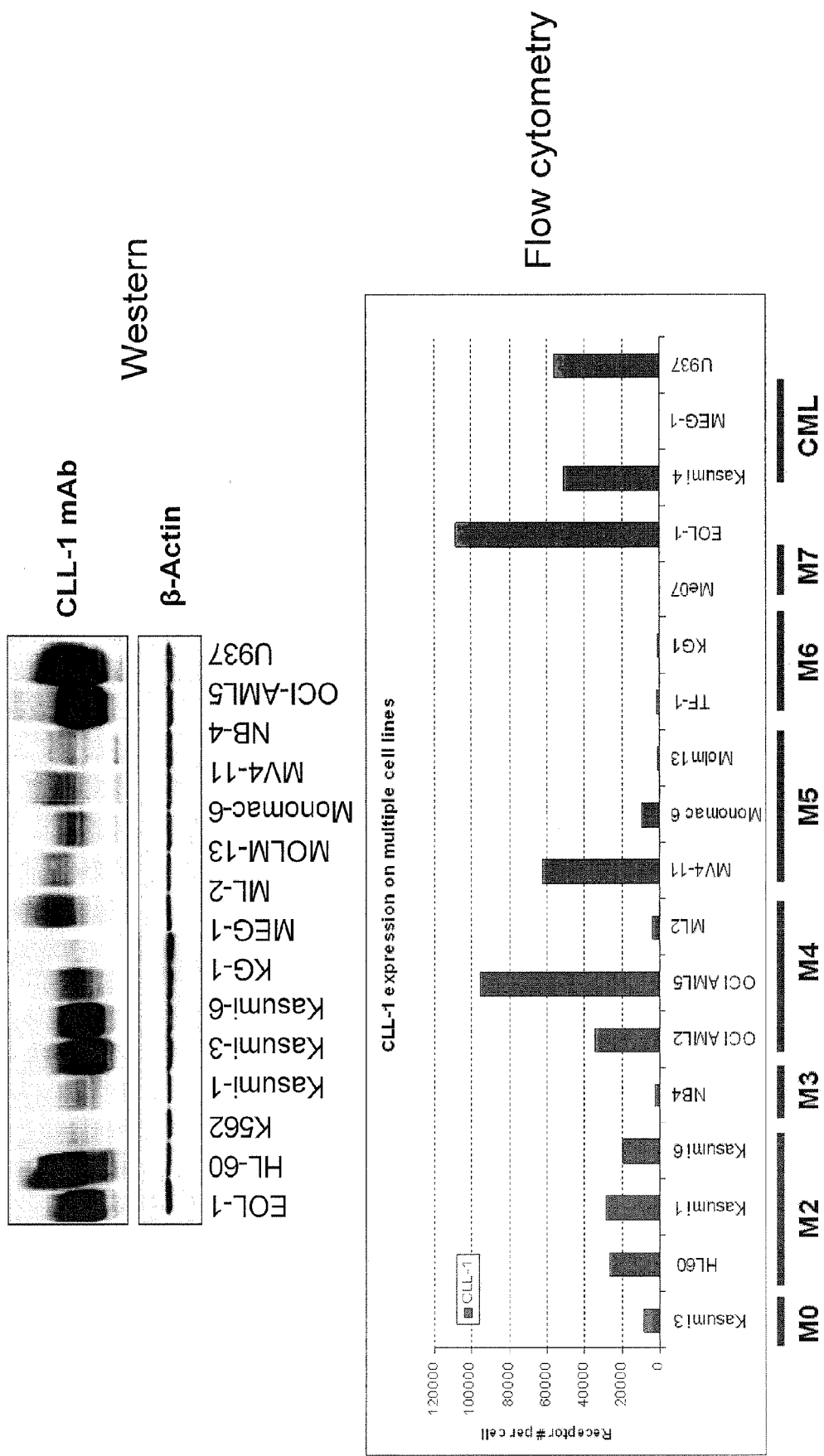

SEQUENCE LISTING

<160> NUMBER OF SEQ ID NOS: 36

<210> SEQ ID NO 1
<211> LENGTH: 1613
<212> TYPE: DNA
<213> ORGANISM: Homo sapiens
<220> FEATURE:
<221> NAME/KEY: CDS

<222> LOCATION: (183)..(980)

<400> SEQUENCE: 1

| | | |
|---|---|---|
| tttgcagaca tatgggtgat tggtacagta ggtttataaa cagaagttta aacttgtaag | 60 |
| cttaagcttc cgtttataaa cagaagttta aaattatagg tcctgtttaa cattcagctc | 120 |
| tgttaactca ctcatctttt tgtgttttta cactttgtca agatttcttt acatattcat | 180 |

| ca atg tct gaa gaa gtt act tat gca gat ctt caa ttc cag aac tcc | 227 |
|---|---|
|    Met Ser Glu Glu Val Thr Tyr Ala Asp Leu Gln Phe Gln Asn Ser | |
|     1             5              10             15 | |

| agt gag atg gaa aaa atc cca gaa att ggc aaa ttt ggg gaa aaa gca | 275 |
|---|---|
| Ser Glu Met Glu Lys Ile Pro Glu Ile Gly Lys Phe Gly Glu Lys Ala | |
|               20              25             30 | |

| cct cca gct ccc tct cat gta tgg cgt cca gca gcc ttg ttt ctg act | 323 |
|---|---|
| Pro Pro Ala Pro Ser His Val Trp Arg Pro Ala Ala Leu Phe Leu Thr | |
|          35               40              45 | |

| ctt ctg tgc ctt ctg ttg ctc att gga ttg gga gtc ttg gca agc atg | 371 |
|---|---|
| Leu Leu Cys Leu Leu Leu Leu Ile Gly Leu Gly Val Leu Ala Ser Met | |
|        50               55              60 | |

| ttt cac gta act ttg aag ata gaa atg aaa aaa atg aac aaa cta caa | 419 |
|---|---|
| Phe His Val Thr Leu Lys Ile Glu Met Lys Lys Met Asn Lys Leu Gln | |
|   65                70             75 | |

| aac atc agt gaa gag ctc cag aga aat att tct cta caa ctg atg agt | 467 |
|---|---|
| Asn Ile Ser Glu Glu Leu Gln Arg Asn Ile Ser Leu Gln Leu Met Ser | |
| 80              85              90             95 | |

| aac atg aat atc tcc aac aag atc agg aac ctc tcc acc aca ctg caa | 515 |
|---|---|
| Asn Met Asn Ile Ser Asn Lys Ile Arg Asn Leu Ser Thr Thr Leu Gln | |
|               100            105            110 | |

| aca ata gcc acc aaa tta tgt cgt gag cta tat agc aaa gaa caa gag | 563 |
|---|---|
| Thr Ile Ala Thr Lys Leu Cys Arg Glu Leu Tyr Ser Lys Glu Gln Glu | |
|          115             120            125 | |

| cac aaa tgt aag cct tgt cca agg aga tgg att tgg cat aag gac agc | 611 |
|---|---|
| His Lys Cys Lys Pro Cys Pro Arg Arg Trp Ile Trp His Lys Asp Ser | |
|      130             135            140 | |

| tgt tat ttc cta agt gat gat gtc caa aca tgg cag gag agt aaa atg | 659 |
|---|---|
| Cys Tyr Phe Leu Ser Asp Asp Val Gln Thr Trp Gln Glu Ser Lys Met | |
|  145               150            155 | |

| gcc tgt gct gct cag aat gcc agc ctg ttg aag ata aac aac aaa aat | 707 |
|---|---|
| Ala Cys Ala Ala Gln Asn Ala Ser Leu Leu Lys Ile Asn Asn Lys Asn | |
| 160              165            170            175 | |

| gca ttg gaa ttt ata aaa tcc cag agt aga tca tat gac tat tgg ctg | 755 |
|---|---|
| Ala Leu Glu Phe Ile Lys Ser Gln Ser Arg Ser Tyr Asp Tyr Trp Leu | |
|               180            185           190 | |

| gga tta tct cct gaa gaa gat tcc act cgt ggt atg aga gtg gat aat | 803 |
|---|---|
| Gly Leu Ser Pro Glu Glu Asp Ser Thr Arg Gly Met Arg Val Asp Asn | |
|          195             200            205 | |

| ata atc aac tcc tct gcc tgg gtt ata aga aac gca cct gac tta aat | 851 |
|---|---|
| Ile Ile Asn Ser Ser Ala Trp Val Ile Arg Asn Ala Pro Asp Leu Asn | |
|               210            215           220 | |

| aac atg tat tgt gga tat ata aat aga cta tat gtt caa tat tat cac | 899 |
|---|---|
| Asn Met Tyr Cys Gly Tyr Ile Asn Arg Leu Tyr Val Gln Tyr Tyr His | |
|      225             230            235 | |

| tgc act tat aaa aaa aga atg ata tgt gag aag atg gcc aat cca gtg | 947 |
|---|---|
| Cys Thr Tyr Lys Lys Arg Met Ile Cys Glu Lys Met Ala Asn Pro Val | |
| 240              245            250            255 | |

| cag ctt ggt tct aca tat ttt agg gag gca tga ggcatcaatc aaatacattt | 1000 |
|---|---|
| Gln Leu Gly Ser Thr Tyr Phe Arg Glu Ala | |
|          260             265 | |

| aaggagtgta gggggtgggg gttctaggct ataggtaaat ttaaatattt tctggttgac | 1060 |
|---|---|

```
aattagttga gtttgtctga agacctggga ttttatcatg cagatgaaac atccaggtag    1120
caagcttcag agagaataga ctgtgaatgt taatgccaga gaggtataat gaagcatgtc    1180
ccacctccca ctttccatca tggcctgaac cctggaggaa gaggaagtcc attcagatag    1240
ttgtgggggg cctccgaatt ttcatttca tttacgttct tccccttctg gccaagattt    1300
gccagaggca acatcaaaaa ccagcaaatt taattttgt cccacagcgt tgctagggtg    1360
gcatggctcc ccatctcggg tccatcctat acttccatgg gactccctat ggctgaaggc    1420
cttatgagtc aaaggactta tagccaattg attgttctag gccaggtaag aatggatatg    1480
gacatgcatt tattacctct taaaattatt attttaagta aaagccaata aacaaaaacg    1540
aaaaggcaaa aaaaaaaaaa aaaaaaaaaa aaaaaaaaaa aaaaaaaaaa aaaaaaaaaa    1600
aaaaaaaaaa aaa                                                      1613

<210> SEQ ID NO 2
<211> LENGTH: 265
<212> TYPE: PRT
<213> ORGANISM: Homo sapiens

<400> SEQUENCE: 2

Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
    130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
    210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
            260                 265
```

```
<210> SEQ ID NO 3
<211> LENGTH: 199
<212> TYPE: PRT
<213> ORGANISM: Homo sapiens

<400> SEQUENCE: 3

Thr Leu Lys Ile Glu Met Lys Lys Met Asn Lys Leu Gln Asn Ile Ser
1               5                   10                  15

Glu Glu Leu Gln Arg Asn Ile Ser Leu Gln Leu Met Ser Asn Met Asn
            20                  25                  30

Ile Ser Asn Lys Ile Arg Asn Leu Ser Thr Thr Leu Gln Thr Ile Ala
        35                  40                  45

Thr Lys Leu Cys Arg Glu Leu Tyr Ser Lys Glu Gln Glu His Lys Cys
    50                  55                  60

Lys Pro Cys Pro Arg Arg Trp Ile Trp His Lys Asp Ser Cys Tyr Phe
65                  70                  75                  80

Leu Ser Asp Asp Val Gln Thr Trp Gln Glu Ser Lys Met Ala Cys Ala
                85                  90                  95

Ala Gln Asn Ala Ser Leu Leu Lys Ile Asn Asn Lys Asn Ala Leu Glu
            100                 105                 110

Phe Ile Lys Ser Gln Ser Arg Ser Tyr Asp Tyr Trp Leu Gly Leu Ser
        115                 120                 125

Pro Glu Glu Asp Ser Thr Arg Gly Met Arg Val Asp Asn Ile Ile Asn
    130                 135                 140

Ser Ser Ala Trp Val Ile Arg Asn Ala Pro Asp Leu Asn Asn Met Tyr
145                 150                 155                 160

Cys Gly Tyr Ile Asn Arg Leu Tyr Val Gln Tyr Tyr His Cys Thr Tyr
                165                 170                 175

Lys Lys Arg Met Ile Cys Glu Lys Met Ala Asn Pro Val Gln Leu Gly
            180                 185                 190

Ser Thr Tyr Phe Arg Glu Ala
        195

<210> SEQ ID NO 4
<211> LENGTH: 363
<212> TYPE: DNA
<213> ORGANISM: Mus musculus

<400> SEQUENCE: 4
caggtccaac tgcagcagcc tggggctgaa ctggtaaagc ctgggacttc agtgaagttg      60
tcctgcaagg cttctggcta cactttcacc aggtactgga tgcactgggt gaagcagagg     120
cctggacaag gccttgagtg gattggaatg attcatccta gtagtggtag tactagctac     180
aatgagaagt tcaagaacaa ggccacactg actgtagaca gatcctccac cacagcctac     240
atgcaactca gcagcctgac atctgaggac tctgcggtct attactgtgc aagagacggg     300
gattattact atggtactgg ggactactgg ggccaaggca ccactctcac agtctcctca     360
gcc                                                                   363

<210> SEQ ID NO 5
<211> LENGTH: 473
<212> TYPE: PRT
<213> ORGANISM: Mus musculus

<400> SEQUENCE: 5

Met Glu Thr Asp Thr Leu Leu Leu Trp Val Leu Leu Leu Trp Val Pro
1               5                   10                  15

Gly Ser Thr Gly Asp Ala Ser Gln Val Gln Leu Gln Gln Pro Gly Ala
```

-continued

```
                20                  25                  30
Glu Leu Val Lys Pro Gly Thr Ser Val Lys Leu Ser Cys Lys Ala Ser
            35                  40                  45
Gly Tyr Thr Phe Thr Arg Tyr Trp Met His Trp Val Lys Gln Arg Pro
        50                  55                  60
Gly Gln Gly Leu Glu Trp Ile Gly Met Ile His Pro Ser Ser Gly Ser
65                  70                  75                  80
Thr Ser Tyr Asn Glu Lys Val Lys Asn Lys Ala Thr Leu Thr Val Asp
                85                  90                  95
Arg Ser Ser Thr Thr Ala Tyr Met Gln Leu Ser Ser Leu Thr Ser Glu
            100                 105                 110
Asp Ser Ala Val Tyr Tyr Cys Ala Arg Asp Gly Asp Tyr Tyr Tyr Gly
        115                 120                 125
Thr Gly Asp Tyr Trp Gly Gln Gly Thr Thr Leu Thr Val Ser Ser Ala
    130                 135                 140
Arg Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
```

```
Phe Ser Cys Ser Val Met His Glu Ala Leu His Asn His Tyr Thr Gln
    450                 455                 460
Lys Ser Leu Ser Leu Ser Pro Gly Lys
465                 470

<210> SEQ ID NO 6
<211> LENGTH: 327
<212> TYPE: DNA
<213> ORGANISM: Mus musculus

<400> SEQUENCE: 6
caaattgttc tctcccagtc tccagcaatc ctgtctgcat ctccagggga gaaggtcaca       60
atgacttgca gggccagctc aagtataaat tacatgcact ggtaccagca gaagccagga      120
tcctccccca aaccctggat ttttgccaca tccaacctgg cttctggagt cccttctcgc      180
ttcagtggca gtgggtctgg gacttcttac tctctcacca tcagcagagt ggaggctgaa      240
gatgctgcca cttattactg ccagcagtgg agaagtgacc gagcgctcac gttcggtgct      300
gggaccaagc tggagctgat acgggct                                          327

<210> SEQ ID NO 7
<211> LENGTH: 237
<212> TYPE: PRT
<213> ORGANISM: Mus musculus

<400> SEQUENCE: 7

Met Glu Thr Asp Thr Leu Leu Leu Trp Val Leu Leu Leu Trp Val Pro
1               5                   10                  15

Gly Ser Thr Gly Asp Ala Ser Gln Ile Val Leu Ser Gln Ser Pro Ala
            20                  25                  30

Ile Leu Ser Ala Ser Pro Gly Glu Lys Val Thr Met Thr Cys Arg Ala
        35                  40                  45

Ser Ser Ser Ile Asn Tyr Met His Trp Tyr Gln Gln Lys Pro Gly Ser
    50                  55                  60

Ser Pro Lys Pro Trp Ile Phe Ala Thr Ser Asn Leu Ala Ser Gly Val
65                  70                  75                  80

Pro Ser Arg Phe Ser Gly Ser Gly Ser Gly Thr Ser Tyr Ser Leu Thr
                85                  90                  95

Ile Ser Arg Val Glu Ala Glu Asp Ala Ala Thr Tyr Tyr Cys Gln Gln
            100                 105                 110

Trp Arg Ser Asp Arg Ala Leu Thr Phe Gly Ala Gly Thr Lys Leu Glu
        115                 120                 125

Leu Ile Arg Ala Ala Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 8
<211> LENGTH: 372
<212> TYPE: DNA
<213> ORGANISM: Mus musculus

<400> SEQUENCE: 8

| | | | | | |
|---|---|---|---|---|---|
| gatatacagc | ttcaggagtc | aggacctggc | ctcgtgaaac | cttctcagtc | tctgtctctc | 60 |
| acctgctctg | tcactggcta | ctccatcacc | agtgcttatt | actggaactg | gatccggcag | 120 |
| tttccaggaa | acaaactgga | atggatgggc | tacataagct | acgatggtag | gaataactac | 180 |
| aacccatctc | tcaaaaatcg | aatctccatc | actcgtgaca | catctaagaa | ccagtttttc | 240 |
| ctgaagttga | attctgtgac | tactgaggac | acagccacat | attactgtgc | aaaagagggg | 300 |
| gattacgacg | ttggaaatta | ctatgctatg | gactactggg | gtcaaggaac | ctcagtcacc | 360 |
| gtctcctcag | cc | | | | | 372 |

<210> SEQ ID NO 9
<211> LENGTH: 476
<212> TYPE: PRT
<213> ORGANISM: Mus musculus

<400> SEQUENCE: 9

Met Glu Thr Asp Thr Leu Leu Leu Trp Val Leu Leu Trp Val Pro
1               5                   10                  15

Gly Ser Thr Gly Asp Ala Ser Asp Ile Gln Leu Gln Glu Ser Gly Pro
            20                  25                  30

Gly Leu Val Lys Pro Ser Gln Ser Leu Ser Leu Thr Cys Ser Val Thr
            35                  40                  45

Gly Tyr Ser Ile Thr Ser Ala Tyr Tyr Trp Asn Trp Ile Arg Gln Phe
        50                  55                  60

Pro Gly Asn Lys Leu Glu Trp Met Gly Tyr Ile Ser Tyr Asp Gly Arg
65                  70                  75                  80

Asn Asn Tyr Asn Pro Ser Leu Lys Asn Arg Ile Ser Ile Thr Arg Asp
                85                  90                  95

Thr Ser Lys Asn Gln Phe Phe Leu Lys Leu Asn Ser Val Thr Thr Glu
            100                 105                 110

Asp Thr Ala Thr Tyr Tyr Cys Ala Lys Glu Gly Asp Tyr Asp Val Gly
        115                 120                 125

Asn Tyr Tyr Ala Met Asp Tyr Trp Gly Gln Gly Thr Ser Val Thr Val
    130                 135                 140

Ser Ser Ala Arg Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

```
Pro Pro Lys Pro Lys Asp Thr Leu Met Ile Ser Arg Thr Pro Glu Val
    275                 280                 285
Thr Cys Val Val Asp Val Ser His Glu Asp Pro Glu Val Lys Phe
    290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                325                 330                 335
Val Leu His Gln Asp Trp Leu Asn Gly Lys Glu Tyr Lys Cys Lys Val
            340                 345                 350
Ser Asn Lys Ala Leu Pro Ala Pro Ile Glu Lys Thr Ile Ser Lys Ala
        355                 360                 365
Lys Gly Gln Pro Arg Glu Pro Gln Val Tyr Thr Leu Pro Pro Ser Arg
    370                 375                 380
Asp Glu Leu Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                405                 410                 415
Glu Asn Asn Tyr Lys Thr Thr Pro Pro Val Leu Asp Ser Asp Gly Ser
            420                 425                 430
Phe Phe Leu Tyr Ser Lys Leu Thr Val Asp Lys Ser Arg Trp Gln Gln
        435                 440                 445
Gly Asn Val Phe Ser Cys Ser Val Met His Glu Ala Leu His Asn His
    450                 455                 460
Tyr Thr Gln Lys Ser Leu Ser Leu Ser Pro Gly Lys
465                 470                 475

<210> SEQ ID NO 10
<211> LENGTH: 330
<212> TYPE: DNA
<213> ORGANISM: Mus musculus

<400> SEQUENCE: 10
gaaaatgtgc tcacccagtc tccagcaatc atgtctgcat ctccagggga aaaggtcacc      60
atgacctgca gggccagctc aaatgtaatt tccagttacg tgcactggta ccagcagagg     120
tcaggtgcct cccccaaact ctggatttat agcacatcca acttggcttc tggagtccct     180
gctcgcttca gtggcagtgg gtctgggacc tcttactctc tcacaatcag cagtgtggag     240
gctgaagatg ctgccactta ttactgccag cagtacagtg gttacccact cacgttcggt     300
gctgggacca agctggagct gaaacgggct                                      330

<210> SEQ ID NO 11
<211> LENGTH: 238
<212> TYPE: PRT
<213> ORGANISM: Mus musculus

<400> SEQUENCE: 11

Met Glu Thr Asp Thr Leu Leu Leu Trp Val Leu Leu Leu Trp Val Pro
1               5                   10                  15
Gly Ser Thr Gly Asp Ala Ser Glu Asn Val Leu Thr Gln Ser Pro Ala
            20                  25                  30
Ile Met Ser Ala Ser Pro Gly Glu Lys Val Thr Met Thr Cys Arg Ala
        35                  40                  45
Ser Ser Asn Val Ile Ser Ser Tyr Val His Trp Tyr Gln Gln Arg Ser
    50                  55                  60
Gly Ala Ser Pro Lys Leu Trp Ile Tyr Ser Thr Ser Asn Leu Ala Ser
```

```
                65                  70                  75                  80
Gly Val Pro Ala Arg Phe Ser Gly Ser Gly Ser Gly Thr Ser Tyr Ser
                    85                  90                  95
Leu Thr Ile Ser Ser Val Glu Ala Glu Asp Ala Ala Thr Tyr Tyr Cys
                    100                 105                 110
Gln Gln Tyr Ser Gly Tyr Pro Leu Thr Phe Gly Ala Gly Thr Lys Leu
                    115                 120                 125
Glu Leu Lys Arg Ala Ala Ala Ala Pro Ser Val Phe Ile Phe Pro Pro
        130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
                180                 185                 190
Lys Asp Ser Thr Tyr Ser Leu Ser Ser Thr Leu Thr Leu Ser Lys Ala
                195                 200                 205
Asp Tyr Glu Lys His Lys Val Tyr Ala Cys Glu Val Thr His Gln Gly
        210                 215                 220
Leu Ser Ser Pro Val Thr Lys Ser Phe Asn Arg Gly Glu Cys
225                 230                 235
```

<210> SEQ ID NO 12
<211> LENGTH: 588
<212> TYPE: DNA
<213> ORGANISM: Homo sapiens

<400> SEQUENCE: 12

```
atagaaatga aaaaaatgaa caaactacaa aacatcagtg aagagctcca gagaaatatt      60
tctctacaac tgatgagtaa catgaatatc tccaacaaga tcaggaacct ctccaccaca     120
ctgcaaacaa tagccaccaa attatgtcgt gagctatata gcaaagaaca agagcacaaa     180
tgtaagcctt gtccaaggag atggatttgg cataaggaca gctgttattt cctaagtgat     240
gatgtccaaa catggcagga gagtaaaatg gcctgtgctg ctcagaatgc cagcctgttg     300
aagataaaca caaaaatgc attggaattt ataaaatccc agagtagatc atatgactat     360
tggctgggat tatctcctga agaagattcc actcgtggta tgagagtgga ataataatc      420
aactcctctg cctgggttat aagaaacgca cctgacttaa ataacatgta ttgtggatat     480
ataaatagac tatatgttca atattatcac tgcacttata acaaagaat gatatgtgag     540
aagatggcca atccagtgca gcttggttct acatatttta gggaggca                   588
```

<210> SEQ ID NO 13
<211> LENGTH: 30
<212> TYPE: DNA
<213> ORGANISM: Mus musculus

<400> SEQUENCE: 13

```
ggctacactt tcaccaggta ctggatgcac                                        30
```

<210> SEQ ID NO 14
<211> LENGTH: 51
<212> TYPE: DNA
<213> ORGANISM: Mus musculus

<400> SEQUENCE: 14

```
atgattcatc ctagtagtgg tagtactagc tacaatgaga aggtcaagaa c                51
```

```
<210> SEQ ID NO 15
<211> LENGTH: 32
<212> TYPE: DNA
<213> ORGANISM: Mus musculus

<400> SEQUENCE: 15
gacggggatt attactatgg tactggggac ta                                      32

<210> SEQ ID NO 16
<211> LENGTH: 10
<212> TYPE: PRT
<213> ORGANISM: Mus musculus

<400> SEQUENCE: 16

Gly Tyr Thr Phe Thr Arg Tyr Trp Met His
1               5                   10

<210> SEQ ID NO 17
<211> LENGTH: 17
<212> TYPE: PRT
<213> ORGANISM: Mus musculus

<400> SEQUENCE: 17

Met Ile His Pro Ser Ser Gly Ser Thr Ser Tyr Asn Glu Lys Val Lys
1               5                   10                  15
Asn

<210> SEQ ID NO 18
<211> LENGTH: 11
<212> TYPE: PRT
<213> ORGANISM: Mus musculus

<400> SEQUENCE: 18

Asp Gly Asp Tyr Tyr Tyr Gly Thr Gly Asp Tyr
1               5                   10

<210> SEQ ID NO 19
<211> LENGTH: 30
<212> TYPE: DNA
<213> ORGANISM: Mus musculus

<400> SEQUENCE: 19
agggccagct caagtataaa ttacatgcac                                        30

<210> SEQ ID NO 20
<211> LENGTH: 21
<212> TYPE: DNA
<213> ORGANISM: Mus musculus

<400> SEQUENCE: 20
gccacatcca acctggcttc t                                                 21

<210> SEQ ID NO 21
<211> LENGTH: 30
<212> TYPE: DNA
<213> ORGANISM: Mus musculus

<400> SEQUENCE: 21
cagcagtgga gaagtgaccg agcgctcacg                                        30

<210> SEQ ID NO 22
<211> LENGTH: 10
<212> TYPE: PRT
<213> ORGANISM: Mus musculus
```

```
<400> SEQUENCE: 22

Arg Ala Ser Ser Ser Ile Asn Tyr Met His
1               5                   10

<210> SEQ ID NO 23
<211> LENGTH: 7
<212> TYPE: PRT
<213> ORGANISM: Mus musculus

<400> SEQUENCE: 23

Ala Thr Ser Asn Leu Ala Ser
1               5

<210> SEQ ID NO 24
<211> LENGTH: 10
<212> TYPE: PRT
<213> ORGANISM: Mus musculus

<400> SEQUENCE: 24

Gln Gln Trp Arg Ser Asp Arg Ala Leu Thr
1               5                   10

<210> SEQ ID NO 25
<211> LENGTH: 33
<212> TYPE: DNA
<213> ORGANISM: Mus musculus

<400> SEQUENCE: 25
ggctactcca tcaccagtgc ttattactgg aac                             33

<210> SEQ ID NO 26
<211> LENGTH: 48
<212> TYPE: DNA
<213> ORGANISM: Mus musculus

<400> SEQUENCE: 26
tacataagct acgatggtag gaataactac aacccatctc tcaaaaat             48

<210> SEQ ID NO 27
<211> LENGTH: 42
<212> TYPE: DNA
<213> ORGANISM: Mus musculus

<400> SEQUENCE: 27 gaggggatt acgacgttgg aaattactat gctatggact ac                    42

<210> SEQ ID NO 28
<211> LENGTH: 11
<212> TYPE: PRT
<213> ORGANISM: Mus musculus

<400> SEQUENCE: 28

Gly Tyr Ser Ile Thr Ser Ala Tyr Tyr Trp Asn
1               5                   10

<210> SEQ ID NO 29
<211> LENGTH: 16
<212> TYPE: PRT
<213> ORGANISM: Mus musculus

<400> SEQUENCE: 29

Tyr Ile Ser Tyr Asp Gly Arg Asn Asn Tyr Asn Pro Ser Leu Lys Asn
1               5                   10                  15
```

```
<210> SEQ ID NO 30
<211> LENGTH: 14
<212> TYPE: PRT
<213> ORGANISM: Mus musculus

<400> SEQUENCE: 30

Glu Gly Asp Tyr Asp Val Gly Asn Tyr Tyr Ala Met Asp Tyr
1               5                   10

<210> SEQ ID NO 31
<211> LENGTH: 36
<212> TYPE: DNA
<213> ORGANISM: Mus musculus

<400> SEQUENCE: 31
agggccagct caaatgtaat ttccagttac gtgcac                         36

<210> SEQ ID NO 32
<211> LENGTH: 21
<212> TYPE: DNA
<213> ORGANISM: Mus musculus

<400> SEQUENCE: 32
agcacatcca acttggcttc t                                         21

<210> SEQ ID NO 33
<211> LENGTH: 27
<212> TYPE: DNA
<213> ORGANISM: Mus musculus

<400> SEQUENCE: 33
cagcagtaca gtggttaccc actcacg                                   27

<210> SEQ ID NO 34
<211> LENGTH: 12
<212> TYPE: PRT
<213> ORGANISM: Mus musculus

<400> SEQUENCE: 34

Arg Ala Ser Ser Asn Val Ile Ser Ser Tyr Val His
1               5                   10

<210> SEQ ID NO 35
<211> LENGTH: 7
<212> TYPE: PRT
<213> ORGANISM: Mus musculus

<400> SEQUENCE: 35

Ser Thr Ser Asn Leu Ala Ser
1               5

<210> SEQ ID NO 36
<211> LENGTH: 9
<212> TYPE: PRT
<213> ORGANISM: Mus musculus

<400> SEQUENCE: 36

Gln Gln Tyr Ser Gly Tyr Pro Leu Thr
1               5
```

ANTIBODIES TO CLL-1

CROSS-REFERENCE TO PRIOR APPLICATIONS

This application is a national phase application under 35 U.S.C. §371 of International Application No. PCT/US2008/078702 filed Oct. 3, 2008, which claims the benefit of priority Under 35 U.S.C. §119(e)(1) of provisional application Ser. No. 60/980,567, filed Oct. 17, 2007, which applications are hereby incorporated by reference in their entirety

TECHNICAL FIELD OF THE INVENTION

The present invention relates to anti-CLL-1 antibodies and to binding epitopes of CLL-1 used to produce such antibodies. The invention also relates to methods of using such antibodies to diagnose and treat CLL-1 associated diseases including cancer.

SEQUENCE LISTING

The sequences of the polynucleotides and polypeptides of the invention are listed in the Sequence Listing and are submitted electronically in the file labeled "NUVO-33PCT_ST25.txt"—27.9 KB (28,591 bytes) which was created on an IBM PC, Windows 2000 operating system on Sep. 23, 2008 at 02:44:22 PM. The Sequence Listing entitled "NUVO-33PCT_ST25.txt" is herein incorporated by reference in its entirety.

BACKGROUND OF THE INVENTION

Antibody therapy for cancer often involves the use of antibodies, or antibody fragments, against a tumor antigen to target antigen-expressing cells. Antibodies, or antibody fragments, may have direct or indirect cytotoxic effects on cancer cells. Direct effects include the induction of apoptosis, the blocking of growth factor receptors, and anti-idiotype antibody formation. Indirect effects include antibody-dependent cell-mediated cytotoxicity (ADCC) and complement-mediated cellular cytotoxicity (CDC). When conjugated or fused to cytotoxic moieties, the antibodies, or fragments thereof, provide a method of targeting the cytotoxic moiety towards the tumor antigen-expressing cells (Green, et al., *Cancer Treatment Reviews*, 26:269-286 (2000)).

Because antibody therapy typically targets cells expressing a particular antigen, there is a possibility of cross-reactivity with those normal cells or tissues that express the same or a highly similar antigen. Although some cells, such as hematopoietic cells, are readily regenerated, cross-reactivity with many non-cancerous cells or tissues can lead to detrimental results. Thus, considerable research has focused on identifying tumor-specific antigens. Such antigens are found almost exclusively on tumors or are expressed at a greater level in tumor cells than the corresponding normal tissue. Tumor-specific antigens provide targets for anti-cancer therapies. Antibodies specific to such tumor-specific antigens can be conjugated to cytotoxic compounds or can be used alone in immunotherapy. Immunotoxins target cytotoxic compounds to induce cell death. For example, anti-CD22 antibodies conjugated to deglycosylated ricin A may be used for treatment of B cell lymphoma that has relapsed after conventional therapy (Amlot, et al., *Blood* 82:2624-2633 (1993)).

Immunotherapy provides a method of harnessing the immune system to treat various pathological states, such as cancer, autoimmune disease, transplant rejection, hyperproliferative conditions, inflammatory diseases, and allergic reactions. The immune system functions to eliminate organisms or cells that are recognized as non-self, including microorganisms, neoplasms and transplants. A cell-mediated host response to tumors includes the concept of immunologic surveillance, by which cellular mechanisms associated with cell-mediated immunity, destroy newly transformed tumor cells after recognizing tumor-associated antigens (i.e., antigens associated with tumor cells that are not apparent on normal cells). Furthermore, a humoral response to tumor-associated antigens enables destruction of tumor cells through immunological processes triggered by the binding of an antibody to the surface of a cell, such as ADCC and CDC.

Recognition of an antigen by the immune system can trigger a cascade of events including cytokine production, B-cell proliferation, and subsequent antibody production. Often tumor cells have reduced capability of presenting antigen to effector cells, thus impeding the immune response against a tumor-specific antigen. In some instances, the tumor-specific antigen may not be recognized as non-self by the immune system, preventing an immune response against the tumor-specific antigen from occurring. In such instances, stimulation or manipulation of the immune system provides effective techniques of treating cancers expressing one or more tumor-specific antigens.

For example, rituximab (RITUXAN®, Biogen DEC, Inc., Cambridge, Mass., USA) is a chimeric antibody directed against CD20, a B cell-specific surface molecule found on >95% of B-cell non-Hodgkin's lymphoma (Press, et al., *Blood* 69:584-591 (1987); Malony, et al., *Blood* 90: 2188 (1997)). Rituximab induces ADCC and inhibits cell proliferation through apoptosis in malignant B cells in vitro (Maloney, et al., *Blood* 88 637a (1996)). Rituximab is currently used as a therapy for advanced stage or relapsed low-grade non-Hodgkin's lymphoma, which has not responded to conventional therapy.

MYLOTARG® (Wyeth, N.J.; gentuzumab ozogamicin), a chimeric antibody directed against CD33, is an example of an alternative targeted antibody therapy. In this case, the antibody is conjugated to a cytotoxic molecule, calicheamicin. Thus, when the antibody binds to the target cell and is internalized, the cytotoxic molecule kills the cells. MYLO-TARG® is currently used as a therapy for patients over the age of 60 with relapsed acute myelogenous leukemia who are not considered candidates for standard chemotherapy.

Several cell surface receptors are predominantly expressed in hematologic malignancies, such as leukemias and lymphomas. Some of these molecules belong to the C-type lectin-like family which is involved in processes such as regulation of cell proliferation. One such member of the C-type lectin-like family, CLL-1, is a cell surface glycoprotein whose expression is restricted to myeloid cells and may have a role in regulating myeloid cell proliferation and differentiation (Bakker et al., *Cancer Res.* 64:8443-8450 (2004); Marshall et al., *J. Biol. Chem.* 279:14792-14802 (2004)).

The currently available therapies for hematologic malignancies carry adverse and often severe side effects. For example, complications arising from MYLOTARG® administration include hepatotoxicity, veno-occlusive disease, severe myelosuppression (in ~98% of patients), tumor lysis syndrome, immune hypersensitivity syndrome and respiratory disorders. Thus, there is a need to identify new therapies for hematologic malignancies that are efficacious with reduced side effects. Since CLL-1 is selectively expressed on myeloid cells, compositions that recognize and bind to CLL-1 may be useful for such therapies of hematogic malignanices, especially those of myeloid origin.

SUMMARY OF THE INVENTION

The present invention provides isolated antibodies or immunologically functional antibody fragments (i.e. antigen-binding fragments) thereof that bind CLL-1 epitopes with high affinity, which antibodies can be used for treating a variety of diseases in which CLL-1 is implicated, such as hematologic malignancies, including leukemias. Preferably the antibodies or antibody fragments thereof bind to primate and human CLL-1. More preferably, the antibodies and antigen-binding fragments bind with high affinity to human CLL-1. In particular embodiments, the antibodies or antigen-binding fragments thereof are chimeric, humanized, or human antibodies or antigen-binding fragments thereof. In other embodiments, the antibodies or antigen-binding fragments thereof are selected from the group consisting of scFv, Fab, Fab', F(ab')$_2$, Fv, and single chain antibodies. In another particular embodiment, the antibody or antigen-binding fragment thereof is an IgG isotype, such as an IgG$_1$ isotype.

One aspect of the present invention provides antibodies or antibody fragments thereof comprising a heavy chain variable region ($V_H$) and/or a light chain variable region ($V_L$) of anti-CLL-1 antibodies 21.16 and 1075.7. In a particular embodiment, the antibodies of the invention comprise a heavy chain variable region of SEQ ID NO: 5 and/or a light chain variable region of SEQ ID NO: 7. In another embodiment, the antibodies comprise a heavy chain variable region comprising a sequence that has at least 90%, at least 95%, at least 96%, at least 97%, at least 98% or at least 99% identity to the amino acid sequence set forth in SEQ ID NO: 5 and/or a light chain variable region comprising a sequence that has at least 90%, at least 95%, at least 96%, at least 97%, at least 98% or at least 99% identity to the amino acid sequence set forth in SEQ ID NO: 7. In a particular embodiment, the antibodies comprise a heavy chain variable region of SEQ ID NO: 9 and/or a light chain variable region of SEQ ID NO: 11. In another embodiment, the antibodies comprise a heavy chain variable region comprising a sequence that has at least 90%, at least 95%, at least 96%, at least 97%, at least 98% or at least 99% identity to the amino acid sequence set forth in SEQ ID NO: 9 and/or a light chain variable region comprising a sequence that has at least 90%, at least 95%, at least 96%, at least 97%, at least 98% or at least 99% identity to the amino acid sequence set forth in SEQ ID NO: 11.

Some of the antibodies and antigen-binding fragments that are provided include (a) one or more light chain (LC) complementarity determining regions (CDRs) selected from the group consisting of:
  (i) a LC CDR1 with at least 80% sequence identity to SEQ ID NO: 22 or 34;
  (ii) a LC CDR2 with at least 80% sequence identity to SEQ ID NO: 23 or 35; and
  (iii) a LC CDR3 with at least 80% sequence identity to SEQ ID NO: 24 or 36;
(b) one or more heavy chain (HC) CDRs selected from the group consisting of:
  (i) a HC CDR1 with at least 80% sequence identity to SEQ ID NO: 16 or 28;
  (ii) a HC CDR2 with at least 80% sequence identity to SEQ ID NO: 17 or 29; and
  (iii) a HC CDR3 with at least 80% sequence identity to SEQ ID NO: 18 or 30; or
(c) one or more LC CDRs of (a) and one or more HC CDRs of (b).

Such antibodies or antigen-binding fragments thereof can specifically bind an CLL-1 polypeptide. Certain antibodies or antigen-binding fragments thereof include one, two, three, four, five or six of the foregoing CDRs in any combination thereof.

The light chain and heavy chains of other antibodies or antigen-binding fragments thereof are as described above but have at least 90% sequence identity to the foregoing sequences. Still other antibodies or antigen-binding fragments thereof provided herein have a light chain in which CDR1 has the amino acid sequence as set forth in SEQ ID NO: 22, CDR2 has the amino acid sequence as set forth in SEQ ID NO: 23, and/or CDR3 has the amino acid sequence as set forth in SEQ ID NO: 24. Still other antibodies or antigen-binding fragments thereof have a light chain in which CDR1 has the amino acid sequence as set forth in SEQ ID NO: 34, CDR2 has the amino acid sequence as set forth in SEQ ID NO: 35, and/or CDR3 has the amino acid sequence as set forth in SEQ ID NO: 36. Some antibodies or antigen-binding fragments thereof may also have a heavy chain in which CDR1 has the amino acid sequence as set forth in SEQ ID NO: 16, CDR2 has the amino acid sequence as set forth in SEQ ID NO: 17, and/or CDR3 has the amino acid sequence as set forth in SEQ ID NO: 18. Some antibodies or antigen-binding fragments thereof may also have a heavy chain in which CDR1 has the amino acid sequence as set forth in SEQ ID NO: 28, CDR2 has the amino acid sequence as set forth in SEQ ID NO: 29, and/or CDR3 has the amino acid sequence as set forth in SEQ ID NO: 30.

Another aspect of the present invention provides isolated antibodies or antigen-binding fragments thereof that bind to CLL-1 or a CLL-1 epitope. Examples of such antibodies include monoclonal antibodies 21.16 and 1075.7.

Yet another aspect of the invention provides isolated CLL-1 antibodies or antigen-binding fragments that are conjugated to another molecule, such as a cytotoxic agent or a radionuclide. In yet a further embodiment, the anti-CLL-1 antibodies or antigen-binding fragments are conjugated to an enzyme that converts a prodrug into a cytotoxic drug.

The invention provides a pharmaceutical composition comprising the antibody and a pharmaceutically acceptable carrier. The pharmaceutical composition may further comprise another pharmaceutically active ingredient, such as an anti-tumor agent or an imaging reagent. A particular embodiment provides an antibody or antigen-binding fragment thereof present in a therapeutically effective amount, such as in a concentration of at least about 10 μg/ml.

Another aspect of the invention provides CLL-1 epitopes, which epitopes include isolated polypeptides comprising SEQ ID NO: 3, or any fragment thereof that binds to an antibody or antigen-binding fragment thereof provided herein.

Diagnostic and therapeutic methods are also provided by the invention. A particular embodiment provides a method for diagnosing the presence or location of a CLL-1-expressing tissue or cells using an anti-CLL-1 antibody. In yet another embodiment, a therapeutic method comprises administering the antibody to a subject in need thereof. In yet a further embodiment, a therapeutic method comprises administering the antibody to a subject in need thereof in conjunction with administration of another therapeutic agent.

The invention provides isolated cell lines, such as hybridoma cells and/or host cells that have been transfected to express CLL-1 antibodies or antigen-binding fragments thereof, that produce the antibody or antigen-binding fragment thereof, and antibodies or antigen-binding fragments thereof produced by such cell lines. A hybridoma may include B cells obtained from a transgenic non-human animal having a genome comprising a human heavy chain transgene and a human light chain transgene fused to an immortalized cell. In another aspect, a hybridoma may include B cells obtained from a non-transgenic, non-human animal. Such transformed host cells may include nucleic acids encoding a human heavy chain and a human light chain.

Another aspect of the present invention provides a method of producing an antibody or antigen-binding fragment thereof that binds with high affinity to a human CLL-1 epitope, such that antibodies are produced by B cells of the animal; isolating the B cells of the animal; and fusing the B cells with myeloma cells to form immortal, hybridoma cells that secrete the antibody or antigen binding region thereof.

The invention also provides nucleic acid molecules encoding the heavy and/or light chain or antigen-binding portions thereof of an anti-CLL-1 antibody.

The invention provides vectors and host cells comprising the nucleic acid molecules, as well as methods of recombinantly producing the polypeptides encoded by the nucleic acid molecules.

BRIEF DESCRIPTION OF THE DRAWINGS

FIG. 1A: Expression of CLL-1 in normal human peripheral blood cells by flow cytometry (FACS) analysis using an anti-CLL-1 antibody.

FIG. 1B: Expression of CLL-1 and CD33 in acute myelogenous leukemia cell lines (AML; staged using FAB Classification), CML=chronic myelogenous leukemia, using an anti-CLL-1 mAb.

DETAILED DESCRIPTION OF THE INVENTION

Figure 1C:
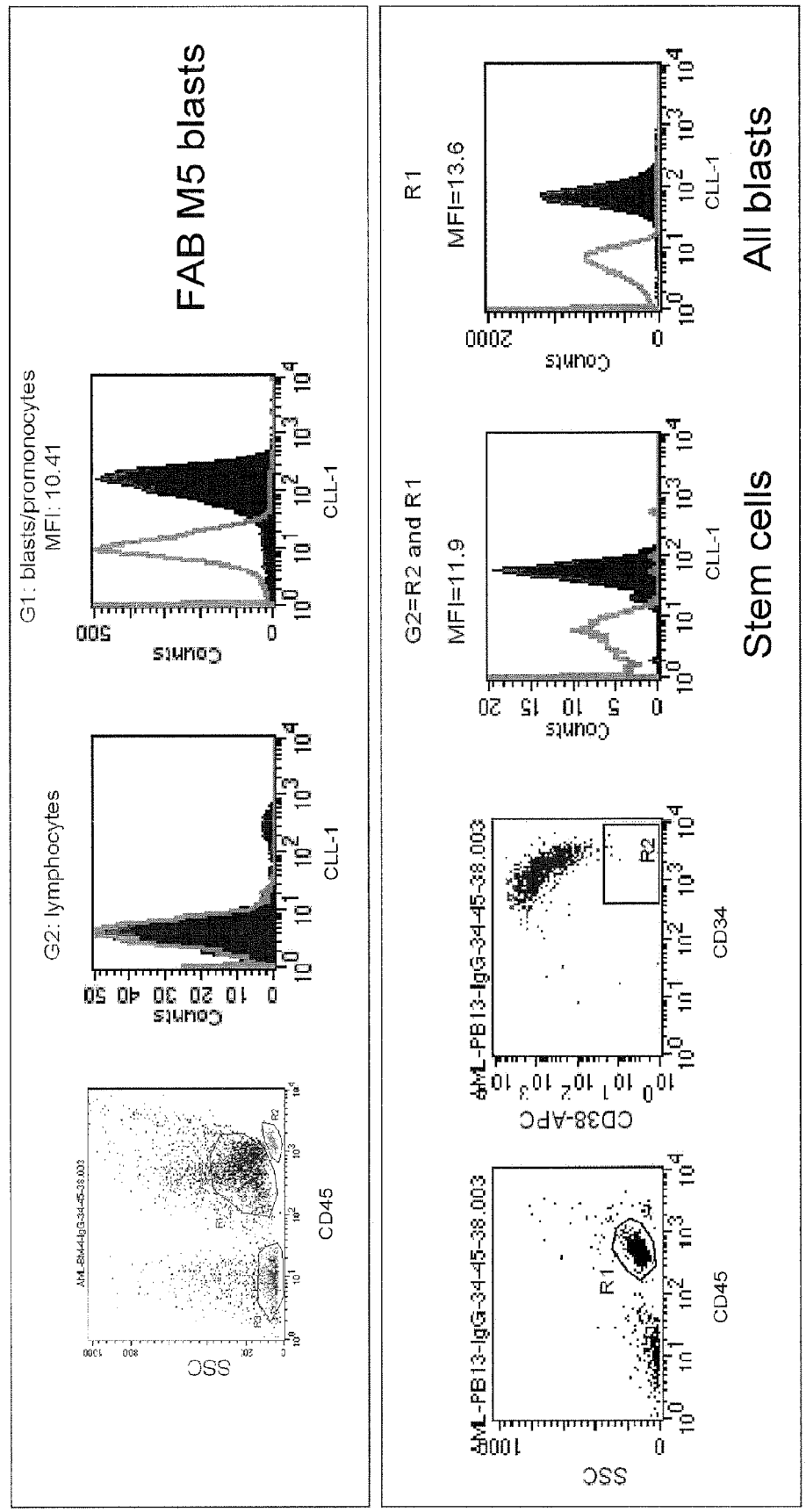
FIG. 1C: Expression of CLL-1 in AML blasts and $CD34^+$/$CD38^-$ AML stem cells by flow cytometry (FACS) analysis using an anti-CLL-1 antibody.

Section titles are used herein for convenience purposes only and are not to be construed in any way as limiting the invention.

I. Definitions

Unless otherwise defined herein, scientific and technical terms used in connection with the present invention have the meanings that are commonly understood by those of ordinary skill in the art. Further, unless otherwise required by context, singular terms shall include pluralities and plural terms shall include the singular. Unless otherwise indicated, nucleic acids are written left to right in 5' to 3' orientation; amino acid sequences are written left to right in amino to carboxy orientation.

Standard techniques are used for recombinant DNA, oligonucleotide synthesis, and tissue culture and transformation (e.g. electroporation, lipofection). Enzymatic reactions and purification techniques are performed according to manufacturer's specifications or as commonly accomplished in the art or as described herein. The foregoing techniques and procedures are as generally performed according to conventional methods well known in the art and as described in various general and more specific references that are cited and discussed throughout the present specification. See Sambrook et al., *Molecular Cloning: A Laboratory Manual,* 2d ed., Cold Spring Harbor Laboratory Press, Cold Spring Harbor, N.Y. (1989), Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990), which are incorporated herein by reference in their entirety for all purposes. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The terms "a," "an," and "the" mean one or more and include the plural unless the context is inappropriate.

The term "polynucleotide" as referred to herein means a polymeric form of nucleotides of at least 10 bases in length, either ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a gene mutant. Oligonucleotides of the invention can be either sense or antisense oligonucleotides.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and when desired, sequences that enhance protein secretion. The nature of such control sequences differs depending upon the host organism; in prokaryotes, such control sequences generally include promoters and transcription termination sequence. The term "control sequences" as referred to herein includes, at a minimum, all components whose presence is essential for expression and processing, and can also include additional components whose presence is advantageous, for example, leader sequences and fusion partner sequences.

The term "vector" as used herein, refers to a nucleic acid molecule capable of transporting another nucleic acid to which it has been linked. One type of vector is a "plasmid", which refers to a circular double stranded loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors (e.g., replication defective retroviruses, adenoviruses and adeno-associated viruses), which serve equivalent functions.

The term "recombinant host cell" (or simply "host cell"), as used herein, refers to a cell that has been transformed, or is capable of being transformed, with a nucleic acid sequence and thereby expresses a gene of interest. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Host cells may be prokaryotic or eukaryotic cells that are capable of expressing exogenous nucleic acid sequences. Examples of host cells include bacteria such as *E. coli*, yeast, plant cells, Chinese hamster ovary (CHO) cells, human embryonic kidney (HEK)-293 cells and insect cells.

The term "transduction" means the transfer of genes from one bacterium to another, usually by bacteriophage. "Transduction" also refers to the acquisition and transfer of eukaryotic cellular sequences by retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., *Virology* 52:456 (1973); Sambrook et al., *Molecular Cloning: A Laboratory Manual, Id.* (2001); Davis et al., *Basic Methods in Molecular Biology*, Elsevier (1986); and Chu et al., *Gene* 13:197 (1981). Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed wherein it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The term "percent sequence identity" in the context of nucleic acid sequences refers to the residues in two sequences which are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, GAP or BESTFIT, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Meth. Enzymol.* 183:63-98 (1990); Pearson, *Meth. Mol. Biol.* 132:185-219 (2000); Pearson, *Meth. Enzymol.* 266:227-258 (1996); Pearson, J. Mol. Biol. 276:71-84 (1998); herein incorporated by reference). Unless specified otherwise, default parameters for a particular program or algorithm are used. For instance, percent sequence identity between nucleic acid sequences can be determined using FASTA with its default parameters (a word size of 6 and the NOPAM factor for the scoring matrix) or using GAP with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence.

The term "substantial similarity" or "substantial sequence similarity" when referring to a nucleic acid or fragment thereof, indicates that, when optimally aligned with appropriate nucleotide insertions or deletions with another nucleic acid (or its complementary strand), there is nucleotide sequence identity in at least about 85%, preferably at least about 90%, and more preferably at least about 95%, at least 96%, at least 97%, at least 98% or at least 99% of the nucleotide bases, as measured by any well-known algorithm of sequence identity, such as FASTA, BLAST, or GAP as discussed above.

The terms "polypeptide" or "protein" means a macromolecule having the amino acid sequence of a native protein, that is a protein produced by a naturally-occurring and non-recombinant cell, or produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass anti-CLL-1 antibodies, antigen-binding fragments, or sequences that have deletions from, additions to, and/or substitutions of one or more amino acid of anti-CLL-1 antibodies or antigen-binding fragments. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about 5 to 500 amino acids long. For example, fragments may be at least 5, 6, 8, 10, 14, 20, 50, 70, 100, 110, 150, 200, 250, 300, 350, 400, 450 or 500 amino acids long. Useful polypeptide fragments for this invention include immunologically functional fragments of antibodies, including binding domains. In the case of anti-CLL-1 antibodies, useful fragments include but are not limited to a CDR region, a variable domain of a heavy or light chain, a portion of an antibody chain or just its variable region including two CDRs, and the like.

The term "isolated protein" referred to herein, means that a subject protein (1) is free of at least some other proteins with which it would normally be found, (2) is essentially free of other proteins from the same source, e.g., from the same species, (3) is expressed by a cell from a different species, (4) has been separated from at least about 50% of polynucleotides, lipids, carbohydrates, or other materials with which it is associated in nature, (5) is operably associated (by covalent or noncovalent interaction) with a polypeptide with which it is not associated in nature, or (6) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified in some manner distinct from insertion, deletion, or substitution variants, e.g., via conjugation to another chemical moiety.

The term "antibody" refers to an intact immunoglobulin of any isotype, or a fragment thereof, that can compete with the intact antibody for specific binding to the target antigen, and includes chimeric, humanized, fully human, and bispecific antibodies. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies. For example, the CDR regions may be derived from a rat or murine source, while the framework region of the V region is derived from a different animal source, such as a human. The antibodies or binding fragments may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

The term "light chain" includes a full-length light chain and fragments thereof having sufficient variable region sequence to confer binding specificity. A full-length light chain includes a variable region domain (abbreviated herein as $V_L$), and a constant region domain (abbreviated herein as $C_L$). The variable region domain of the light chain is at the amino-terminus of the polypeptide. The light chains include kappa chains and lambda chains.

The term "heavy chain" includes a full-length heavy chain and fragments thereof having sufficient variable region sequence to confer binding specificity. A full-length heavy chain includes a variable region domain (abbreviated herein as $V_H$), and three constant region domains (abbreviated herein as $C_H1$, $C_H2$, and $C_H3$). The $V_H$ domain is at the amino-terminus of the polypeptide, and the $C_H$ domains are at the carboxy-terminus, with the $C_H3$ being closest to the —COOH end. Heavy chains may be of any isotype, including IgG (including $IgG_1$, $IgG_2$, $IgG_3$, and $IgG_4$ subtypes), IgA (including $IgA_1$ and $IgA_2$ subtypes), IgM, and IgE.

The $V_H$ and $V_L$ regions can be further subdivided into regions of hypervariability, termed "complementarity determining regions" or "CDR", interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3. CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An amino acid sequence which is substantially the same as a heavy or light chain CDR exhibits a considerable amount or extent of sequence identity when compared to a reference sequence and contributes favorably to specific binding of an antigen bound specifically by an antibody having the reference sequence. Such identity is definitively known or recognizable as representing the amino acid sequence of the particular human monoclonal antibody. Substantially the same heavy and light chain CDR amino acid sequence can have, for example, minor modifications or conservative substitutions of amino acids so long as the ability to bind a particular antigen is maintained.

The term "CDR" or "complementarity determining region" means the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987) and additionally by MacCallum et al., J. Mol. Biol. 262:732-745 (1996), which are incorporated herein by reference, where the definitions include overlapping or subsets of amino acid residues when compared against each other. Nevertheless, application of either definition to refer to a CDR of an antibody or functional fragment thereof is intended to be within the scope of the term as defined and used herein. The exact amino acid residue numbers which encompass a particular CDR will vary depending on the structure of the CDR. Those skilled in the art can routinely determine which residues comprise a particular CDR given the variable region amino acid sequence of the antibody. Those skilled in the art can compare two or more antibody sequences by defining regions or individual amino acid positions of the respective sequences with the same CDR definition.

The term "antibody" includes both glycosylated and non-glycosylated immunoglobulins of any isotype or subclass or combination thereof, including human (including CDR-grafted antibodies), humanized, chimeric, multi-specific, monoclonal, polyclonal, and oligomers thereof, irrespective of whether such antibodies are produced, in whole or in part, via immunization, through recombinant technology, by way of in vitro synthetic means, or otherwise. Thus, the term "antibody" includes those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody, (c) antibodies isolated from a recombinant, combinatorial library, and (d) antibodies prepared, expressed, created or isolated by any other means that involve splicing of immunoglobulin gene sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the $V_H$ and $V_L$ regions of the antibodies are sequences that, while derived from and related to the germline $V_H$ and $V_L$ sequences of a particular species (e.g., human), may not naturally exist within that species' antibody germline repertoire in vivo.

The term "antigen-binding fragment" of an antibody means one or more fragments of an antibody that retain the ability to specifically bind to an antigen (e.g., CLL-1) that is specifically bound by a reference antibody, as disclosed herein. An "antigen-binding fragment" of an antibody may include, for example, polypeptides comprising individual heavy or light chains and fragments thereof, such as $V_L$, $V_H$, and Fd regions (consisting of the $V_H$ and $C_H1$ domains); monovalent fragments, such as Fv, Fab, and Fab' regions; bivalent fragments, such as $F(ab')_2$; single chain antibodies, such as single chain Fv (scFv) regions; Fc fragments; diabodies; maxibodies (bivalent scFv fused to the amino terminus of the Fc ($C_H2$-$C_H3$ domains)) and complementary determining region (CDR) domains. Such terms are described, for example, in Harlow and Lane, *Antibodies: A Laboratory Manual*, Cold Spring Harbor Laboratory, NY (1989); *Molec. Biology and Biotechnology: A Comprehensive Desk Reference* (Myers, R. A. (ed.), New York: VCH Publisher, Inc.); Huston et al., *Cell Biophysics*, 22:189-224 (1993); Pluckthun and Skerra, *Meth. Enzymol.*, 178:497-515 (1989) and in Day, E. D., *Advanced Immunochemistry*, 2d ed., Wiley-Liss, Inc. New York, N.Y. (1990), which are incorporated herein by reference.

The term "antigen-binding fragment" also includes, for example, fragments produced by protease digestion or reduction of a human monoclonal antibody and by recombinant DNA methods known to those skilled in the art. One skilled in the art knows that the exact boundaries of a fragment of a human monoclonal antibody can be variable, so long as the fragment maintains a functional activity. Using well-known recombinant methods, one skilled in the art can engineer a nucleic acid to express a functional fragment with any endpoints desired for a particular application. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., *Science* 242:423-426 (1988); and Huston et al., *Proc. Natl. Acad. Sci. USA* 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Such fragments include those obtained by amino-terminal and/or carboxy-terminal deletions, but where the remaining amino acid sequence is substantially identical to the corresponding positions in the naturally-occurring sequence deduced, for example, from a full-length cDNA sequence. Antigen-binding fragments also include fragments of an antibody which retain at least one (e.g., 1, 2, 3 or more) light chain sequences for a particular complementarity determining region (CDR) (e.g., at least one or more of CDR1, CDR2, and/or CDR3 from the heavy and/or light chain). Fusions of CDR containing sequences to an Fc region (or a $C_H2$ or $C_H3$ region thereof) are included within the scope of this definition including, for example, scFv fused, directly or indirectly, to an Fc region are included herein. An antigen-binding fragment is inclusive of, but not limited to, those derived from an antibody or fragment thereof (e.g., by enzymatic digestion or reduction of disulfide bonds), produced synthetically using recombinant methods, created via in vitro synthetic means (e.g., Merrifield resins), combinations thereof, or through other methods. Antigen-binding fragments may also comprise multiple fragments, such as CDR fragments, linked together synthetically, chemically, or otherwise, in the form of oligomers. Thus, antigen-binding fragments as disclosed herein include polypeptides produced by any number of methods which comprise at least one CDR from a $V_H$ or $V_L$ chain (e.g., derived from monoclonal antibodies 21.16 or 1075.7).

The term "$V_L$ fragment" means a fragment of the light chain of a monoclonal antibody which includes all or part of the light chain variable region, including the CDRs. A $V_L$ fragment can further include light chain constant region sequences.

The term "$V_H$ fragment" means a fragment of the heavy chain of a monoclonal antibody which includes all or part of the heavy chain variable region, including the CDRs. A $V_H$ fragment can further include heavy chain constant region sequences.

The term "Fd fragment" means a fragment of the heavy chain of a monoclonal antibody which includes all or part of the $V_H$ heavy chain variable region, including the CDRs. An Fd fragment can further include $C_H1$ heavy chain constant region sequences.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domain.

The term "Fv fragment" means a monovalent antigen-binding fragment of a monoclonal antibody, including all or part of the variable regions of the heavy and light chains, and absent of the constant regions of the heavy and light chains. The variable regions of the heavy and light chains include, for example, the CDRs.

The term "Fab fragment" means a monovalent antigen-binding fragment of an antibody consisting of the $V_L$, $V_H$, $C_L$ and $C_H1$ domains, which is larger than an Fv fragment. For example, a Fab fragment includes the variable regions, and all or part of the first constant domain of the heavy and light chains.

The term "Fab' fragment" means a monovalent antigen-binding fragment of a monoclonal antibody that is larger than a Fab fragment. For example, a Fab' fragment includes all of the light chain, all of the variable region of the heavy chain, and all or part of the first and second constant domains of the heavy chain.

The term "$F(ab')_2$ fragment" means a bivalent antigen-binding fragment of a monoclonal antibody comprising two Fab fragments linked by a disulfide bridge at the hinge region. An $F(ab')_2$ fragment includes, for example, all or part of the variable regions of two heavy chains and two light chains, and can further include all or part of the first constant domains of two heavy chains and two light chains.

"Single-chain antibodies" are Fv molecules in which the heavy and light chain variable regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorporated by reference.

A "domain antibody" is an antigen-binding fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The term "bivalent antibody" means an antibody that comprises two antigen binding sites. In some instances, the two binding sites have the same antigen specificities. However, bivalent antibodies may be bispecific (see below).

The term "bispecific antibody" means an antibody that binds to two or more distinct epitopes. For example, the antibody may bind to, or interact with, (a) a cell surface antigen and (b) an Fc receptor on the surface of an effector cell. The term "multispecific antibody" or "heterospecific antibody" means an antibody that binds to more than two distinct epitopes. For example, the antibody may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific antibodies or antigen-binding fragments thereof which are directed to CLL-1 epitopes and to other targets, such as Fc receptors on effector cells. Bispecific antibodies are a species of multispecific antibody and may be produced by a variety of methods including, but not limited to, fusion of hybridomas or linking of Fab' fragments. See, e.g., Songsivilai and Lachmann, *Clin. Exp. Immunol.* 79:315 (1990); Kostelny et al., *J. Immunol.* 148:1547 (1992). The two binding sites of a bispecific antibody will bind to two different epitopes, which may reside on the same or different protein targets.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Hollinger et al., *Proc Natl. Acad. Sci. USA* 90:6444-6448 (1993); Polijak et al., *Structure* 2:1121-1123 (1994).

The term "monoclonal antibody" or "mAb," as used herein, refers to an antibody obtained from a population of substantially homogeneous antibodies, e.g., the individual antibodies comprising the population are identical except for possible naturally occurring mutations that may be present in minor amounts. In contrast to polyclonal antibody preparations that typically include different antibodies against different determinants (epitopes), each monoclonal antibody is directed against a single determinant on the antigen. The term is not limited regarding the species or source of the antibody, nor is it intended to be limited by the manner in which it is made. The term encompasses whole immunoglobulins as well as fragments such as Fab, F(ab')$_2$, Fv, and other fragments, as well as chimeric and humanized homogeneous antibody populations, that exhibit immunological binding properties of the parent monoclonal antibody molecule.

The term "mouse monoclonal antibody" means a monoclonal antibody, as defined above, produced by immunizing a mouse, with an antigen of interest (e.g., CLL-1). A "mouse monoclonal antibody" is produced using conventional methods well known in the art, from mouse-mouse hybridomas, described more fully below.

The term "rabbit monoclonal antibody" as used herein means a monoclonal antibody, as defined above, produced by immunizing a rabbit with an antigen of interest (e.g., CLL-1). A "rabbit monoclonal antibody" can be produced using rabbit-rabbit hybridomas (e.g., fusions between an antibody-producing cell from the immunized rabbit with an immortalized cell from a rabbit), rabbit-mouse hybridomas (e.g., fusions between an antibody-producing cell from the immunized rabbit with an immortalized cell from a mouse), and the like.

The term "human monoclonal antibody" means a monoclonal antibody with substantially human CDR amino acid sequences produced, for example, by recombinant methods, by lymphocytes or by hybridoma cells.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851 (1984).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or nonhuman primate having the desired specificity, affinity, and capacity. In some instances, framework region (FR) residues of the immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., *Nature* 321:522 (1986); Riechmann et al., *Nature* 332:323 (1988); Presta, *Curr. Op. Struct. Biol.* 2:593 (1992); Vaswani and Hamilton, *Ann. Allergy, Asthma and Immunol.* 1:105 (1998); Harris, *Biochem. Soc. Transactions* 23;1035 (1995); Hurle and Gross, *Curr. Op. Biotech.* 5:428 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding regions.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., *Bio/Technology* 10:779 (1992) describes affinity maturation by $V_H$ and $V_L$ domain shuffling.

Random mutagenesis of CDR and/or framework residues is described by: Barbas et al., *Proc. Natl. Acad. Sci. USA* 91:3809 (1994); Schier et al., *Gene* 169:147 (1995); Yelton et al., *J. Immunol.* 155:1994 (1995); Jackson et al., *J. Immunol.* 154:3310 (1995); and Hawkins et al., *J. Mol. Biol.* 226:889 (1992).

"Immunoadhesions" or "immunoadhesins" are antibody-like molecules that combine the binding domain of a non-antibody polypeptide with the effector functions of an antibody or an antibody constant domain. The binding domain of the non-antibody polypeptide can be, for example, a ligand or cell surface receptor having ligand binding activity. Immunoadhesions for use as anti-CLL-1 antibodies can contain at least the Fc receptor binding effector functions of the antibody constant domain.

"Immunologically reactive" means that the antibody of interest will bind with CLL-1 antigens present in a biological sample.

The term "immunogenic sequence of a CLL-1" means an CLL-1 molecule that includes an amino acid sequence with at least one epitope such that the molecule is capable of stimulating the production of antibodies in an appropriate host.

The term "immunogenic composition" means a composition that comprises at least one immunogenic polypeptide (e.g., an CLL-1 antigen or antibody).

The term "antigen" refers to a molecule or a portion of a molecule capable of being bound by a selective binding agent, such as an antibody, and additionally capable of being used in an animal to produce antibodies capable of binding to that antigen. An antigen may possess one or more epitopes that are capable of interacting with different antibodies.

The term "selective binding agent" refers to a molecule that binds to an antigen. Non-limiting examples include antibodies, antigen-binding fragments, scFv, Fab, Fab', F(ab')$_2$, single chain antibodies, peptides, peptide fragments and proteins.

The term "epitope" includes any determinant capable of binding with high affinity to an immunoglobulin or to a T-cell receptor. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. *Proc. Natl. Acad. Sci. USA* 81:3998-4002 (1984); Geysen et al. *Proc. Natl. Acad. Sci. USA* 82:178-182 (1985); Geysen et al. *Molec. Immunol.* 23:709-715 (1986). Similarly, conformational epitopes are readily identified by determining spatial conformation of amino acids such as by, e.g., x-ray crystallography and two-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* 78:3824-3828 (1981) for determining antigenicity profiles, and the Kyte-Doolittle technique, Kyte et al., *J. Mol. Biol.* 157:105-132 (1982) for hydropathy plots.

An antibody is said to "specifically bind" its target antigen when the dissociation constant ($K_D$) is $\leq 10^{-8}$ M. The antibody specifically binds antigen with "high affinity" when the $K_D$ is $\leq 5 \times 10^{-9}$ M, and with "very high affinity" when the $K_D$ is $\leq 5 \times 10^{-10}$ M. In one embodiment of the invention, the antibody has a $K_D$ of $\leq 10^{-9}$ M and an off-rate ($k_d$) of about $1 \times 10^{-4}$/sec. In one embodiment of the invention, the off-rate is $< 1 \times 10^{-5}$/sec. In other embodiments of the invention, the antibodies will bind to human CLL-1 with a $K_D$ of between $10^{-8}$ M and $10^{-10}$ M.

The term "surface plasmon resonance," as used herein, refers to an optical phenomenon that allows for the analysis of real-time biospecific interactions by detection of alterations in protein concentrations within a biosensor matrix, for example using the BIAcore system (Biacore International AB, Uppsala, Sweden). For further descriptions, see Jonsson et al., *Ann. Biol. Clin.* 51:19-26 (1993); Jonsson et al., *Biotechniques* 11:620-627 (1991); Johnsson et al., *J. Mol. Recognit.* 8:125-131 (1995); and Johnsson et al., *Anal. Biochem.* 198:268-277 (1991).

It is understood that the antibodies of the present invention may be modified, such that they are substantially identical to the antibody polypeptide sequences, or fragments thereof, and still bind the CLL-1 epitopes. Polypeptide sequences are "substantially identical" when optimally aligned using such programs as GAP or BESTFIT using default gap weights, they share at least 80% sequence identity, at least 90% sequence identity, at least 95% sequence identity, at least 96% sequence identity, at least 97% sequence identity, at least 98% sequence identity, or at least 99% sequence identity.

As discussed herein, minor variations in the amino acid sequences of antibodies or antigen-binding regions thereof are contemplated as being encompassed by the present invention, providing that the variations in the amino acid sequence maintain at least 75%, more preferably at least 80%, at least 90%, at least 95%, at least 96%, at least 97%, at least 98% and most preferably at least 99% sequence identity. In particular, conservative amino acid replacements are contemplated. Conservative replacements are those that take place within a family of amino acids that are related in their side chains. Genetically encoded amino acids are generally divided into families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). More preferred families are: (1) aliphatic-hydroxy (serine, threonine); (2) amide-containing (asparagine, glutamine); (3) aliphatic (alanine, valine, leucine, isoleucine); and (4) aromatic (phenylalanine, tryptophan). For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., *Science* 253:164 (1991). Thus, the foregoing examples demonstrate that those of skill in the art can recognize sequence motifs and structural conformations that may be used to define structural and functional domains in accordance with the invention.

The antibodies provided herein may also be generated using peptide analogs of the epitopic determinants disclosed herein, which analogs may consist of non-peptide compounds having properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al., *J. Med. Chem.* 30:1229 (1987).

The term "immune complex" refers to the combination formed when an antibody binds to an epitope on an antigen.

The term "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects.

The term "cytotoxic agent" as used herein refers to a substance that inhibits or prevents the function of cells and/or causes destruction of cells. The term is intended to include radioactive isotopes (e.g., phosphorus-32, copper-67, arsenic-77, rhodium-105, palladium-109, silver-111, tin-121, iodine-125 or 131, holmium-166, lutetium-177, rhenium-186 or 188, iridium-194, gold-199, astatium-211, yttrium-90, samarium-153, or bismuth-212), chemotherapeutic agents, e.g., methotrexate, adriamicin, vinca alkaloids (vincristine, vinblastine, etoposide), doxorubicin, melphalan, mitomycin C, chloramucil, daunorubicin, or other intercalating agents, enzymes and fragments thereof such as nucleolytic enzymes, antibiotics, and toxins such as small molecule toxins or enzymatically active toxins of bacterial (e.g., *Diptheria* toxin, *Pseudomonas* endotoxin and exotoxin, *Staphylococcal* enterotoxin A), fungal (e.g., α-sarcin, restrictocin), plant (e.g., abrin, ricin, modeccin, viscumin, pokeweed anti-viral protein, saporin, gelonin, momoridin, trichosanthin, barley toxin) or animal origin, e.g., cytotoxic RNases, such as extracellular pancreatic RNases; DNase I, including fragments and/or variants thereof, and the various antitumor or anticancer agents disclosed below. Other cytotoxic agents are described below. A tumoricidal agent causes destruction of tumor cells.

The term "immunotherapeutic agent" is used herein to denote an agent that is an immunopotentiator or an immunosuppressant and is useful for treating diseases and disorders including cancer. Such agents include, without limitation, various cytokines and lymphokines, such as a number of interleukins, including IL-1, IL-2, IL-3, IL-4, IL-5, IL-12 and muteins of these molecules; interferons, such as but not limited to IFN-α, IFN-β, IFN-γ and muteins thereof; colony stimulating factors such as GM-CSF and muteins of GM-CSF; tumor necrosis factors, such as TNF-α and TNF-β and muteins of these molecules. Also captured by the term "immunotherapeutic agent" are immunotoxins. By "immunotoxin" is meant an antibody-toxin conjugate intended to destroy specific target cells (e.g., tumor cells) which bear antigens homologous to the antibody. Examples of toxins that are coupled to such antibodies include but are not limited to ricin A chain (RTA), blocked ricin (bIR), saporin (SAP), pokeweed antiviral protein (PAP) and *Pseudomonas* exotoxin (PE), and other toxic compounds, such as radioisotopes and other chemotherapeutic drugs, described further below.

The term "immunoconjugate" refers to the association of an anti-CLL-1 antibody or antigen-binding fragment with another agent, such as a chemotherapeutic agent, a toxin, an immunotherapeutic agent, and the like. In this way, the agent of interest can be targeted directly to cells bearing the CLL-1 antigen. The mode of association between the antibody and the agent of interest is immaterial. Thus, the antibody and agent may be associated through non-covalent interactions such as through electrostatic forces, or by covalent bonds. Various linkers, known in the art, can be employed in order to form the immunoconjugate. Additionally, the immunoconjugate can be provided in the form of a fusion protein that may be expressed from a polynucleotide encoding the immunoconjugate.

As used herein, the terms "label" and "detectable label" refer to a molecule capable of detection, including, but not limited to, radioactive isotopes, fluorescers, semiconductor nanocrystals, chemiluminescers, chromophores, enzymes, enzyme substrates, enzyme cofactors, enzyme inhibitors, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used under the invention include, but are not limited to, horseradish peroxidase (HRP), fluorescein, FITC, rhodamine, dansyl, umbelliferone, dimethyl acridinium ester (DMAE), Texas red, luminol, NADPH and α- or β-galactosidase.

The term "hematologic malignancy" means a cancer of the blood or bone marrow, such as leukemia or lymphoma. Hematologic malignancies are also called hematologic cancer. Hematologic malignancies include, but are not limited to myeloproliferative diseases including acute myelogenous leukemia, chronic myelogenous leukemia, chronic neutrophilic leukemia, chronic eosinophilic leukemia/hypereosinophilic syndrome, chronic idiopathic myelofibrosis, polycythemia vera, essential (or primary) thrombocythemia, unclassifiable myeloproliferative disease; myelodysplastic/myeloproliferative diseases including chronic myelomonocytic leukemia, atypical chronic myelogenous leukemia, juvenile myelomonocytic leukemia; myelodysplastic syndromes including chronic anemia, nonprogressive anemia, refractory anemia, refractory cytopenia, 5q⁻ (5q deletion) syndrome, unclassifiable myelodysplastic syndrome; acute myeloid leukemias, acute myelomonocytic leukemia, acute monocytic leukemia, acute erythoid leukemia, acute megakaryocytic leukemia, acute basophilic leukemia, acute panmyelosis with myelofibrosis; acute biphenotypic leukemias; precursor B-cell neoplasms including precursor B-lymphoblastic leukemia/lymphoma, precursor B-cell acute lymphoblastic leukemia; mature (peripheral) B-cell neoplasms including B-cell acute lymphocytic leukemia, B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma, nodal marginal zone B-cell lymphoma, follicular lymphoma, mantle cell lymphoma, diffuse large B-cell lymphoma, mediastinal large B-cell lymphoma, primary effusion lymphoma, Burkitt lymphoma/Burkitt cell leukemia; precursor T-cell neoplasms including precursor T-lymphoblastic lymphoma/leukemia, precursor T-cell acute lymphoblastic leukemia; mature (peripheral) T-cell neoplasms including T-cell prolymphocytic leukemia, T-cell granular lymphocytic leukemia, aggressive NK-cell leukemia, adult T-cell lymphoma/leukemia, extranodal NK/T-cell lymphoma, enteropathy-type T-cell lymphoma, hepatosplenic gamma-delta T-cell lymphoma, cutaneous T-cell lymphoma, subcutaneous panniculities-like T-cell lymphoma, mycosis fungiodes/Sezary syndrome, anaplastic large-cell lymphoma, peripheral T-cell lymphoma, angioimmunoblastic T-cell lymphoma, anaplastic large-cell lymphoma; Hodgkin lymphomas; mast cell diseases including cutaneous mastocytosis, systemic mast cell disease, mast cell leukemia/sarcoma; macrophage/histiocytic sarcomas; and dendritic cell neoplasms including Langerhans cell histiocytosis, Langerhans cell sarcoma; follicular dendritic cell sarcoma/tumor, dendritic cell sarcoma; myelomas including multiple myeloma, extramedullary plasmacytoma, solitary myeloma; and Waldenstrom macroglobulinemia.

The term "anti-tumor activity" means a reduction in the rate of cell proliferation and hence a decline in growth rate of abnormal cells that arises during therapy. Such activity can be assessed using accepted animal models, such as the Namalwa and Daudi xenograft models of human B-cell lymphoma. See, e.g., Hudson et al., *Leukemia* 12:2029-2033 (1998) for a description of these animal models.

The term "biological sample" as used herein refers to a sample of tissue or fluid isolated from a subject such as, but not limited to, blood, plasma, platelets, serum, fecal matter, urine, bone marrow, bile, spinal fluid, lymph fluid, cerebrospinal fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. The samples detailed above need not necessarily be in the form obtained directly from the source. For example, the sample can be treated prior to use, such as, for example, by heating, centrifuging, etc. prior to analysis.

Various aspects of the invention are described in further detail in the following sections and subsections.

II. The CLL-1 Cell Surface Receptor

Leukocyte functions are regulated by a balance between positive and negative signals delivered by activating and inhibitory receptors. Inhibitory receptors maintain a threshold of activation on the immune system which is overcome by triggering signals in response to pathogenic stimuli. These mechanisms allow leukocytes to distinguish between normal cells and pathologic agents, tumors and grafts. There is some evidence suggesting inhibitory receptor dysfunction may contribute to chronic autoimmune diseases (Ravtek and Lanier, *Science* 290:84-89 (2000); Schultz et al, *Trends Biotechnol.* 15:302-307 (1997)).

One group of inhibitiory receptors belongs to the C-type lectin-like family. CLL-1 is a cell surface receptor characterized by an extracellular region comprising a single C-type lectin-like domain, a single transmembrane domain and a cytoplasmic region containing an ITIM motif (immune tyrosine-based inhibiting motif) and a YXXM motif (Bakker et al, *Cancer Res.* 64:8443-8450 (2004)). Tyrosine phosphorylation at the ITIM motif may serve as a docking site for signaling molecules. YXXM motifs encompass a potential SH2 domain binding site for the p85 subunit of phosphoinositide 3-kinase (PI3K), an enzyme implicated in cellular activation pathways. The YXXM motif may also function as an internalization motif that may be responsible for internalization of the receptor upon antibody-mediated cross-linking. Recent studies purportedly showed that the ITIM motif of CLL-1 in the context of a chimeric receptor was capable of recruiting SHP-1 and SHP-2 tyrosine phosphatases upon receptor cross-linking (Marshall et al *J. Biol. Chem.* 279: 14792-14802 (2004)). Whether the interaction of CLL-1 and its ligand(s) leads to cellular activation or immunomodulation may depend on the level of phosphorylation of both motifs as well as the efficiency of recruitment of SHP-1/2 and p85.

As described in the Examples below, CLL-1 was shown to be selectively expressed in cells of myeloid origin (for example, monocytes), but not in lymphoid cells or other cells of non-myeloid origin. In addition, certain hematological malignancies, including acute myelogenous leukemia (AML), express CLL-1. Further analysis of AML cells revealed that CLL-1 is expressed in AML blasts and CD34$^+$/CD38$^-$ AML stem cells. Taken together, these results indicate that targeting of CLL-1 may be useful to treat AML and other myeloid malignancies and disorders.

In order to further an understanding of the invention, a more detailed discussion is provided below regarding the CLL-1 antigen, antibodies directed against this antigen, chemotherapeutic agents and toxins, compositions, and diagnostic methods.

III. Anti-CLL-1 Antibodies and Antigen-Binding Fragments

A variety of selective binding agents useful for regulating the activity of CLL-1 are provided. These agents include, for instance, antibodies and antigen-binding fragments thereof that contain an antigen binding domain (e.g., single chain antibodies, domain antibodies, immunoadhesions, and polypeptides with an antigen-binding region) that specifically bind to an CLL-1 polypeptide (e.g., a human, rat and/or murine CLL-1 polypeptide).

The present invention provides isolated anti-CLL-1 antibodies that bind to human CLL-1 epitopes. Such antibodies or antigen-binding fragments thereof can be prepared by any one of a number of processes disclosed below, for example, by immunizing an animal with at least a first CLL-1 antigenic composition and selecting from the immunized animal an antibody that substantially cross-reacts with the anti-CLL-1 monoclonal antibodies.

Some of the antibodies and antigen-binding fragments that are provided include (a) one or more light chain (LC) complementary determining regions (CDRs) selected from the group consisting of:
  (i) a LC CDR1 with at least 80% sequence identity to SEQ ID NO: 22 or 34;
  (ii) a LC CDR2 with at least 80% sequence identity to SEQ ID NO: 23 or 35; and (iii) a LC CDR3 with at least 80% sequence identity to SEQ ID NO: 24 or 36;

(b) one or more heavy chain (HC) CDRs selected from the group consisting of:
 (i) a HC CDR1 with at least 80% sequence identity to SEQ ID NO: 16 or 28;
 (ii) a HC CDR2 with at least 80% sequence identity to SEQ ID NO: 17 or 29; and
 (iii) a HC CDR3 with at least 80% sequence identity to SEQ ID NO: 18 or 30; or (c) one or more LC CDRs of (a) and one or more HC CDRs of (b).

Such antibodies or antigen-binding fragments thereof can specifically bind a CLL-1 polypeptide. Certain antibodies or fragments include one, two, three, four, five or six of the foregoing CDRs. In a particular embodiment, the CDRs are arranged as in monoclonal antibodies 21.16 or 1075.7.

The light chain and heavy chains of other antibodies or fragments are as described above but have at least 90% sequence identity to the foregoing sequences. Still other antibodies or antigen-binding fragments thereof have a light chain in which CDR1 has the amino acid sequence as set forth in SEQ ID NO: 22, CDR2 has the amino acid sequence as set forth in SEQ ID NO: 23, and/or CDR3 has the amino acid sequence as set forth in SEQ ID NO: 24. Still other antibodies or antigen-binding fragments thereof have a light chain in which CDR1 has the amino acid sequence as set forth in SEQ ID NO: 34, CDR2 has the amino acid sequence as set forth in SEQ ID NO: 35, and/or CDR3 has the amino acid sequence as set forth in SEQ ID NO: 36. Some antibodies or antigen-binding fragments thereof may also have a heavy chain in which CDR1 has the amino acid sequence as set forth in SEQ ID NO: 16, CDR2 has the amino acid sequence as set forth in SEQ ID NO: 17, and/or CDR3 has the amino acid sequence as set forth in SEQ ID NO: 18. Some antibodies or antigen-binding fragments thereof may also have a heavy chain in which CDR1 has the amino acid sequence as set forth in SEQ ID NO: 28, CDR2 has the amino acid sequence as set forth in SEQ ID NO: 29, and/or CDR3 has the amino acid sequence as set forth in SEQ ID NO: 30.

The antibodies encompassed by the present invention include IgA, $IgG_{1-4}$, IgE, IgM, and IgD antibodies. In a preferred embodiment, the antibody is an IgG and is an $IgG_1$, $IgG_2$, $IgG_3$, or $IgG_4$ subtype. In a particular embodiment, the antibody is an $IgG_1$ isotype. In another preferred embodiment, the anti-CLL-1 antibody is the same class and subclass as antibody 21.16 or 1075.7.

The class and subclass of anti-CLL-1 antibodies may be identified by any method known in the art. In general, the class and subclass of an antibody may be identified using antibodies that are specific for a particular class and subclass of antibody. Such antibodies are available commercially. The class and subclass can be determined by ELISA, Western blot, as well as other techniques. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies.

In another aspect of the invention, the anti-CLL-1 antibody demonstrates both species and molecule selectivity. In one embodiment, the anti-CLL-1 antibody binds to human, cynomologous, rhesus or chimpanzee CLL-1. Following the teachings of the specification, one may determine the species selectivity for the anti-CLL-1 antibody using methods well known in the art. For instance, one may determine species selectivity using Western blot, FACS, ELISA or RIA.

A. Naturally Occurring Antibody Structure

Some of the selective binding agents that are provided herein have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kD) and one full-length "heavy" chain (in certain embodiments, about 50-70 kD). Each individual immunoglobulin chain is composed of several "immunoglobulin (Ig) domains," each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa (κ) and lambda (λ) light chains, and each of these contains one variable domain and one constant domain. Heavy chains are typically classified as mu (μ), delta (δ), gamma (γ), alpha (α), or epsilon (ε) chains and these define the antibody's isotype as IgM, IgD, IgG, IgA, and IgE, respectively. IgG has several subtypes, including, but not limited to, $IgG_1$, $IgG_2$, $IgG_3$, and $IgG_4$. IgM subtypes include $IgM_1$ and $IgM_2$. IgA subtypes include $IgA_1$ and $IgA_2$. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as $C_H1$, $C_H2$, and $C_H3$. The antibodies that are provided can have any of these isotypes and subtypes. In certain embodiments of the invention, the anti-CLL-1 antibodies are of the $IgG_1$ subtype.

In full-length light and heavy chains, the variable and constant regions are joined by a "J" region of about 12 or more amino acids, with the heavy chain also including a "D" region of about 10 or more amino acids. See, e.g., *Fundamental Immunology*, $2^{nd}$ ed., Ch. 7 (Paul, W., ed) 1989, New York: Raven Press (herein incorporated by reference in its entirety for all purposes). The variable regions of each light/heavy chain pair typically form the antigen binding site.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., CLL-1). From N-terminal to C-terminal, naturally occurring light and heavy chain variable regions both typically conform to the following order of these elements: FR1, CDR1, FR2, CDR2, FR3, CDR3 and FR4. A numbering system has been devised for assigning numbers to amino acids that occupy positions in each of these domains. This numbering system is defined in Kabat et al., *Sequences of Proteins of Immunological Interest* (1991, National Institutes of Health Publication No. 91-3242, $5^{th}$ ed., U.S. Department of Health and Human Services, Bethesda, Md.) or Chothia and Lesk, *J. Mol. Biol.* 196:901-917 (1987); Chothia et al., *Nature* 342:878-883 (1989).

As a specific example of such antibodies, the anti-CLL-1 antibody is a monoclonal antibody derived from mice. Exemplary antibodies capable of binding to the aforementioned epitope are the chimeric monoclonal antibodies 21.16 or 1075.7 (see, Examples below), each of which comprises a light chain and a heavy chain.

B. Variable Domains of Antibodies

Also provided are antibodies that comprise a light chain variable region selected from the group consisting of $V_L1$ and $V_L2$ and/or a heavy chain variable region selected from the group consisting of $V_H1$ and $V_H2$ as shown in Table 1 below, and antigen-binding regions, derivatives, muteins and variants of these light and heavy chain variable regions.

Antibodies of this type can generally be designated by the formula "$V_LxV_Hy$," wherein "x" is the number of the light chain variable region and "y" corresponds to the number of the heavy chain variable region as listed in Table 1. In general, x and y are each 1 or 2.

TABLE 1

| Antibody Designation | Abbreviated Name | Chain Type | NT Sequence (SEQ ID NO:) | AA Sequence (SEQ ID NO:) |
|---|---|---|---|---|
| 21.16 | $V_H1$ | Heavy | 4 | 5 |
| 21.16 | $V_L1$ | Light | 6 | 7 |
| 1075.7 | $V_H2$ | Heavy | 8 | 9 |
| 1075.7 | $V_L2$ | Light | 10 | 11 |

Thus, $V_L2V_H1$ refers to an antibody with a light chain variable region domain comprising the amino acid sequence of $V_L2$ and a heavy chain variable region comprising the amino acid sequence of $V_H1$. The antibodies that are provided thus include, but are not limited to, those having the following form: $V_L1V_H1$, $V_L1V_H2$, $V_L2V_H1$ or $V_L2V_H2$. In some instances, the foregoing antibodies include two light chain variable region domains and two heavy chain variable region domains (e.g., $V_L1_2V_H1_2$, etc.).

As a specific example of such antibodies, certain antibodies or antigen-binding fragments thereof comprise the variable region of the light chain or the variable region of the heavy chain of 21.16, wherein the light chain variable region consists of the amino acids shown in SEQ ID NO: 7 and the heavy chain variable region consists of the amino acids shown in SEQ ID NO: 5. In one aspect of this embodiment, the antibody consists of two identical heavy chains and two identical light chains. As another specific example of such antibodies, certain antibodies or antigen-binding fragments thereof comprise the variable region of the light chain or the variable region of the heavy chain of 1075.7, wherein the light chain variable region consists of the amino acids shown in SEQ ID NO: 11 and the heavy chain variable region consists of the amino acids shown in SEQ ID NO: 9. In another aspect of this embodiment, the antibody consists of two identical heavy chains and two identical light chains.

Certain antibodies or antigen-binding fragments thereof comprise a light chain variable domain comprising a sequence of amino acids that differs from the sequence of a light chain variable domain selected from $V_L1$ and $V_L2$ at only 1, 2, 3, 4, 5, 6, 7, 8, 9, 10, 11, 12, 13, 14, or 15 amino acid residues, wherein each such sequence difference is independently either a deletion, insertion, or substitution of one amino acid. The light chain variable region in some antibodies comprises a sequence of amino acids that has at least 70%, at least 75%, at least 80%, at least 85%, at least 90%, at least 95%, at least 96%, at least 97%, at least 98% or at least 99% sequence identity to the amino acid sequences of the light chain variable regions of $V_L1$ or $V_L2$.

Some antibodies or antigen-binding fragments thereof that are provided comprise a heavy chain variable domain comprising a sequence of amino acids that differs from the sequence of a heavy chain variable domain selected from $V_H1$ and $V_H2$ only at 1, 2, 3, 4, 5, 6, 7, 8, 9, 10, 11, 12, 13, 14 or 15 amino acid residues, wherein each such sequence difference is independently either a deletion, insertion, or substitution of one amino acid. The heavy chain variable region in some antibodies comprises a sequence of amino acids that has at least 70%, at least 75%, at least 80%, at least 85%, at least 90%, at least 95%, at least 96%, at least 97%, at least 98% or at least 99% sequence identity to the amino acid sequences of the heavy chain variable region of $V_H1$ or $V_H2$. Still other antibodies or antigen-binding fragments thereof include variant forms of a variant light chain and a variant heavy chain as just described.

C. CDRs of Antibodies

Complementarity determining regions (CDRs) and framework regions (FR) of a given antibody may be identified using the system described by Kabat et al., 1991, supra. Certain antibodies that are disclosed herein comprise one or more amino acid sequences that are identical or have substantial sequence identity to the amino acid sequences of one or more of the CDRs as summarized in Table 2.

TABLE 2

| Antibody Designation | Chain | CDR | NT Sequence (SEQ ID NO:) | AA Sequence (SEQ ID NO:) |
|---|---|---|---|---|
| 21.16 | Heavy | CDR1 | 13 | 16 |
| 21.16 | Heavy | CDR2 | 14 | 17 |
| 21.16 | Heavy | CDR3 | 15 | 18 |
| 21.16 | Light | CDR1 | 19 | 22 |
| 21.16 | Light | CDR2 | 20 | 23 |
| 21.16 | Light | CDR3 | 21 | 24 |
| 1075.7 | Heavy | CDR1 | 25 | 28 |
| 1075.7 | Heavy | CDR2 | 26 | 29 |
| 1075.7 | Heavy | CDR3 | 27 | 30 |
| 1075.7 | Light | CDR1 | 31 | 34 |
| 1075.7 | Light | CDR2 | 32 | 35 |
| 1075.7 | Light | CDR3 | 33 | 36 |

The antibodies and antigen-binding fragments that are provided can each include one, two, three, four, five or six of the CDRs listed above. Certain antibodies have variant forms of the CDRs listed in Table 2, with one or more (e.g., 2, 3, 4, 5 or 6) of the CDRs each having at least 80%, at least 85%, at least 90%, at least 95%, at least 96%, at least 97%, at least 98% or at least 99% sequence identity to a CDR sequence listed in Table 2. For example, the antibody or antigen-binding region can include both a light chain CDR3 and a heavy chain CDR3 that each have at least 80%, at least 85%, at least 90%, at least 95%, at least 96%, at least 97%, at least 98% or at least 99% sequence identity to the light chain CDR3 and heavy chain CDR3, respectively, listed in Table 2. The invention also provides for antibodies that have CDR sequences that differ from the CDR sequences listed in Table 2 such that the amino acid sequence for any given CDR differs from the sequence listed in Table 2 by no more than 1, 2, 3, 4, or 5 amino acid residues. Differences from the listed sequences usually are conservative substitutions (see below).

As a specific example, the antibodies and antigen-binding fragments that are provided may comprise one or more of the following CDR sequences from the 21.16 light chain:

CDR1: amino acids 47 to 56 of SEQ ID NO: 7, which also corresponds to SEQ ID NO: 22 (encoded by nucleotides 70 to 99 of SEQ ID NO: 6 (SEQ ID NO: 19));

CDR2: amino acids 72 to 78 of SEQ ID NO: 7, which also corresponds to SEQ ID NO: 23 (encoded by nucleotides 145 to 165 of SEQ ID NO: 6 (SEQ ID NO: 20)); and CDR3: amino acids 111 to 120 of SEQ ID NO: 7, which also corresponds to SEQ ID NO: 24 (encoded by nucleotides 262 to 291 of SEQ ID NO: 6 (SEQ ID NO: 21)).

Additional antibodies and antigen-binding fragments of the invention may comprise one or more of the following CDR sequences from the 21.16 heavy chain:

CDR1: amino acids 49 to 58 of SEQ ID NO: 5, which also corresponds to SEQ ID NO: 16 (encoded by nucleotides 76 to 105 of SEQ ID NO: 4 (SEQ ID NO: 13));

CDR2: amino acids 73 to 89 of SEQ ID NO: 5, which also corresponds to SEQ ID NO: 17 (encoded by nucleotides 148 to 198 of SEQ ID NO: 4 (SEQ ID NO: 14)); and CDR3: amino acids 122 to 132 of SEQ ID NO: 5, which also corresponds to SEQ ID NO: 18 (encoded by nucleotides 295 to 326 of SEQ ID NO: 4 (SEQ ID NO: 15)).

As another specific example, the antibodies and antigen-binding fragments that are provided may comprise one or more of the following CDR sequences from the 1075.7 light chain:

CDR1: amino acids 47 to 58 of SEQ ID NO: 11, which also corresponds to SEQ ID NO: 34 (encoded by nucleotides 70 to 105 of SEQ ID NO: 10 (SEQ ID NO: 31));

CDR2: amino acids 74 to 80 of SEQ ID NO: 11, which also corresponds to SEQ ID NO: 35 (encoded by nucleotides 151 to 181 of SEQ ID NO: 10 (SEQ ID NO: 32)); and CDR3: amino acids 113 to 121 of SEQ ID NO: 11, which also corresponds to SEQ ID NO: 36 (encoded by nucleotides 268 to 294 of SEQ ID NO: 10 (SEQ ID NO: 33)).

Additional antibodies and antigen-binding fragments of the invention may comprise one or more of the following CDR sequences from the 1075.7 heavy chain:

CDR1: amino acids 49 to 59 of SEQ ID NO: 9, which also corresponds to SEQ ID NO: 28 (encoded by nucleotides 76 to 108 of SEQ ID NO: 8 (SEQ ID NO: 25));

CDR2: amino acids 74 to 89 of SEQ ID NO: 9, which also corresponds to SEQ ID NO: 29 (encoded by nucleotides 151 to 198 of SEQ ID NO: 8 (SEQ ID NO: 26)); and CDR3: amino acids 122 to 135 of SEQ ID NO: 9, which also corresponds to SEQ ID NO: 30 (encoded by nucleotides 295 to 336 of SEQ ID NO: 8 (SEQ ID NO: 27)).

Certain antibodies that are disclosed herein comprise one or more amino acid sequences that comprise one or more CDRs that begin at least one amino acid before (N-terminal to) the beginning amino acid of the CDRs as summarized in Table 2. Yet other antibodies that are disclosed herein comprise one or more amino acid sequences that comprise one or more CDRs that begin at least two, at least three, or at least four amino acids before (N-terminal to) the beginning amino acid of the CDRs as summarized in Table 2. Certain other antibodies that are disclosed herein comprise one or more amino acid sequences that comprise one or more CDRs that end at least one amino acid after (C-terminal to) the last amino acid of the CDRs as summarized in Table 2. Yet other antibodies that are disclosed herein comprise one or more amino acid sequences that comprise one or more CDRs that end at least two, at least three, or at least four amino acids after (C-terminal to) the last amino acid of the CDRs as summarized in Table 2. Other antibodies disclosed herein comprise one or more amino acid sequences that comprise a combination of one or more CDRs with one, two, three or four amino acid differences at the start and/or stop of the CDRs as summarized in Table 2.

Polypeptides comprising one or more of the light or heavy chain CDRs may be produced by using a suitable vector to express the polypeptides in a suitable host cell as described in greater detail below.

The heavy and light chain variable regions and the CDRs that are disclosed in Tables 1 and 2 can be used to prepare any of the various types of antigen-binding fragments that are known in the art including, but not limited to, domain antibodies, Fab fragments, Fab' fragments, F(ab')$_2$ fragments, Fv fragments, single-chain antibodies, and scFvs.

D. Antibodies and Binding Epitopes

When an antibody is said to bind an epitope within specified residues, such as CLL-1, for example, what is meant is that the antibody binds with high affinity to a polypeptide consisting of the specified residues (e.g., a specified segment of CLL-1). Such an antibody does not necessarily contact every residue within CLL-1. Nor does every single amino acid substitution or deletion within CLL-1 necessarily significantly affect binding affinity. Epitope specificity of an antibody can be determined in a variety of ways. One approach, for example, involves testing a collection of overlapping peptides of about 15 amino acids spanning the sequence of CLL-1 and differing in increments of a small number of amino acids (e.g., 3 to 30 amino acids). The peptides are immobilized in separate wells of a microtiter dish. Immobilization can be effected by biotinylating one terminus of the peptides. Optionally, different samples of the same peptide can be biotinylated at the N and C terminus and immobilized in separate wells for purposes of comparison. This is useful for identifying end-specific antibodies. Optionally, additional peptides can be included terminating at a particular amino acid of interest. This approach is useful for identifying end-specific antibodies to internal fragments of CLL-1. An antibody or antigen-binding fragment is screened for binding to each of the various peptides. The epitope is defined as occurring with a segment of amino acids that is common to all peptides to which the antibody shows high affinity binding.

E. Monoclonal Antibodies

The antibodies that are provided herein include monoclonal antibodies that bind to CLL-1. Monoclonal antibodies may be produced using any technique known in the art, e.g., by immortalizing spleen cells harvested from a transgenic or non-transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag41, Sp210-Ag14, FO, NSO/U, MPC-11, MPC11-X45-GTG 1.7 and S194/5XXO Bul; examples of cell lines used in rat fusions include R210.RCY3, Y3-Ag1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a CLL-1 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a CLL-1 polypeptide. Such hybridoma cell lines, and anti-CLL-1 monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as blocking CLL-1 activity or inducing cell killing through ADCC or CMC.

F. Chimeric and Humanized Antibodies

Chimeric and humanized antibodies based upon the foregoing sequences are also provided. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or antigen-binding fragments thereof. Generally, a portion of the heavy chain and/or light chain is identical with, or homologous to, a corresponding sequence in antibodies derived from a particular species or belonging to a particular antibody class or subclass, while the remainder of the chain(s) is/are identical or homologous to a corresponding sequence in antibodies derived from another species or belonging to another antibody class or subclass. For methods relating to chimeric antibodies, see, for example, U.S. Pat. No. 4,816,567; and Morrison et al. *Proc. Natl. Acad. Sci. USA* 81:6851-6855 (1985), which are hereby incorporated by reference. CDR grafting is described, for example, in U.S. Pat. Nos. 6,180,370, 5,693,762, 5,693,761, 5,585,089, and 5,530,101, which are all hereby incorporated by reference for all purposes. Examples of chimeric CLL-1 mAbs are 21.16 and 1075.7.

Generally, the goal of making a chimeric antibody is to create a chimera in which the number of amino acids from the intended patent species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody or corresponding isotype. Preferably, anti-CLL-1 humanized antibodies contain minimal sequence derived from non-human immunoglobulin sequences. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205. In some instances, framework residues of the human immunoglobulin are replaced by corresponding non-human residues (see, for example, U.S. Pat. Nos. 5,585,089; 5,693,761; 5,693,762).

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Struct. Biol.* 2:593-596 (1992); Verhoeyen et al., Science 239:1534-36 (1988)).

In one aspect of the invention, the CDRs of the light and heavy chain variable regions of the antibodies provided herein (see Table 2) are grafted to framework regions (FRs) from antibodies from the same, or a different, phylogenetic species. For example, the CDRs of the light and heavy chain variable regions of the 1075.7 antibody can be grafted to consensus human FRs. To create consensus human FRs, FRs from several human heavy chain or light chain amino acid sequences may be aligned to identify a consensus amino acid sequence. In other embodiments, the FRs of the 1075.7 antibody heavy or light chain are replaced with the FRs from a different heavy chain or light chain. In one aspect of the invention, rare amino acids in the FRs of the heavy and light chains of anti-CLL-1 antibody are not replaced, while the rest of the FR amino acids are replaced. A "rare amino acid" is a specific amino acid that is in a position in which this particular amino acid is not usually found in an FR. Alternatively, the grafted variable regions from the 1075.7 antibody may be used with a constant region that is different from the constant region of 1075.7. In another aspect of this embodiment, the CDRs of the light and heavy chain variable regions of the 21.16 antibody can be used. In other embodiments of the invention, the grafted variable regions are part of a single chain Fv antibody.

In certain embodiments, constant regions from species other than human can be used along with the human variable region(s) to produce hybrid antibodies.

Also encompassed are xenogeneic or modified anti-CLL-1 antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598.

Antibody fragments that retain the ability to recognize the antigen of interest, will also find use herein. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments can contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as Fv. See, e.g., Inbar et al., *Proc. Nat. Acad. Sci. USA* 69:2659-2662 (1972); Hochman et al., *Biochem.* 15:2706-2710 (1976); and Ehrlich et al., *Biochem.* 19:4091-4096 (1980).

A phage-display system can be used to expand antibody molecule populations in vitro. Saiki, et al., *Nature* 324:163 (1986); Scharf et al., *Science* 233:1076 (1986); U.S. Pat. Nos. 4,683,195 and 4,683,202; Yang et al., *J Mol Biol.* 254:392 (1995); Barbas, III et al., *Methods: Comp. Meth Enzymol.* (1995) 8:94; Barbas, III et al., *Proc Natl Acad Sci USA* 88:7978 (1991).

Once generated, the phage display library can be used to improve the immunological binding affinity of the Fab molecules using known techniques. See, e.g., Figini et al., *J. Mol. Biol.* 239:68 (1994). The coding sequences for the heavy and light chain portions of the Fab molecules selected from the phage display library can be isolated or synthesized, and cloned into any suitable vector or replicon for expression. Any suitable expression system can be used, including those described above.

Single chain antibodies are also within the scope of the present invention. A single-chain Fv ("sFv" or "scFv") polypeptide is a covalently linked $V_H$-$V_L$ heterodimer which is expressed from a gene fusion including $V_H$- and $V_L$-encoding genes linked by a peptide-encoding linker. Huston et al., *Proc. Nat. Acad. Sci. USA* 85:5879-5883 (1988). A number of methods have been described to discern and develop chemical structures (linkers) for converting the naturally aggregated, but chemically separated, light and heavy polypeptide chains from an antibody V region into an scFv molecule which will fold into a three-dimensional structure substantially similar to the structure of an antigen-binding site. See, e.g., U.S. Pat. Nos. 5,091,513, 5,132,405 and 4,946,778. The scFv molecules may be produced using methods described in the art. See, e.g., Huston et al., *Proc. Nat. Acad. Sci. USA* 85:5879-5883 (1988); U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art and are well known. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" are also within the scope of the present invention. Minibodies are sFv polypeptide chains that include oligomerization domains at their C-termini, separated from the sFv by a hinge region. Pack et al., *Biochem.* 31:1579-1584 (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al., *Biochem.* 31:1579-1584 (1992); Cumber et al., *J. Immunology* 149B:120-126 (1992).

G. Fully Human Antibodies

Fully human antibodies are also provided. Methods are available for making fully human antibodies specific for a given antigen without exposing human beings to the antigen ("fully human antibodies"). One means for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derivatized mAbs to humans as therapeutic agents.

In one embodiment, human antibodies may be produced in a non-human transgenic animal, e.g., a transgenic mouse capable of producing multiple isotypes of human antibodies to CLL-1 (e.g., IgG, IgA, and/or IgE) by undergoing V-D-J recombination and isotype switching. Accordingly, aspects of the invention include not only antibodies, antibody fragments, and pharmaceutical compositions thereof, but also non-human transgenic animals, B-cells, host cells, and hybridomas which produce anti-CLL-1 monoclonal antibodies. Methods of using the antibodies of the invention to detect a cell expressing CLL-1, either in vivo or in vitro, are also encompassed by the invention. The present invention further encompasses pharmaceutical preparations containing the anti-CLL-1 antibodies or antigen-binding fragments thereof, and methods of treating physiological disorders, e.g., hematopoietic-based cancers, by administering the anti-CLL-1 antibodies or antigen-binding fragments thereof.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al., *Proc. Natl. Acad. Sci. USA* 90:2551-2555 (1993); Jakobovits et al., *Nature* 362:255-258 (1993); Bruggermann et al., *Year in Immunol.* 7:33 (1993). In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, International Patent Application Publication Nos. WO 96/33735 and WO 94/02602, which are hereby incorporated by reference in their entirety. Additional methods relating to transgenic mice for making human antibodies are described in U.S. Pat. Nos. 5,545,807; 6,713,610; 6,673,986; 6,162,963; 6,300,129; 6,255,458; 5,877,397; 5,874,299 and 5,545,806; in International Patent Application Publication Nos. WO 91/10741 and WO 90/04036; and in European Patent Nos. EP 546073B1 and EP 546073A1, all of which are hereby incorporated by reference in their entirety for all purposes.

The transgenic mice described above, referred to herein as "HuMAb" mice, contain a human immunoglobulin gene minilocus that encodes unrearranged human heavy (μ and γ) and κ light chain immunoglobulin sequences, together with targeted mutations that inactivate the endogenous μ and κ chain loci (Lonberg et al., *Nature* 368:856-859 (1994)). Accordingly, the mice exhibit reduced expression of mouse IgM or κ chains and in response to immunization, the introduced human heavy and light chain transgenes undergo class switching and somatic mutation to generate high affinity human IgG κ monoclonal antibodies (Lonberg et al., supra; Lonberg and Huszar, *Intern. Ref. Immunol.* 13:65-93 (1995); Harding and Lonberg, *Ann. N.Y. Acad. Sci.* 764:536-546 (1995)). The preparation of HuMAb mice is described in detail in Taylor et al., *Nucl. Acids Res.* 20:6287-6295 (1992); Chen et al., *Int Immunol.* 5:647-656 (1993); Tuaillon et al., *J. Immunol.* 152:2912-2920 (1994); Lonberg et al., supra; Lonberg, *Handbook of Exp. Pharmacol.* 113:49-101 (1994); Taylor et al., *Int. Immunol.* 6:579-591 (1994); Lonberg and Huszar, *Intern. Ref. Immunol.* 13:65-93 (1995); Harding and Lonberg, *Ann. N.Y. Acad. Sci.* 764:536-546 (1995); Fishwild et al., *Nat. Biotechnol.* 14:845-851 (1996); the foregoing references are herein incorporated by reference in their entirety for all purposes. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; as well as International Patent Application Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., *Nat. Genetics* 15:146-156 (1997), which are herein incorporated by reference. For example, the HCo7 and HCo12 transgenic mice strains can be used to generate human anti-CLL-1 antibodies.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., *J. Mol. Biol.* 227:381 (1991); and Marks et al., *J. Mol. Biol.* 222:581 (1991)). Phage-display techniques mimic immune selection through the display of antibody repertoires on the surface of filamentous bacteriophage, and subsequent selection of phage by their binding to an antigen of choice. One such technique is described in International Patent Application Publication No. WO 99/10494 (herein incorporated by reference), which describes the isolation of high affinity and functional agonistic antibodies for MPL- and msk-receptors using such an approach.

H. Bispecific or Bifunctional Antibodies

The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai and Lachmann, *Clin. Exp. Immmunol.* 79:315-321 (1990); Kostelny et al., *J. Immunol.* 148:1547-1553 (1992).

I. Various Other Forms

Some of the antibodies or antigen-binding fragments that are provided are variant forms of the antibodies and fragments disclosed above (e.g., those having the sequences listed in Tables 1 and 2). For instance, some of the antibodies or antigen-binding fragments are ones having one or more conservative amino acid substitutions in one or more of the heavy or light chains, variable regions or CDRs listed in Tables 1 and 2.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the classes for a member from another class. Such substituted residues may be introduced into regions of the antibody that are homologous with human antibodies, or into the non-homologous regions of the molecule.

In making such changes, according to certain embodiments, the hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, for example, Kyte et al., *J. Mol. Biol.* 157:105-131 (1982)). It is known that certain amino acids may be substituted for other amino acid sharing a similar hydropathic index or score and still retain a similar biological activity. In making changes based upon the hydropathic index, in certain embodiments, the substitution of amino acids whose hydropathic indices are within ±2 is included. In some aspects of the invention, those which are within ±1 are included, and in other aspects of the invention, those within ±0.5 are included).

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, in certain embodiments, the substitution of amino acids whose hydrophilicity values are within ±2 are included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in Table 3.

TABLE 3

| Original Residues | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, Gln, Asn, 1,4 diamine-butryic acid |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for CLL-1 binding, ADCC and/or CDC activity (see Examples below). Information gathered from such routine experiments may be used by one skilled in the art to readily determine the amino acid positions where further substitutions should be avoided either alone or in combination with other mutations.

A number of scientific publications have been devoted to the prediction of secondary structure. See, Moult, *Curr. Op. Biotech* 7:422-427 (1996); Chou et al., *Biochemistry* 13:222-245 (1974); Chou et al., *Biochemistry* 13:211-222 (1974); Chou et al., *Adv. Enzymol. Relat. Areas Mol. Biol.* 47:45-148 (1978); Chou et al., *Ann. Rev. Biochem.* 47:251-276 (1979); and Chou et al., *Biophys J.* 26:367-384 (1979). Moreover, computer programs are currently available to assist with predicting secondary structure. One method of predicting secondary structure is based upon homology modeling. For example, two polypeptides or proteins that have a sequence identity of greater than 30%, or similarity of greater than 40% often have similar structural topologies. The growth of the protein structural database (PDB) has provided enhanced predictability of secondary structure, including the potential number of folds within a polypeptide's or protein's structure. See, Holm et al., *Nucl. Acids Res.* 27:244-247 (1999). It has been suggested (Brenner et al., *Curr. Op. Struct. Biol.* 7:369-376 (1997)) that there are a limited number of folds in a given polypeptide or protein and that once a critical number of structures have been resolved, structural prediction will become dramatically more accurate.

Additional methods of predicting secondary structure include "threading" (Jones, *Curr. Opin. Struct. Biol.* 7:377-87 (1997); Sippl et al., *Structure* 4:15-19 (1996)), "profile analysis" (Bowie et al., *Science* 253:164-170 (1991); Gribskov et al., *Proc. Natl. Acad. Sci. USA* 84:4355-4358 (1987)), and "evolutionary linkage" (See, Holm, 1999, supra; and Brenner, 1997, supra).

In some embodiments of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts. In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in *Proteins, Structures and Molecular Principles* (Creighton, Ed.), 1984, W.H. New York: Freeman and Company; *Introduction to Protein Structure* (Brandon and Tooze, eds.), 1991 New York: Garland Publishing; and Thornton et al., *Nature* 354:105 (1991), each of which is incorporated herein by reference in its entirety for all purposes.

The invention also encompasses glycosylation variants of the anti-CLL-1 antibodies and antigen-binding fragments thereof wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked glycosylation sites are created. Antibodies typically have a N-linked glycosylation site in the Fc region.

Additional preferred antibody variants include cysteine variants wherein one or more cysteine residues in the parent or native amino acid sequence are deleted from or substituted with another amino acid (e.g., serine). Cysteine variants are useful, inter alia, when antibodies must be refolded into a biologically active conformation. Cysteine variants may have fewer cysteine residues than the native antibody, and typically have an even number to minimize interactions resulting from unpaired cysteines.

The heavy and light chains, variable region domains and CDRs that are disclosed can be used to prepare polypeptides that contain an antigen-binding fragment that can specifically bind to a CLL-1 molecule. For example, one or more of the CDRs listed in Table 2 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., an CLL-1 polypeptide or epitope thereof).

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, *Adv. Drug Res.* 15:29 (1986); Veber and Freidiner, *TINS* p. 392 (1985); and Evans et al., *J. Med. Chem.* 30:1229 (1987), which are incorporated herein by reference in their entirety for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as the ability to bind CLL-1, but have one or more peptide linkages optionally replaced by a linkage selected from: —CH$_2$NH—, —CH$_2$S—, —CH$_2$—CH$_2$—, —CH=CH— (cis and trans), —COCH$_2$—, —CH(OH)CH$_2$—, and —CH$_2$SO— by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference), for example, by adding internal cysteine residues capable of forming intramolecular disulfide bridges which cyclize the peptide.

Derivatives of the antibodies and antigen binding fragments that are described herein are also provided. The derivatized antibody or fragment may comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead [such as a magnetic or electrodense (e.g., gold) bead], or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly (n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of anti-CLL-1 antibodies, or antigen-binding fragments thereof, with other proteins or polypeptides, such as by expression of recombinant fusion proteins comprising heterologous polypeptides fused to the N-terminus or C-terminus of an anti-CLL-1 antibody polypeptide. For example, the conjugated peptide may be a heterologous signal (or leader) polypeptide, e.g., the yeast alpha-factor leader, or a peptide such as an epitope tag (e.g., V5-His). Anti-CLL-1 antibody-containing fusion proteins may comprise peptides added to facilitate purification or identification of the anti-CLL-1 antibody (e.g., poly-His). An anti-CLL-1 antibody polypeptide also can be linked to the FLAG® (Sigma-Aldrich, St. Louis, Mo.) peptide as described in Hopp et al., *Bio/Technology* 6:1204 (1988), and U.S. Pat. No. 5,011,912. The FLAG® peptide is highly antigenic and provides an epitope reversibly bound by a specific monoclonal antibody enabling reversibly rapid assay and facile purification of expressed recombinant protein. Reagents useful for preparing fusion proteins in which the FLAG® peptide is fused to a given polypeptide are commercially available (Sigma, St. Louis, Mo., USA).

Oligomers that contain one or more anti-CLL-1 antibody polypeptides may be employed as CLL-1 antagonists. Oligomers may be in the form of covalently-linked or non-covalently linked dimers, trimers, or higher oligomers. Oligomers comprising two or more anti-CLL-1 antibody polypeptides are contemplated for use, with one example being a homodimer. Other oligomers include heterodimers, homotrimers, heterotrimers, homotetramers, heterotetramers, etc.

One embodiment is directed to oligomers comprising multiple anti-CLL-1 antibody polypeptides joined via covalent or non-covalent interactions between peptide moieties fused to the anti-CLL-1 antibody polypeptides. Such peptides may be peptide linkers (spacers), or peptides that have the property of promoting oligomerization. Leucine zippers and certain polypeptides derived from antibodies are among the peptides that can promote oligomerization of anti-CLL-1 antibody polypeptides attached thereto, as described in more detail below.

In particular embodiments, the oligomers comprise from two to four anti-CLL-1 polypeptides. The anti-CLL-1 antibody moieties of the oligomer may be in any of the forms described above, e.g., variants or fragments. Preferably, the oligomers comprise anti-CLL-1 antibody polypeptides that have CLL-1 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., *Proc. Natl. Acad. Sci. USA* 88:10535 (1991); Byrn et al., *Nature* 344:677 (1990); and Hollenbaugh et al., 1992 "Construction of Immunoglobulin Fusion Proteins," in *Current Protocols in Immunology*, Suppl 4, pages 10.19.1-10.19.11.

One embodiment of the present invention is directed to a dimer comprising two fusion proteins created by fusing an CLL-1 binding fragment of an anti-CLL-1 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in International Patent Application Publication No. WO 93/10151 and U.S. Pat. Nos. 5,426,048 and 5,262,522 (each of which is herein incorporated by reference), is a single chain polypeptide extending from the N-terminal hinge region to the native C-terminus of the Fc region of a human $IgG_1$ antibody. Another useful Fc polypeptide is the Fc mutein described in U.S. Pat. No. 5,457,035 and in Baum et al., *EMBO J.* 13:3992-4001 (1994). The amino acid sequence of this mutein is identical to that of the native Fc sequence presented in WO 93/10151, except that amino acid 19 has been changed from Leu to Glu, and amino acid 22 has been changed from Gly to Ala. The mutein exhibits reduced affinity for Fc receptors.

In other embodiments, the variable portion of the heavy and/or light chains of an anti-CLL-1 antibody such as disclosed herein may be substituted for the variable portion of an antibody heavy and/or light chain.

Alternatively, the oligomer is a fusion protein comprising multiple anti-CLL-1 antibody polypeptides, with or without peptide linkers (spacer peptides). Among the suitable peptide linkers are those described in U.S. Pat. Nos. 4,751,180 and 4,935,233.

Another method for preparing oligomeric anti-CLL-1 antibody derivatives involves use of a leucine zipper. Leucine zipper domains are peptides that promote oligomerization of the proteins in which they are found. Leucine zippers were originally identified in several DNA-binding proteins (Landschulz et al., *Science* 240:1759 (1988)), and have since been found in a variety of different proteins. Among the known leucine zippers are naturally occurring peptides and derivatives thereof that dimerize or trimerize. Examples of leucine zipper domains suitable for producing soluble oligomeric proteins are described in International Patent Application Publication No. WO 94/10308, and the leucine zipper derived from lung surfactant protein D (SPD) described in Hoppe et al., *FEBS Lett.* 344:191 (1994), hereby incorporated by reference. The use of a modified leucine zipper that allows for stable trimerization of a heterologous protein fused thereto is described in Fanslow et al., *Semin. Immunol.* 6:267-78 (1994). In one approach, recombinant fusion proteins comprising an anti-CLL-1 antibody fragment or derivative fused to a leucine zipper peptide are expressed in suitable host cells, and the soluble anti-CLL-1 antibody fragments or derivatives that form are recovered from the culture supernatant.

Some antibodies that are provided have a binding affinity ($k_a$) for CLL-1 of at least $10^4$ or $10^5$ M$^{-1}$sec$^{-1}$ measured, for instance, as described in the examples below. Other antibodies have a $k_a$ of at least $10^6$, $10^7$, $10^8$ or $10^9$ M$^{-1}$sec$^{-1}$. Certain antibodies that are provided have a low disassociation rate. Some antibodies, for instance, have a $k_{off}$ of $1 \times 10^{-4}$ s$^{-1}$, $1 \times 10^{-5}$ s$^{-1}$ or lower. In another embodiment, the $k_{off}$ is the same as an antibody having the following combinations of variable region domains $V_L1$ $V_H1$, $V_L1V_H2$, $V_L2V_H1$ or $V_L2V_H2$.

In another aspect, the present invention provides an anti-CLL-1 antibody or antigen-binding fragment having a half-life of at least one day in vitro or in vivo (e.g., when administered to a human subject). In one embodiment, the antibody or antigen-binding fragment has a half-life of at least three days. In another embodiment, the antibody or antigen-binding fragment has a half-life of four days or longer. In another embodiment, the antibody or antigen-binding fragment has a half life of eight days or longer. In another embodiment, the antibody or antigen-binding fragment is derivatized or modified such that it has a longer half-life as compared to the underivatized or unmodified antibody. In another embodiment, the antibody contains point mutations to increase serum half life, such as described in International Patent Application Publication No. WO 00/09560, which is herein incorporated by reference.

J. Immunoconjugates

The invention also pertains to immunoconjugates, or antibody-drug conjugates (ADC), comprising an antibody or antigen-binding fragment thereof conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In one embodiment of the invention, an anti-CLL-1 antibody may be conjugated to various therapeutic substances in order to target the CLL-1 antigen. Examples of conjugated agents include, but are not limited to, metal chelate complexes, drugs, toxins and other effector molecules, such as cytokines, lymphokines, chemokines, immunomodulators, radiosensitizers, asparaginase, carboranes and radioactive halogens.

Additionally, enzymes useful for activating a prodrug or increasing the target-specific toxicity of a drug can be conjugated to the antibodies. Such substances are described in further detail below.

The use of antibody-drug conjugates for the local delivery of cytotoxic or cytostatic agents, i.e. drugs to kill or inhibit tumor cells in the treatment of cancer (Syrigos and Epenetos, *Anticancer Res.* 19:605-614 (1999); Niculescu-Duvaz and Springer, *Adv. Drg. Del. Rev.* 26:151-172 (1997); U.S. Pat. No. 4,975,278) theoretically allows targeted delivery of the drug moiety to tumors, and intracellular accumulation therein, where systematic administration of these unconjugated drug agents may result in unacceptable levels of toxicity to normal cells as well as the tumor cells sought to be eliminated (Baldwin et al., *Lancet* 1:603-5 (1986); Thorpe, (1985) "Antibody Carriers of Cytotoxic Agents in Cancer Therapy: A Review," In: *Monoclonal Antibodies '84: Biological and Clinical Applications*, A. Pincera et al., (eds.) pp. 475-506). Maximal efficacy with minimal toxicity is sought thereby. Both polyclonal antibodies and monoclonal antibodies have been reported as useful in these strategies (Rowland et al., *Cancer Immunol. Immunother.* 21:183-87 (1986)). Drugs used in these methods include danuomycin, doxorubicin, methotrexate and vindesine (Rowland et al., (1986) supra). Toxins used in antibody-toxin conjugates include bacterial toxins such as diphtheria toxin, plant toxins such as ricin, small molecule toxins such as geldamanycin (Mandler et al., *J. Nat. Cancer Inst.* 92:1573-1581 (2000); Mandler et al., *Bioorganic Med. Chem. Lett.* 10:1025-1028 (2000); Mandler et al., *Bioconjugate Chem.* 13:786-791 (2002)), maytansinoids (European Patent No. EP 1391213; Liu et al., *Proc. Natl. Acad. Sci. USA* 93:8618-8623 (1996)), and calicheamicin (Lode et al., *Cancer Res.* 58:2928 (1998); Rinman et al., *Cancer Res.* 53:3336-3342 (1993)). The toxins may effect their cytotoxin and cytostatic effects by mechanisms including tubulin binding, DNA binding, or topoisomerase inhibition. Some cytotoxic drugs tend to be inactive or less active when conjugated to large antibodies or protein receptor ligands.

The anti-CLL-1 antibodies and antigen-binding fragments thereof may be used in combination with various chemotherapeutic agents, toxins and regimens. The agents and/or toxins can either be administered before, after or concurrently with the antibodies disclosed herein. Alternatively, if appropriate, the agents and toxins can be conjugated to the antibodies of the invention to target the agent directly to tumor cells.

A "chemotherapeutic agent" is a chemical compound or combination of compounds useful in the treatment of cancer. Examples of chemotherapeutic agents include alkylating agents such as thiotepa and cyclosphosphamide (CYTOXAN®, Mead Johnson and Co., Evansville, Ind.); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above.

Other useful chemotherapeutic agents include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON®, GTx, Inc., Memphis, Tenn.); and anti-androgens such as flutamide, nilutamide, bicalutamide, leuprolide, and goserelin; and pharmaceutically acceptable salts, acids or derivatives of any of the above.

Also useful are the chemotherapeutic regimens known as CHOP (a combination of cyclophosphamide, doxorubicin, vincristine and prednisone) as well as the use of the constituents of CHOP either alone or in various combinations such as CO, CH, CP, COP, CHO, CHP, HO, HP, HOP, OP, etc.; CHOP and bleomycin (CHOP-BLEO); cyclophosphamide and fludarabine; cyclophosphamide, mitoxantrone, prednisone and vincristine; cyclophosphamide, dexamethasone, doxorubicin and vincristine (CAVD); CAV; cyclophosphamide, doxorubicin and prednisone; cyclophosphamide, mitoxantrone, prednisone and vincristine (CNOP); cyclophosphamide, methotrexate, leucovorin and cytarabine (COMLA); cyclophosphamide, dexamethasone, doxorubicin and prednisone; cylophosphamide, prednisone, procarbazine and vincristine (COPP); cylophosphamide, prednisone and vincristine (COP and CVP-1); cyclophosphamide and mitoxantrone; etoposide; mitoxantrone, ifosfamide and etoposide (MIV); cytarabine; methylprednisolone and cisplatin (ESHAP); methylprednisolone, cytarabine and cisplatin (ESAP); methotrexate, leucovorin, doxorubicin, cyclophosphamide, vincristine, bleomycin and prednisone (MACOP-B); methotrexate, bleomycin, doxorubicin, cyclophosphamide, vincristine, and dexamethasone (m-BACOD); prednisone, cyclophosphamide, etoposide, cytarabine, bleomycin, vincristine, methotrexate and leucovorin (PROMACE-CYTABOM); etoposide, cyclophosphamide, vincristine, prednisone and bleomycin (VA-COP-B); fludarabine and mitoxantrone; cisplatine, cytarabine and etoposide; desamethasone, fludarabine and mitoxantrone; chlorambucil and prednisone; busulfan and fludarabine; ICE; DVP; ATRA; Idarubicin, hoelzer chemotherapy regime; La La chemotherapy regime; ABVD; CEOP; 2-CdA; FLAG and IDA (with or without subsequent G-CSF treatment); VAD; M and P; C-Weekly; ABCM; MOPP; cisplatin, cytarabine and dexamethasone (DHAP), as well as the additional known chemotherapeutic regimens.

Enzymatically active toxins and fragments thereof that can be used include diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca mericana* proteins (PAPI, PAPII, and PAP-S), *Momordica charantia* inhibitor, curcin, crotin, *sapaonaria officinalis* inhibitor, gelonin, mitegellin, restrictocin, phenomycin, neomycin, and the tricothecenes. See, for example, International Patent Application Publication No. WO 93/21232.

A variety of radionuclides are available for the production of radioconjugated antibodies. Goodwin and Meares, *Cancer Supplement* 80:2675-2680 (1997) have described the use of yttrium-90-labeled monoclonal antibodies in various strategies to maximize the dose to tumor while limiting normal tissue toxicity. Other known cytotoxic radionuclides include, but are not limited to phosphorus-32, copper-67, arsenic-77, rhodium-105, palladium-109, silver-111, tin-121, iodine-125 or 131, holmium-166, lutetium-177, rhenium-186 or 188, iridium-194, gold-199, astatium-211, yttrium-90, samarium-153, or bismuth-212, all of which can be used to label antibodies directed against the CLL-1 antigen for the treatment of cancer. When the conjugate is used for detection, it may comprise a radioactive atom for scintigraphic studies, for example technetium-99m or iodine-123, or a spin label for nuclear magnetic resonance (NMR) imaging (also known as magnetic resonance imaging (MRI)), such as iodine-123, iodine-131, iodine-111, fluorine-19, carbon-13, nitrogen-15, oxygen-17, gadolinium, manganese or iron.

The anti-CLL-1 antibodies or antigen-binding fragments thereof can be conjugated to radionuclides using an indirect labeling or indirect labeling approach. In one aspect, the anti-CLL-1 antibody is labeled using an "indirect labeling" or "indirect labeling approach" where a chelating agent is covalently attached to an antibody and at least one radionuclide is inserted into the chelating agent. See, for example, the chelating agents and radionuclides described in Srivastava and Mease, *Int. J. Rad. Appl. Instrum. B*. 18:589-603 (1991). Alternatively, the anti-CLL-1 antibody may be labeled using "direct labeling" or a "direct labeling approach", where a label, such as a radionuclide is covalently attached directly to an antibody (typically via an amino acid residue). For example, the peptide may be biosynthesized or may be synthesized by chemical amino acid synthesis using amino acid precursors involving, for example, fluorine-19 in place of hydrogen. Labels such as technetium-99m, iodine-123, rhenium-186, rhenium-188, and indium-111 can be attached via a cysteine residue in the peptide. Yttrium-90 can be attached via a lysine residue. The iodogen method (Franker et al., *Biochem. Biophys. Res. Commun.* 80:49-57 (1978)) can be used to incorporate iodine-123. "Monoclonal Antibodies in Immunoscintigraphy" (Chantal, CRC Press, 1989, which is herein incorporated by reference in its entirety) describes other methods in detail.

Conjugates of an anti-CLL-1 antibody and a cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)hexanediamine), bis-diazonium derivatives (such as bos(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). $^{14}$C-labeled 1-isothiocyanatobenzyl-3-methyldiethylene triaminepentaacetic acid (MX-DTPA) is an exemplary chelating agent for conjugation of radionucleotide to the antibody. See, International Patent Application Publication No. WO 94/11026.

In a further embodiment, the anti-CLL-1 antibody or antigen-binding fragment thereof is linked to an enzyme that converts a prodrug into a cytotoxic drug. The enzymes cleave the non-toxic "prodrug" into the toxic "drug", which leads to tumor cell death. Suitable prodrug enzymes include thymidine kinase (TK), xanthine-guanine phosphoribosyltransferase (GPT) gene from *E. coli* or *E. coli* cytosine deaminase (CD), or hypoxanthine phosphoribosyl transferase (HPRT). Additional representative examples of enzymes and associated prodrug molecules include alkaline phosphatase and various toxic phosphorylated compounds such as phenolmustard phosphate, doxorubicin phosphate, mitomycin phosphate and etoposide phosphate; $\beta$-galactosidase and N-[4-($\beta$-D-galactopyranosyl)benyloxycarbonyl]-daunorubicin; azoreductase and azobenzene mustards; $\beta$-glucosidase and amygdalin; $\beta$-glucuronidase and phenolmustard-glucuronide and epirubicin-glucuronide; carboxypeptidase A and methotrexate-alanine; cytochrome P450 and cyclophosphamide or ifosfamide; DT diaphorase and 5-(aziridine-1-yl)-2,4,dinitrobenzamide (CB1954) (Cobb et al., *Biochem. Pharmacol* 18:1519 (1969), Knox et al., *Cancer Metastasis Rev.* 12:195 (1993)); $\beta$-glutamyl transferase and $\beta$-glutamyl p-phenylenediamine mustard; nitroreductase and CB1954 or derivatives of 4-nitrobenzyloxycarbonyl; glucose oxidase and glucose; xanthine oxidase and hypoxanthine; and plasmin and peptidyl-p-phenylenediamine-mustard.

Conjugates of an antibody and one or more small molecule toxins, such as calcheamicin, maytansinoids, a trichothecene, and CC1065, and the derivatives of these toxins that have toxin activity, are also contemplated herein.

Additionally, immunoconjugates formed between an antibody and a compound with nucleolytic activity (e.g., a ribonuclease or a DNA endonuclease such as deoxyribonuclease; DNase) are contemplated herein.

Additionally, the anti-CLL-1 antibodies may be attached to various labels in order to screen biological samples such as blood, tissues and/or tumors for the presence or absence of the proteins, as an indication of cancer, as described further below.

K. Preparation of Antibody Drug Conjugates

In the antibody drug conjugates (ADC) of the invention, an antibody (Ab) is conjugated to one or more drug moieties (D), e.g., about 1 to about 20 drug moieties per antibody, through a linker (L). The ADC of Formula I (see below) may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D;

and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_P \quad (I)$$

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiolthreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium metaperiodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, *Bioconjugate Chem.* 3:138-146 (1992); U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine, carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such as streptavidin) for utilization in tumor or cancer cell pre-targeting" wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionuclotide).

IV. CLL-1 Nucleic Acids

A. Nucleic Acids

Polynucleotide sequences encoding the antibodies and immunoreactive fragments thereof, described above, are readily obtained using standard techniques, well known in the art, such as those techniques described above with respect to the recombinant production of the CLL-1 antigens.

Nucleic acids that encode one or both chains of an anti-CLL-1 antibody, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 175, 200, 250, 300, 350, 400, 450, 500, 750, 1000, 1500, 3000, 5000 or more nucleotides in length, and/or can comprise one or more additional sequences, for example, regulatory sequences, and/or be a part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids that encode the epitope to which certain of the antibodies provided herein are also provided. Nucleic acids encoding fusion proteins that include these peptides are also provided.

DNA encoding antibody polypeptides (e.g., heavy or light chain, variable domain only, or full-length) may be isolated from B cells of mice that have been immunized with CLL-1 or an immunogenic fragment thereof. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Exemplary nucleic acids that encode the light and heavy chains, variable regions and CDRs of the antibodies and antigen-binding fragments are provided in Tables 1 and 2 above. Due to the degeneracy of the genetic code, each of the polypeptide sequences listed in Tables 1 and 2 is also encoded by a large number of other nucleic acid sequences besides those listed in Tables 1 and 2. The present invention provides each degenerate nucleotide sequence encoding each anti-CLL-1 antibody or antigen-binding fragment thereof.

Nucleic acid molecules encoding anti-CLL-1 antibodies are provided. In one embodiment, the nucleic acid molecule encodes a heavy and/or light chain of an anti-CLL-1 immunoglobulin. In a preferred embodiment, a single nucleic acid molecule encodes a heavy chain of an anti-CLL-1 immunoglobulin and another nucleic acid molecule encodes the light chain of an anti-CLL-1 immunoglobulin. In a more preferred embodiment, the encoded immunoglobulin is a human immunoglobulin, preferably a human IgG. The encoded light chain may be a λ chain or a κ chain.

Provided herein are nucleic acid molecules comprising a nucleic acid sequence that encodes the amino acid sequence of the variable region of the light chain ($V_L$) of 21.16 or 1075.7. Also provided are nucleic acid molecules comprising a nucleic acid sequence that encodes the amino acid sequence of one or more of the CDRs of any one of the light chains of 21.16 or 1075.7. In a preferred embodiment, the nucleic acid molecule comprises a nucleic acid sequence that encodes the amino acid sequence of all of the CDRs of any one of the light chains of 21.16 or 1075.7. In another embodiment, the nucleic acid molecule comprises a nucleic acid sequence that encodes the amino acid sequence of one of SEQ ID NO: 7 or 11 or comprises a nucleic acid sequence of one of SEQ ID NO: 6 or 10. In another preferred embodiment, the nucleic acid molecule comprises a nucleic acid sequence that encodes the amino acid sequence of one or more of the CDRs of any one of SEQ ID NO: 7 (i.e., SEQ ID NO: 22, 23 or 24) or SEQ ID NO: 11 (i.e., SEQ ID NO: 34, 35 or 36) or comprises a nucleic acid sequence of one or more of the CDRs of any one of SEQ ID NO: 6 (i.e., SEQ ID NO: 19, 20 or 21) or SEQ ID NO: 10 (i.e., SEQ ID NO: 31, 32 or 33). In a more preferred embodiment, the nucleic acid molecule comprises a nucleic acid sequence that encodes the amino acid sequence of all of the CDRs of any one of SEQ ID NO: 7 (i.e., SEQ ID NO: 22, 23 or 24) or SEQ ID NO: 11 (i.e., SEQ ID NO: 34, 35 or 36) or comprises a nucleic acid sequence of all the CDRs of any one of SEQ ID NO: 6 (i.e., SEQ ID NO: 19, 20 or 21) or SEQ ID NO: 10 (i.e., SEQ ID NO: 31, 32 or 33).

The invention also provides nucleic acid molecules that encode an amino acid sequence of a $V_L$ that has an amino acid sequence that is at least 70%, at least 75%, at least 80%, at least 85%, at least 90%, at least 95%, at least 96%, at least 97%, at least 98%, or at least 99% identical to a $V_L$ described above, particularly to a $V_L$ that comprises an amino acid sequence of one of SEQ ID NO: 7 or 11. The invention also provides a nucleic acid sequence that is at least 70%, at least 75%, at least 80%, at least 85%, at least 90%, at least 95%, at least 96%, at least 97%, at least 98%, or at least 99% identical to a nucleic acid sequence of one of SEQ ID NO: 6 or 10. In another embodiment, the invention provides a nucleic acid molecule encoding a $V_L$ that hybridizes under stringent conditions to a nucleic acid molecule encoding a $V_L$ as described above, particularly a nucleic acid molecule that comprises a nucleic acid sequence encoding an amino acid sequence of SEQ ID NO: 7 or 11. The invention also provides a nucleic acid sequence encoding a $V_L$ 0 that hybridizes under stringent conditions to a nucleic acid molecule comprising a nucleic acid sequence of one of SEQ ID NO: 6 or 10.

The invention also provides a nucleic acid molecule encoding the variable region of the heavy chain ($V_H$) of 21.16 or 1075.7. In one embodiment, the nucleic acid molecule comprises a nucleic acid sequence that encodes the amino acid sequence of the $V_H$ of 21.16 or 1075.7. In another embodiment, the nucleic acid molecule comprises a nucleic acid sequence that encodes the amino acid sequence of one or more of the CDRs of the heavy chain of 21.16 or 1075.7. In a preferred embodiment, the nucleic acid molecule comprises a nucleic acid sequence that encodes the amino acid sequences of all of the CDRs of the heavy chain of 21.16 or 1075.7. In another preferred embodiment, the nucleic acid molecule comprises a nucleic acid sequence that encodes the amino acid sequence of one of SEQ ID NO: 5 or 9 or that comprises a nucleic acid sequence of one of SEQ ID NO: 4 or 8. In another preferred embodiment, the nucleic acid molecule comprises a nucleic acid sequence that encodes the amino acid sequence of one or more of the CDRs of any one of SEQ ID NO: 5 (i.e., SEQ ID NO: 16, 17 or 18) or SEQ ID NO: 9 (i.e., SEQ ID NO: 28, 29 or 30) or comprises a nucleic acid sequence of one or more of the CDRs of any one of SEQ ID NO: 4 (i.e., SEQ ID NO: 13, 14 or 15) or SEQ ID NO: 8 (i.e., SEQ ID NO: 25, 26 or 27). In a preferred embodiment, the nucleic acid molecule comprises a nucleic acid sequence that encodes the amino acid sequences of all of the CDRs of any one of SEQ ID NO: 5 (i.e., SEQ ID NO: 16, 17 or 18) or SEQ ID NO: 9 (i.e., SEQ ID NO: 28, 29 or 30) or comprises a nucleic acid sequence of all of the CDRs for any one of SEQ ID NO: 4 (i.e., SEQ ID NO: 13, 14 or 15) or SEQ ID NO: 8 (i.e., SEQ ID NO: 25, 26 or 27).

In another embodiment, the nucleic acid molecule encodes an amino acid sequence of a $V_H$ that is at least 70%, at least 75%, at least 80%, at least 85%, at least 90%, at least 95%, at least 96%, at least 97%, at least 98%, or at least 99% identical to one of the amino acid sequences encoding a $V_H$ as described immediately above, particularly to a $V_H$ that comprises an amino acid sequence of one of SEQ ID NO: 5 or 9. In another embodiment, the nucleic acid molecule encoding a $V_H$ is one that hybridizes under stringent conditions to a nucleic acid sequence encoding a $V_H$ as described above, particularly to a $V_H$ that comprises an amino acid sequence of one of SEQ ID NO: 5 or 9. The invention also provides a nucleic acid sequence encoding a $V_H$ that hybridizes under stringent conditions to a nucleic acid molecule comprising a nucleic acid sequence of one of SEQ ID NO: 4 or 8.

The nucleic acid molecule encoding either or both of the entire heavy and light chains of an anti-CLL-1 antibody or the variable regions thereof may be obtained from any source that produces an anti-CLL-1 antibody. Methods of isolating mRNA encoding an antibody are well-known in the art. See e.g., Sambrook et al., supra. The mRNA may be used to produce cDNA for use in the polymerase chain reaction (PCR) or cDNA cloning of antibody genes. In one embodiment of the invention, the nucleic acid molecules may be obtained from a hybridoma that expresses an anti-CLL-1 antibody as described above, preferably a hybridoma that has as one of its fusion partners a transgenic animal cell that expresses human immunoglobulin genes, such as a XENOMOUSE® (Amgen, Fremont, Calif., USA), non-human mouse transgenic animal, or a non-human, non-mouse transgenic animal. In another embodiment, the hybridoma is derived from a non-human, non-transgenic animal, which may be used, e.g., for humanized antibodies.

A nucleic acid molecule encoding the entire heavy chain of an anti-CLL-1 antibody may be constructed by fusing a nucleic acid molecule encoding the variable domain of a heavy chain or an antigen-binding domain thereof with a constant domain of a heavy chain. Similarly, a nucleic acid molecule encoding the light chain of an anti-CLL-1 antibody may be constructed by fusing a nucleic acid molecule encoding the variable domain of a light chain or an antigen-binding fragment thereof with a constant domain of a light chain. The nucleic acid molecules encoding the $V_H$ and $V_L$ chain may be converted to full-length antibody genes by inserting them into expression vectors already encoding heavy chain constant and light chain constant regions, respectively, such that the $V_H$ segment is operatively linked to the heavy chain constant region ($C_H$) segment(s) within the vector and the $V_L$ segment is operatively linked to the light chain constant region ($C_L$) segment within the vector. Alternatively, the nucleic acid molecules encoding the $V_H$ or $V_L$ chains are converted into full-length antibody genes by linking, e.g., ligating, the nucleic acid molecule encoding a $V_H$ chain to a nucleic acid molecule encoding a $C_H$ chain using standard molecule biological techniques. The same may be achieved using nucleic acid molecules encoding $V_L$ and $C_L$ chains. The sequences of human heavy and light chain constant region genes are known in the art. See, e.g., Kabat et al., 1991, supra. Nucleic acid molecules encoding the full-length heavy and/or light chains may then be expressed from a cell into which they have been introduced and the anti-CLL-1 antibody isolated.

In another embodiment, a nucleic acid molecule encoding either the heavy chain of an anti-CLL-1 antibody or an antigen-binding fragment thereof or the light chain of an anti-CLL-1 antibody or an antigen-binding fragment thereof may be isolated from a non-human, non-mouse animal that expresses human immunoglobulin genes and has been immunized with an CLL-1 antigen. In another embodiment, the nucleic acid molecule may be isolated from an anti-CLL-1 antibody producing cell derived from a non-transgenic animal or from a human patient who produces anti-CLL-1 antibodies. Methods of isolating mRNA from the anti-CLL-1 antibody-producing cells may be isolated by standard techniques, cloned and/or amplified using PCR and library construction techniques, and screened using standard protocols to obtain nucleic acid molecules encoding anti-CLL-1 heavy and light chains.

The nucleic acid molecules may be used to recombinantly express large quantities of anti-CLL-1 antibodies, as described below. The nucleic acid molecules may also be used to produce chimeric antibodies, single chain antibodies, immunoadhesins, diabodies, mutated antibodies and antibody derivatives. If the nucleic acid molecules are derived from a non-human, non-transgenic animal, the nucleic acid molecules may be used for antibody humanization.

The invention further provides nucleic acids that hybridize to other nucleic acids (e.g., nucleic acids comprising a nucleotide sequence listed in Tables 1-2) under particular hybridization conditions. Methods for hybridizing nucleic acids are well-known in the art. See, e.g., Current Protocols in Molecular Biology, John Wiley and Sons, N.Y. (1989), 6.3.1-6.3.6. As defined herein, a moderately stringent hybridization condition uses a prewashing solution containing 5x sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C. in 0.5×SSC, 0.1% SDS. A stringent hybridization condition hybridizes in 6×SSC at 45° C., followed by one or more washes in 0.1 ×SSC, 0.2% SDS at 68° C. Furthermore, one of skill in the art can manipulate the hybridization and/or washing conditions to increase or decrease the stringency of hybridization such that nucleic acids comprising nucleotide sequence that are at least 65%, at least 70%, at least 75%, at least 80%, at least 85%, at least 90%, at least 95%, at least 96%, at least 97%, at least 98% or at least 99% identical to each other typically remain hybridized to each other.

The basic parameters affecting the choice of hybridization conditions and guidance for devising suitable conditions are set forth by, for example, Sambrook, Fritsch, and Maniatis (*Molecular Cloning: A Laboratory Manual*, Cold Spring Harbor Laboratory Press, Cold Spring Harbor, N.Y., chapters 9 and 11 (1989); *Current Protocols in Molecular Biology*, Ausubel et al., eds., John Wiley and Sons, Inc., sections 2.10 and 6.3-6.4 (1995), both of which are herein incorporated by reference in their entirety for all purposes) and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antibody or antibody derivative of the invention) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively change the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences encoding anti-CLL-1 antibodies or antigen-binding fragments thereof. Such nucleic acid molecules may comprise only a portion of a nucleic acid sequence encoding a full-length polypeptide, for example, a fragment that can be used as a probe or primer or a fragment encoding an active portion (e.g., an CLL-1 binding portion) of a polypeptide an anti-CLL-1 antibody or antigen-binding fragment thereof.

In another embodiment, the nucleic acid molecules may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable domains of anti-CLL-1 antibodies. In a preferred embodiment, the nucleic acid molecules are oligonucleotides. In a more preferred embodiment, the oligonucleotides are from highly variable regions of the heavy and light chains of the antibody of interest. In an even more preferred embodiment, the oligonucleotides encode all or part of one or more of the CDRs.

Probes based on the sequence of a nucleic acid encoding all or a portion thereof of an anti-CLL-1 antibody or antigen-binding fragment thereof can be used to detect the nucleic acid or similar nucleic acids, for example, transcripts encoding a polypeptide of an anti-CLL-1 antibody or antigen-binding fragment thereof. The probe may comprise a label group, e.g., a radioisotope, a fluorescent compound, an enzyme, or an enzyme co-factor. Such probes can be used to identify a cell that expresses the polypeptide.

B. Vectors

The invention provides vectors comprising the nucleic acid molecules that encode the heavy chain or the antigen-binding portion thereof of an anti-CLL-1 antibody. Also provided are vectors comprising the nucleic acid molecules that encode the light chain or antigen-binding portion thereof of an anti-CLL-1 antibody. Additionally, vectors comprising nucleic acid molecules encoding fusion proteins, modified antibodies, antibody fragments, and probes thereof are provided herein.

In another aspect, the present invention provides vectors comprising a nucleic acid encoding a polypeptide of an anti-CLL-1 antibody or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors may comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., Simian Virus 40 (SV40) early gene enhancer, Rous sarcoma virus (RSV) promoter and cytomegalovirus (CMV) promoter), those that direct expression of the nucleotide sequence only in certain host cells (e.g., tissue-specific regulatory sequences, see Voss et al., *Trends Biochem. Sci.* 11:287 (1986); Maniatis et al., *Science* 236:1237 (1986), incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems. It will be appreciated by those skilled in the art that the design of the expression vector can depend on such factors as the choice of the host cell to be transformed, the level of expression of protein desired, etc. The expression vectors provided herein may be introduced into host cells to thereby produce proteins or peptides, including fusion protein or peptides, encoded by nucleic acids as described herein.

To express the antibodies, or antigen-binding fragments thereof, DNAs encoding partial or full-length light and heavy chains, obtained as described above, are inserted into expression vectors such that the genes area operatively linked to transcriptional and translational control sequences. Expression vectors include plasmids, retroviruses, cosmids, YACs, EBV-derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can be easily inserted and expressed, as described above. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector may also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (e.g., a signal peptide from a non-immunoglobulin protein).

In addition to the antibody chain genes, the recombinant expression vectors disclosed herein carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, CMV (such as the CMV promoter/enhancer), SV40 (such as the SV40 promoter/enhancer), adenovirus (e.g., the adenovirus major late promoter (Ad-MLP)), polyoma and strong mammalian promoters such as native immunoglobulin and actin promoters. For further description of viral regulatory elements, and sequences thereof, see e.g., U.S. Pat. Nos. 5,168,062 4,510,245, and 4,968,615.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665, and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neomycin gene (for G418 selection).

C. Host Cells

In another aspect, host cells are provided into which a recombinant expression vector encoding an anti-CLL-1 antibody or antigen-binding fragment thereof has been introduced. A host cell can be any prokaryotic cell (for example, *E. coli*) or eukaryotic cell (for example, yeast (for example, *Pichia pastoris*), insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

V. Preparation of Antibodies

As explained above, the CLL-1 antigen is used to produce antibodies for therapeutic, diagnostic and purification purposes. These antibodies may be polyclonal or monoclonal antibody preparations, monospecific antisera, human antibodies, or may be hybrid or chimeric antibodies, such as humanized antibodies, altered antibodies, F(ab')₂ fragments, Fab fragments, Fv fragments, single-domain antibodies, dimeric or trimeric antibody fragment constructs, minibodies, or functional fragments thereof which bind to the antigen in question. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, the CLL-1 antigens can be used to produce CLL-1-specific polyclonal and monoclonal antibodies for use in diagnostic and detection assays, for purification and for use as therapeutics. CLL-1-specific polyclonal and monoclonal antibodies bind with high affinity to CLL-1 antigens.

The non-human antibodies that are provided can be, for example, derived from any antibody-producing animal, such as mouse, rat, rabbit, goat, donkey, or non-human primate (such as monkey (e.g., cynomologous or rhesus monkey) or ape (e.g., chimpanzee)). Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Non-human antibodies can be used, for instance, in in vitro cell culture and cell-culture based applications, or any other application where an immune response to the antibody does not occur or is insignificant, can be prevented, is not a concern, or is desired. In certain embodiments of the invention, the antibodies may be produced by immunizing with full-length CLL-1 (i.e., SEQ ID NO: 2) or with the extracellular domain (i.e., SEQ ID NO: 3). The antibodies may be polyclonal, monoclonal, or may be synthesized in host cells by expressing recombinant DNA.

Fully human antibodies may be prepared as described above by immunizing transgenic animals containing human immunoglobulin loci or by selecting a phage display library that is expressing a repertoire of human antibodies.

Mouse and/or rabbit monoclonal antibodies directed against epitopes present in the CLL-1 antigen can also be readily produced. In order to produce such monoclonal antibodies, the mammal of interest, such as a rabbit or mouse, is immunized, such as by mixing or emulsifying the antigen in saline, preferably in an adjuvant such as Freund's complete adjuvant (FCA), and injecting the mixture or emulsion parenterally (generally subcutaneously or intramuscularly). The animal is generally boosted 2-6 weeks later with one or more injections of the antigen in saline, preferably using Freund's incomplete adjuvant (FIA).

The anti-CLL-1 monoclonal antibodies (mAbs) can be produced by a variety of techniques, including conventional monoclonal antibody methodology, e.g., the standard somatic cell hybridization technique of Kohler and Milstein, *Nature* 256:495 (1975), herein incorporated by reference in its entirety for all purposes. Alternatively, other techniques for producing monoclonal antibodies can be employed, for example, the viral or oncogenic transformation of B-lymphocytes. One suitable animal system for preparing hybridomas is the murine system, which is a very well-established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas are also well-known.

Antibodies may also be generated by in vitro immunization, using methods known in the art. See, e.g., James et al., *J. Immunol. Meth.* 100:5-40 (1987). Polyclonal antisera are then obtained from the immunized animal. However, rather than bleeding the animal to extract serum, the spleen (and optionally several large lymph nodes) is removed and dissociated into single cells. If desired, the spleen cells (splenocytes) may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated splenocytes, are then induced to fuse with cells from an immortalized cell line (also termed a "fusion partner"), to form hybridomas. Typically, the fusion partner includes a property that allows selection of the resulting hybridomas using specific media. For example, fusion partners can be hypoxanthine/aminopterin/thymidine (HAT)-sensitive.

If rabbit-rabbit hybridomas are desired, the immortalized cell line will be from a rabbit. Such rabbit-derived fusion partners are known in the art and include, for example, cells of lymphoid origin, such as cells from a rabbit plasmacytoma as described in Spieker-Polet et al., *Proc. Natl. Acad. Sci. USA* 92:9348-9352 (1995) and U.S. Pat. No. 5,675,063, or the TP-3 fusion partner described in U.S. Pat. No. 4,859,595, incorporated herein by reference in their entireties. If a rabbit-mouse hybridoma or a rat-mouse or mouse-mouse hybridoma, or the like, is desired, the mouse fusion partner will be derived from an immortalized cell line from a mouse, such as a cell of lymphoid origin, typically from a mouse myeloma cell line. A number of such cell lines are known in the art and are available from ATCC (American Type Culture Collection, Manassas, Va., USA).

Fusion is accomplished using techniques well known in the art. Chemicals that promote fusion are commonly referred to as fusogens. These agents are extremely hydrophilic and facilitate membrane contact. One particularly preferred method of cell fusion uses polyethylene glycol (PEG). Another method of cell fusion is electrofusion. In this method, cells are exposed to a predetermined electrical discharge that alters the cell membrane potential. Additional methods for cell fusion include bridged-fusion methods. In this method, the antigen is biotinylated and the fusion partner is avidinylated. When the cells are added together, an antigen-reactive B cell-antigen-biotin-avidin-fusion partner bridge is formed. This permits the specific fusion of an antigen-reactive cell with an immortalizing cell. The method may additionally employ chemical or electrical means to facilitate cell fusion.

Following fusion, the cells are cultured in a selective medium (e.g., HAT medium). In order to enhance antibody secretion, an agent that has secretory stimulating effects can optionally be used, such as IL-6. See, e.g., Liguori et al., *Hybridoma* 20:189-198 (2001). The resulting hybridomas can be plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice). For example, hybridomas producing CLL-1-specific antibodies can be identified using RIA or ELISA and isolated by cloning in semi-solid agar or by limiting dilution. Clones producing the desired antibodies can be isolated by another round of screening.

An alternative technique for generating the anti-CLL-1 monoclonal antibodies is the selected lymphocyte antibody method (SLAM). This method involves identifying a single lymphocyte that is producing an antibody with the desired specificity or function within a large population of lymphoid cells. The genetic information that encodes the specificity of the antibody (i.e., the immunoglobulin $V_H$ and $V_L$ DNA) is then rescued and cloned. See, e.g., Babcook et al., *Proc. Natl. Acad. Sci. USA* 93:7843-7848 (1996), for a description of this method.

For further descriptions of rabbit monoclonal antibodies and methods of making the same from rabbit-rabbit and rabbit-mouse fusions, see, e.g., U.S. Pat. No. 5,675,063 (rabbit-rabbit); U.S. Pat. No. 4,859,595 (rabbit-rabbit); U.S. Pat. No. 5,472,868 (rabbit-mouse); and U.S. Pat. No. 4,977,081 (rabbit-mouse).

The single-chain antibodies that are provided may be formed by linking heavy and light chain variable domain (Fv region) fragments (see, e.g., Table 1) via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., *Prot. Eng.* 10:423 (1997); Kort et al., *Biomol. Eng.* 18:95-108 (2001)). By combining different $V_L$ and $V_H$-comprising polypeptides, one can form multimeric scFvs that bind to different epitopes (Kriangkum et al., *Biomol. Eng.* 18:31-40 (2001)). Techniques developed for the production of single-chain antibodies include those described in U.S. Pat. No. 4,946,778; Bird, *Science* 242:423 (1988); Huston et al., *Proc. Natl. Acad. Sci. USA* 85:5879 (1988); Ward et al., *Nature* 334:544 (1989); de Graff et al., *Methods Mol. Biol.* 178:379-87 (2002)). Single-chain antibodies derived from antibodies provided herein include, but are not limited to scFvs comprising the variable domain combinations: $V_L 1 V_H 1$, $V_L 1 V_H 2$, $V_L 2 V_H 1$ or $V_L 2 V_H 2$.

Antibodies provided herein that are of one subclass can be changed to antibodies of a different subclass using subclass switching methods. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., *Methods Mol. Biol.* 178:303-16 (2002).

Accordingly, the antibodies that are provided include those comprising, for example, the following variable domain combinations: $V_L 1 V_H 1$, $V_L 1 V_H 2$, $V_L 2 V_H 1$ or $V_L 2 V_H 2$ having a desired isotype (for example, IgA, $IgG_1$, $IgG_2$, $IgG_3$, $IgG_4$, IgE, and IgD) as well as Fab or $F(ab')_2$ fragments thereof. Moreover, if an $IgG_4$ is desired, it may also be desired to introduce a point mutation (eg. CPSCP →CPPCP) in the hinge region as described in Bloom et al., *Protein Sci.* 6:407 (1997), incorporated by reference herein) to alleviate a tendency to form intra-H chain disulfide bonds that can lead to heterogeneity in the $IgG_4$ antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., *BioTechnology* 10:770 (1992).

Conservative modifications may be made to the heavy and light chains (and corresponding modifications to the encoding nucleic acids) to produce an anti-CLL-1 antibody having functional and biochemical characteristics. Methods for achieving such modifications are described above.

The anti-CLL-1 antibodies and functional fragments thereof may be further modified in various ways. For example, if they are to be used for therapeutic purposes, they may be conjugated with polyethylene glycol (PEGylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody of fragment thereof. Another useful fusion is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a nonnative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human CLL-1 or for modifying the binding affinity of other anti-CLL-1 antibodies described herein.

VI. Expression of Anti-CLL-1 Antibodies

The anti-CLL-1 antibodies and antigen-binding fragments can be prepared by any of a number of conventional techniques. For example, anti-CLL-1 antibodies may be produced by recombinant expression systems, using any technique known in the art. See, for example, *Monoclonal Antibodies, Hybridomas: A New Dimension in Biological Analyses*, Kennet et al. (eds.) Plenum Press, N.Y. (1980); *Antibodies: A Laboratory Manual*, Harlow and Lane (eds.), Cold Spring Harbor Laboratory Press, Cold Spring Harbor, N.Y. (1988).

The antibodies described herein can be expressed in hybridoma cell lines or in cell lines other than hybridomas. Expression constructs encoding the antibodies can be used to transform a mammalian, insect, or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455 (which patents are hereby incorporated herein by reference for any purpose). The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: a heavy chain constant region (e.g., $C_H1$, $C_H2$ and/or $C_H3$); a heavy chain variable region; a light chain constant region; a light chain variable region; one or more CDRs of the light or heavy chain of the anti-CLL-1 antibody. These nucleic acid sequences are inserted into an appropriate expression vector using standard ligation techniques. In one embodiment, the 21.16 or 1075.7 heavy or light chain constant region is appended to the C-terminus of the CLL-1-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences. Other useful vectors for cloning and expressing the anti-CLL-1 antibodies and fragments thereof include those described in Bianchi and McGrew, *Biotech. Biotechnol. Bioeng.* 84:439-44 (2003), herein incorporated by reference. Additional suitable expression vectors are discussed, for example, in *Methods Enzymol*, vol. 185 (D. V. Goeddel, ed.), 1990, New York: Academic Press, herein incorporated by reference.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis (such as hexaHis), or another "tag" for which commercially available antibodies exist, such as V5-His, FLAG®, HA (hemaglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, QIAGEN® column chromatography (Qiagen, Chatsworth, Calif., USA), or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass., USA.) is suitable for most gram-negative bacteria and various origins of replication (e.g., SV40, polyoma, adenovirus, vesicular stomatitis virus (VSV), or papilloma viruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors provided herein will typically contain a promoter that is recognized by the host organism and operably linked to nucleic acid encoding an anti-CLL-1 antibody or antigen-binding fragment thereof. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding an anti-CLL-1 antibody by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably SV40. Other suitable mammalian promoters include heterologous mammalian promoters, for example, heat-shock promoters and the actin promoter.

Particular promoters useful in the practice of the recombinant expression vectors disclosed herein include, but are not limited to: the SV40 early promoter region (Bemoist and Chambon, *Nature* 290:304-10 (1981)); the CMV promoter; the promoter contained in the 3' long terminal repeat of Rous sarcoma virus (Yamamoto, et al., *Cell* 22:787-97 (1980)); the herpes thymidine kinase promoter (Wagner et al., *Proc. Natl. Acad. Sci. U.S.A.* 78:1444-45 (1981)); the regulatory sequences of the metallothionine gene (Brinster et al., *Nature* 296:39-42 (1982)); prokaryotic expression vectors such as the beta-lactamase promoter (Villa-Kamaroff et al., *Proc. Natl. Acad. ScL U.S.A.,* 75:3727-31 (1978)); or the tac promoter (DeBoer et al., *Proc. Natl. Acad. ScL U.S.A.* 80:21-25 (1983)). Also available for use are the following animal transcriptional control regions, which exhibit tissue specificity and have been utilized in transgenic animals: the elastase I gene control region that is active in pancreatic acinar cells (Swift et al., *Cell* 38:63946 (1984); Ornitz et al., *Cold Spring Harbor Symp. Quant. Biol.* 50:399409 (1986); MacDonald, *Hepatology* 7:425-515 (1987)); the insulin gene control region that is active in pancreatic beta cells (Hanahan, *Nature* 315:115-22 (1985)); the mouse mammary tumor virus control region that is active in testicular, breast, lymphoid and mast cells (Leder et al., *Cell* 45:485-95 (1986)); the albumin gene control region that is active in liver (Pinkert et al., *Genes Devel.* 1:268-76 (1987)); the alpha-feto-protein gene control region that is active in liver (Krumlauf et al., *Mol. Cell. Biol.* 5:1639-48 (1985); Hammer et al., *Science* 235:53-58 (1987)); the alpha 1-antitrypsin gene control region that is active in the liver (Kelsey et al., *Genes Devel.* 1:161-71 (1987)); the beta-globin gene control region that is active in myeloid cells (Mogram et al., *Nature* 315:338-40 (1985); Kollias et al., *Cell* 46:89-94 (1986)); the myelin basic protein gene control region that is active in oligodendrocyte cells in the brain (Readhead et al., *Cell* 48:703-12 (1987)); the myosin light chain-2 gene control region that is active in skeletal muscle (Sani, *Nature* 314:283-86 (1985)); the gonadotropic releasing hormone gene control region that is active in the hypothalamus (Mason et al., *Science* 234:1372-78 (1986)); and most particularly the immunoglobulin gene control region that is active in lymphoid cells (Grosschedl et al., *Cell* 38:647-58 (1984); Adames et al., *Nature* 318 533-38 (1985); Alexander et al., *Mol. Cell Biol.* 7:1436-44 (1987)).

An enhancer sequence may be inserted into the vector to increase the transcription in higher eukaryotes of a nucleic acid encoding an anti-CLL-1 antibody or antigen-binding fragment thereof. Enhancers are cis-acting elements of DNA, usually about 10-300 by in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an anti-CLL-1 antibody, is co-amplified with the selection gene. As a result, increased quantities of anti-CLL-1 antibody polypeptides are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have in the −1 position (relative to the first amino acid of the mature protein) one or more additional amino acids incident to expression which may not have been totally removed. For example, the final protein product may have one or two amino acid residues found in the peptidase cleavage site attached to the amino-terminus. Alternatively, use of some enzyme cleavage sites may result in a slightly truncated yet active form of the desired polypeptide if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding an anti-CLL-1 antibody or antigen-binding fragment thereof is inserted into the proper site of the vector.

The completed vector containing sequences encoding the anti-CLL-1 antibody or antigen-binding region thereof is inserted into a suitable host cell for amplification and/or polypeptide expression. The transformation of an expression vector for an anti-CLL-1 antibody or antigen-binding fragment thereof into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes an anti-CLL-1 antibody or antigen-binding fragment thereof that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, human embryonic kidney (HEK) cells, HEK293 cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies with constitutive CLL-1 binding properties.

VII. Pharmaceutical Compositions

A. Exemplary Formulations

In certain embodiments, the invention also provides compositions comprising the subject anti-CLL-1 antibodies or antigen-binding fragments thereof together with one or more of the following: a pharmaceutically acceptable diluent; a carrier; a solubilizer; and emulsifier; a preservative; and/or an adjuvant. Such compositions may contain an effective amount of the anti-CLL-1 antibody or antigen-binding fragment thereof in the preparation of a pharmaceutical composition or medicament. Such compositions can be used in the treatment of a variety of diseases such as those listed below.

The anti-CLL-1 antibodies may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease or disorder targeted. The compositions also preferably include pharmaceutically acceptable vehicles, carriers or adjuvants, well known in the art.

A "pharmaceutically acceptable" vehicle, carrier or adjuvant is a non-toxic agent that can be tolerated by a recipient patient. Representative non-limiting examples of such agents include human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, phosphate-buffered saline, dextrose, glycerol, ethanol, or the like, and combinations thereof. Other suitable agents are well-known to those in the art. See, for example, *Remington's Pharmaceutical Sciences*, Mack Publishing Company, Easton, Pa., 19th edition, 1995. Actual methods of preparing such compositions are also known, or will be apparent, to those skilled in the art. See, e.g., *Remington's Pharmaceutical Sciences*, 1995, supra.

Acceptable formulation components for pharmaceutical preparations are nontoxic to recipients at the dosages and concentrations employed. In addition to the antibodies and antigen-binding fragments that are provided, the compositions may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences*, 1995, supra), hereby incorporated by reference in its entirety for all purposes.

The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles. Compositions comprising anti-CLL-1 antibodies or antigen-binding fragments thereof may be prepared for storage by mixing the selected composition having the desired degree of purity with optional formulation agents in the form of a lyophilized cake or an aqueous solution. Further, the anti-CLL-1 antibodies or antigen-binding fragments thereof may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions may comprise TRIS buffer of about pH 6.5-8.5, or acetate buffer of about pH 4.0-5.5, which may further include sorbitol or a suitable substitute therefore.

Typically, the pharmaceutical composition to be used for in vivo administration is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

Additional pharmaceutical methods may be employed to control the duration of action of an antibody in a therapeutic application. Control release preparations can be prepared through the use of polymers to complex or adsorb the antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446 (1992). The rate of release of an antibody from such a matrix depends upon the molecular weight of the protein, the amount of antibody within the matrix, and the size of dispersed particles. Saltzman et al., *Biophys. J.* 55:163 (1989); Sherwood et al., supra. Other solid dosage forms are described in *Remington's Pharmaceutical Sciences*, 1995, supra.

The above compositions may be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to a tumor in question, will also find use with the present invention. Eye drops may be used for intraocular administration. When administering the compositions by injection, the administration may be by continuous infusion or by single or multiple boluses. Intravenous injection provides a useful mode of administration due to the thoroughness of the circulation in rapidly distributing antibodies. For parenteral administration, the antibodies may be administered in a pyrogen-free, parenterally acceptable aqueous solution comprising the desired anti-CLL-1 antibodies or antigen-binding fragments thereof in a pharmaceutically acceptable vehicle. A particularly suitable vehicle for parenteral injection is sterile distilled water in which the anti-CLL-1 antibodies or antigen-binding fragments thereof are formulated as a sterile, isotonic solution, properly preserved.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The subject compositions comprising anti-CLL-1 antibodies or antigen-binding fragments thereof also may be used ex vivo. In such instances, cells, tissues or organs that have been removed from the patient are exposed to or cultured with the anti-CLL-1 antibody or antigen-binding fragment thereof. The cultured cells may then be implanted back into the patient or a different patient or used for other purposes.

In certain embodiments, anti-CLL-1 antibodies or antigen-binding fragments thereof may be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

B. Dosage

For purposes of therapy, antibodies are administered to a patient in a therapeutically effective amount. A "therapeutically effective amount" is one that is physiologically significant. An agent is physiologically significant if its presence results in a detectable change in the physiology or disease or disorder state of a recipient. A "prophylactically effective amount" refers to an amount that is effective to prevent, hinder or retard the onset of a disease state or symptom.

Therapeutically effective doses will be easily determined by one of skill in the art and will depend on the severity and course of the disease, the patient's health and response to treatment, the patient's age, weight, height, sex, previous medical history and the judgment of the treating physician. Typically, it is desirable to provide the recipient with a dosage of antibody component or immunoconjugate which is in the range of from about 1 pg/kg to 10 mg/kg (amount of agent/body weight of patient), although a lower or higher dosage also may be administered as circumstances dictate. In preferred embodiments, anti-CLL-1 antibodies are administered at low protein doses, such as 20 mg to 2 g protein per dose, given once, or repeatedly, parenterally. Alternatively, antibodies are administered in doses of 20 to 1000 mg protein per dose, or 20 to 500 mg protein per dose, or 20 to 100 mg protein per dose.

VIII. Diagnostic Assays

The anti-CLL-1 antibodies provided herein may be used in vivo, i.e., injected into subjects, for diagnostic or therapeutic uses. The use of antibodies for in vivo diagnosis is well known in the art. Sumerdon et al., *Nucl. Med. Biol* 17:247-254 (1990) have described an optimized antibody-chelator for the radio-immunoscintigraphic imaging of carcinoembryonic antigen (CEA)-expressing tumors using Indium-111 as the label. Griffin et al., *J Clin Onc* 9:631-640 (1991) have described the use of this agent in detecting tumors in patients suspected of having recurrent colorectal cancer. The use of similar agents with paramagnetic ions as labels for magnetic resonance imaging is known in the art (R. B. Lauffer, *Magnetic Resonance in Medicine* 22:339-342 (1991). Thus, antibodies directed against the CLL-1 antigen may be injected into subjects suspected of having a disease or disorder in which CLL-1 is implicated for the purpose of diagnosing or staging the disease status of the patient. The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used. Localization of the label within the patient allows determination of the presence and/or spread of the disease.

The antibodies generated against the CLL-1 antigen may also be used in standard in vitro immunoassays, to screen biological samples such as blood, tissues and/or tumors for the presence or absence of the CLL-1 antigen. Thus, the anti-CLL-1 antibodies produced as described above, can be used in diagnostic assays. The anti-CLL-1 antibodies can be used as either the capture component and/or the detection component in the assays, as described further below. Thus, the presence of the CLL-1 antigen can be determined by the presence of CLL-1 antigens and/or anti-CLL-1 antibodies.

For example, the presence of CLL-1 antigens can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as enzyme-linked immunosorbent assays ("ELISAs"); biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigens and the antibodies described above.

Assays can also be conducted in solution, such that the antigens and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The antigens and antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

IX. Therapeutic Uses

The present invention provides antibodies or antigen-binding fragments thereof that bind to CLL-1 epitopes that are useful for the treatment of human diseases and pathological conditions. Agents that modulate CLL-1 activity, or other cellular activity, may be used in combination with other therapeutic agents to enhance their therapeutic effects or decrease potential side effects.

Supplemental active compounds can also be incorporated into the compositions. In certain embodiments, an anti-CLL-1 antibody or antigen-binding fragment may be co-formulated with one or more additional therapeutic agents, such as a chemotherapeutic agent, an antineoplastic agent, or an anti-tumor agent. These agents include without limitation, antibodies that bind other targets (e.g., antibodies that bind one ore more growth factors, cytokines, or cell surface receptors), CLL-1 binding proteins, antineoplastic agents, chemotherapeutic agents, anti-tumor agents, antisense oligonucleotides against CLL-1, CLL-1 peptide analogs, and/or one or more chemical agents that inhibit CLL-1 production or activity, which are known in the art.

In another aspect, the anti-CLL-1 antibody may be co-administered with other therapeutic agents, such as antineoplastic drugs or molecules, to a patient who has a hyperproliferative disorder, such as cancer or a tumor. One aspect of the invention relates to a method for the treatment of the hyperproliferative disorder in a mammal comprising administering to said mammal a therapeutically effective amount of a compound comprising an anti-CLL-1 antibody or antigen-binding fragment thereof in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens. In a more preferred embodiment, the antibody may be administered with an antineoplastic agent, such as adriamycin or taxol. In another preferred embodiment, the antibody or combination therapy is administered along with radiotherapy, chemotherapy, photodynamic therapy, surgery or other immunotherapy. In yet another preferred embodiment, the antibody will be administered with another antibody. For example, an anti-CLL-1 antibody may be administered with an antibody or other agent that is known to inhibit tumor or cancer cell proliferation, e.g., an antibody or agent that inhibits erbB2 receptor, EGF-R, CD20 or VEGF.

Co-administration of the anti-CLL-1 antibody or antigen-binding fragment thereof with an additional therapeutic agent (combination therapy) encompasses administering a pharmaceutical composition comprising an anti-CLL-1 antibody and the additional therapeutic agent and administering two or more separate pharmaceutical compositions, one comprising an anti-CLL-1 antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent. Similarly, administration of the anti-CLL-1 antibody may be administered prior to or subsequent to other therapy, such as radiotherapy, chemotherapy, photodynamic therapy, surgery or other immunotherapy The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months, once every six months, or may be administered continuously via a minipump. The combination therapy may be administered via an oral, mucosal, buccal, intranasal, inhalable, intravenous, subcutaneous, intramuscular, parenteral, intratumor or topical route. The combination therapy may be administered at a site distant from the site of the tumor or at a site proximal to the tumor. The combination therapy generally will be administered for as long as the tumor is present provided that the antibody causes the tumor or cancer to stop growing or to decrease in weight or volume.

In a still further embodiment, the anti-CLL-1 antibody can be labeled with a radiolabel, an immunotoxin or a toxin, or is a fusion protein comprising a toxic peptide. The anti-CLL-1 antibody or anti-CLL-1 antibody fusion protein directs the radiolabel, immunotoxin, toxin or toxic peptide to the CLL-1-expressing cell. In a preferred embodiment, the radiolabel, immunotoxin, toxin or toxic peptide is internalized after the anti-CLL-1 antibody binds to the CLL-1 antigen on the surface of the cell.

In one aspect, the present invention provides reagents and methods useful for treating diseases and conditions characterized by undesirable or aberrant levels of CLL-1 in a cell. In a particular embodiment, the antibodies and derivatives thereof are used in vivo to treat, prevent or diagnose a variety of CLL-1-related neoplastic diseases. These diseases include hematologic malignancies including, but not limited to myeloproliferative diseases including acute myelogenous leukemia, chronic myelogenous leukemia, chronic neutrophilic leukemia, chronic eosinophilic leukemia/hypereosinophilic syndrome, chronic idiopathic myelofibrosis, polycythemia vera, essential (or primary) thrombocythemia, unclassifiable myeloproliferative disease; myelodysplastic/myeloproliferative diseases including chronic myelomonocytic leukemia, atypical chronic myelogenous leukemia, juvenile myelomonocytic leukemia; myelodysplastic syndromes including chronic anemia, nonprogressive anemia, refractory anemia, refractory cytopenia, 5q¯ (5q deletion) syndrome, unclassifiable myelodysplastic syndrome; acute myeloid leukemias, acute myelomonocytic leukemia, acute monocytic leukemia, acute erythoid leukemia, acute megakaryocytic leukemia, acute basophilic leukemia, acute panmyelosis with myelofibrosis; acute biphenotypic leukemias; precursor B-cell neoplasms including precursor B-lymphoblastic leukemia/lymphoma, precursor B-cell acute lymphoblastic leukemia; mature (peripheral) B-cell neoplasms including B-cell acute lymphocytic leukemia, B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma, nodal marginal zone B-cell lymphoma, follicular lymphoma, mantle cell lymphoma, diffuse large B-cell lymphoma, mediastinal large B-cell lymphoma, primary effusion lymphoma, Burkitt lymphoma/Burkitt cell leukemia; precursor T-cell neoplasms including precursor T-lymphoblastic lymphoma/leukemia, precursor T-cell acute lymphoblastic leukemia; mature (peripheral) T-cell neoplasms including T-cell prolymphocytic leukemia, T-cell granular lymphocytic leukemia, aggressive NK-cell leukemia, adult T-cell lymphoma/leukemia, extranodal NK/T-cell lymphoma, enteropathy-type T-cell lymphoma, hepatosplenic gamma-delta T-cell lymphoma, cutaneous T-cell lymphoma, subcutaneous panniculities-like T-cell lymphoma, mycosis fungiodes/Sezary syndrome, anaplastic large-cell lymphoma, peripheral T-cell lymphoma, angioimmunoblastic T-cell lymphoma, anaplastic large-cell lymphoma; Hodgkin lymphomas; mast cell diseases including cutaneous mastocytosis, systemic mast cell disease, mast cell leukemia/sarcoma; macrophage/histiocytic sarcomas; and dendritic cell neoplasms including Langerhans cell histiocytosis, Langerhans cell sarcoma; follicular dendritic cell sarcoma/tumor, dendritic cell sarcoma; myelomas including multiple myeloma, extramedullary plasmacytoma, solitary myeloma; and Waldenstrom macroglobulinemia; X-linked lymphoproliferative disorders; and Epstein Barr Virus (EBV)-related conditions such as mononucleosis.

The present invention also provides methods of treating cancer in an animal, including humans, comprising administering to the animal an effective amount of an antibody or antigen-binding fragment thereof that induces ADCC or CDC of CLL-1-expressing cells. The invention is further directed to methods of inhibiting cancer cell growth, including processes of cellular proliferation, invasiveness, and metastasis in biological systems. The methods disclosed herein include use of a compound comprising anti-CLL-1 antibodies or antigen-binding fragments thereof as an inhibitor of cancer cell growth. Preferably, the methods are employed to inhibit or reduce cancer cell growth, invasiveness, metastasis or tumor incidence in living animals, such as mammals. The methods provided herein are also readily adaptable for use in assay systems, e.g., assaying cancer cell growth and properties thereof, as well as identifying compounds that affect cancer cell growth.

The cancers treatable by the methods provided herein preferably occur in mammals. Mammals include, for example, humans and other primates, as well as pet or companion animals such as dogs and cats, laboratory animals such as rats, mice and rabbits, and farm animals such as horses, pigs, sheep and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Treatable neoplasms also include solid phase tumors/malignancies, i.e., carcinomas, locally advanced tumors and human soft tissue sarcomas. Carcinomas include those malignant neoplasms derived from epithelial cells that infiltrate (invade) the surrounding tissues and give rise to metastastic cancers, including lymphatic metastases. Adenocarcinomas are carcinomas derived from glandular tissue, or which form recognizable glandular structures. Another broad category of cancers includes sarcomas, which are tumors whose cells are embedded in a fibrillar or homogeneous substance like embryonic connective tissue. The invention also enables treatment of cancers of the myeloid systems, including leukemias and other cancers that typically do not present as a tumor mass, but are distributed in the vascular or lymphoreticular systems.

The type of cancer or tumor cells that may be amenable to treatment according to the invention include, for example, acute lymphocytic leukemia, acute nonlymphocytic leukemia, chronic lymphocytic leukemia, chronic myelocytic leukemia, cutaneous T-cell lymphoma, hairy cell leukemia, acute myeloid leukemia, erythroleukemia, chronic myeloid (granulocytic) leukemia, Hodgkin's disease, and non-Hodgkin's lymphoma, gastrointestinal cancers including esophageal cancer, stomach cancer, colon cancer, colorectal cancer, polyps associated with colorectal neoplasms, pancreatic cancer and gallbladder cancer, cancer of the adrenal cortex, ACTH-producing tumor, bladder cancer, brain cancer including intrinsic brain tumors, neuroblastomas, astrocytic brain tumors, gliomas, and metastatic tumor cell invasion of the central nervous system, Ewing's sarcoma, head and neck cancer including mouth cancer and larynx cancer, kidney cancer including renal cell carcinoma, liver cancer, lung cancer including small and non-small cell lung cancers, malignant peritoneal effusion, malignant pleural effusion, skin cancers including malignant melanoma, tumor progression of human skin keratinocytes, squamous cell carcinoma, basal cell carcinoma, and hemangiopericytoma, mesothelioma, Kaposi's sarcoma, bone cancer including osteomas and sarcomas such as fibrosarcoma and osteosarcoma, cancers of the female reproductive tract including uterine cancer, endometrial cancer, ovarian cancer, ovarian (germ cell) cancer and solid tumors in the ovarian follicle, vaginal cancer, cancer of the vulva, and cervical cancer; breast cancer (small cell and ductal), penile cancer, prostate cancer, retinoblastoma, testicular cancer, thyroid cancer, trophoblastic neoplasms, and Wilms' tumor.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any cancer derived from any organ system and any disease or disorder in which the CLL-1 antigen is implicated. As demonstrated in Example 3, CLL-1 is expressed in primary myeloid cells and AML cells. Leukemias may result from uncontrolled cell proliferation initially within the bone marrow before disseminating to the peripheral blood, spleen, lymph nodes and finally to other tissues. Immunotargeting CLL-1 may be used in treating malignancies involving myeloid cells including acute myelogenous leukemia and myelomas including but not limited to multiple myeloma, Burkitt's lymphoma, cutaneous B cell lymphoma, primary follicular cutaneous B cell lymphoma, B lineage acute lymphoblastic leukemia (ALL), B cell non-Hodgkin's lymphoma (NHL), B cell chronic lymphocytic leukemia (CLL), acute lymphoblastic leukemia, hairy cell leukemia (HCL), acute myelogenous leukemia, acute myelomonocytic leukemia, chronic myelogenous leukemia, lymphosarcoma cell leukemia, splenic marginal zone lymphoma, diffuse large B cell lymphoma, B cell large cell lymphoma, malignant lymphoma, prolymphocytic leukemia (PLL), lymphoplasma cytoid lymphoma, mantle cell lymphoma, mucosa-associated lymphoid tissue (MALT) lymphoma, primary thyroid lymphoma, intravascular malignant lymphomatosis, splenic lymphoma, Hodgkin's disease, and intragraft angiotropic large-cell lymphoma. Other diseases that may be treated by the methods of the present invention include multicentric Castleman's disease, primary amyloidosis, Franklin's disease, Seligmann's disease, primary effusion lymphoma, post-transplant lymphoproliferative disease (PTLD) [associated with EBV infection], paraneoplastic pemphigus, chronic lymphoproliferative disorders, X-linked lymphoproliferative syndrome (XLP), acquired angioedema, angioimmunoblastic lymphadenopathy with dysproteinemia, Herman's syndrome, post-splenectomy syndrome, congenital dyserythropoietic anemia type III, lymphoma-associated hemophagocytic syndrome (LAHS), necrotizing ulcerative stomatitis, Kikuchi's disease, lymphomatoid granulomatosis, Richter's syndrome, polycythemic vera (PV), Gaucher's disease, Gougerot-Sjogren syndrome, Kaposi's sarcoma, cerebral lymphoplasmocytic proliferation (Bind and Neel syndrome), X-linked lymphoproliferative disorders, pathogen associated disorders such as mononucleosis (Epstein Barr Virus), lymphoplasma cellular disorders, post-transplantational plasma cell dyscrasias, and Good's syndrome.

X. Articles of Manufacture

In another embodiment of the invention, an article of manufacture containing materials useful for the treating diseases or disorders implicating CLL-1 is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-CLL-1 antibody (e.g., 21.16 or 1075.7). The label or package insert indicates that the composition is used for treating leukemias or lymphomas, for example acute myeloid leukemia. Alternatively, or additionally, the article of manufacture may further comprise a second container comprising a pharmaceutically-acceptable buffer, such as bacteriostatic water for injection (BWFI), phosphate-buffered saline (PBS), Ringer's solution and dextrose solution. It may further include other materials desirable from a commercial and user standpoint, including other buffers, diluents, filters, needles and syringes.

Further details of the invention are illustrated by the following non-limiting Examples. The disclosures of all citations in the specification are expressly incorporated herein by reference.

EXAMPLE 1

Generation and Production of Recombinant CLL-1 Protein

A. Molecular Cloning of CLL-1

A human cDNA library was used as a template to amplify the extracellular domain of CLL-1 by PCR. The resulting fragment with the following sequence was cloned into pIntron.IgKsigP at NheI/NotI restriction sites:

```
                                        (SEQ ID NO: 12)
ATAGAAATGAAAAAAATGAACAAACTACAAAACATCAGTGAAGAGCTC

CAGAGAAATATTTCTCTACAACTGATGAGTAACATGAATATCTCCAAC

AAGATCAGGAACCTCTCCACCACACTGCAAACAATAGCCACCAAATTA

TGTCGTGAGCTATATAGCAAAGAACAAGAGCACAAATGTAAGCCTTGT

CCAAGGAGATGGATTTGGCATAAGGACAGCTGTTATTTCCTAAGTGAT

GATGTCCAAACATGGCAGGAGAGTAAAATGGCCTGTGCTGCTCAGAAT

GCCAGCCTGTTGAAGATAAACAACAAAAATGCATTGGAATTTATAAAA

TCCCAGAGTAGATCATATGACTATTGGCTGGGATTATCTCCTGAAGAA

GATTCCACTCGTGGTATGAGAGTGGATAATATAATCAACTCCTCTGCC

TGGGTTATAAGAAACGCACCTGACTTAAATAACATGTATTGTGGATAT
```

-continued

ATAAATAGACTATATGTTCAATATTATCACTGCACTTATAAACAAAGA

ATGATATGTGAGAAGATGGCCAATCCAGTGCAGCTTGGTTCTACATAT

TTTAGGGAGGCA.

B. Recombinant Protein Production $3\times10^6$ HEK-293 cells (ATCC) were plated in a 100 mm cell culture plate in 10 mL of DMEM+10% FBS+Pen/Strep+L-Glutamine. After 24 hours, the cells were transfected with 15 µg of a plasmid construct containing the sequence of the CLL-1 extracellular domain (SEQ ID NO: 3) fused to a C-terminal tag of V5-His using FuGene6 transfection reagent (Roche). 48 hours post-transfection, the medium was changed to 10 mL of DMEM+10% FBS+Pen/Strep+L-Glutamine containing 1.0 mg/ml G418. The G418-resistant cells were selected for 2 weeks with selection medium changed every 2-3 days. The stable cells were further subjected to clonal selection for 3-4 weeks. Clonal cell lines expressing CLL-1-ECD-V5His recombinant protein were screened with both HisSord-based ELISA (Qiagen) and Western blot analysis detected with anti-V5 monoclonal antibody (Invitrogen). Stable clones with the highest protein expression levels were selected and expanded. The selected clone(s) was further subjected to suspension- and serum-deficient adaptation for 3-4 weeks and the recombinant protein expression was monitored with Western blot analysis. Production of the recombinant protein was performed with 1 L spinners. About 50 L of conditional medium (2-4 mg/L) were harvested and subjected to protein purification process.

C. Purification of CLL-1 V5-6His Protein from HEK293 Cells

18 L culture supernatant from stably transfected HEK293 cells containing recombinant CLL-1-ECD-V5His were supplemented with 1 mM EDTA and 0.4 mM Pefbloc (Roche) protease inhibitors and filtered through a 0.22 µm filter. The supernatant was 10-fold concentrated and diafiltered with 20 mM sodium phosphate, 0.5 M NaCl, pH 7 buffer using a Tangential flow filtration (TFF) system with 10 kDa cut-off membrane (Pall Filtron). The diafiltered medium was loaded on a 5 mL Ni-chelating affinity column (GE Healthcare) which was then washed with 20 mM imidazole and eluted with a gradient of 20 nM to 220 nM imidazole. Fractions containing CLL-1 were pooled and buffer exchanged to PBS buffer resulting in a final yield of 10 mg protein with 97% purity.

EXAMPLE 2

Generation and Characterization of Anti-CLL-1 Monoclonal Antibodies

A. Generation of Hybridomas

Recombinant CLL-1 protein containing the complete extracellular domain was produced as described in Example 1. Using standard protocols (see Kohler and Milstein, *Nature* 256:495-497 (1975) herein incorporated by reference in its entirety), immunizations of Balb/c mice with the extracellular domain of CLL-1 (SEQ ID NO: 3) and subsequent fusions with SP20-Ag14 cells (ATCC) resulted in a total of ~5400 hybridoma supernatants containing antibodies which bound to CLL-1 in an ELISA screen, 275 of which scored positive by FACS analysis on HL-60 cells. Briefly, $2\times10^5$ cells were resuspended at $5\times10^6$ cells/ml in blocking buffer (10% heat-inactivated human serum, BioWhittaker #14-402E in PBS) and 100 µl were added to each well of a round-bottom 96-well plates and incubated for 15 minutes on ice. 100 µl of hybridoma supernatant were added to each well and plates were incubated for an additional 20 minutes on ice. Cells were centrifuged for 5 minutes at 1500 rpm, supernatant was removed and cells were washed twice in cold FACS buffer (1% BSA in PBS). The pellet was resuspended in 100 µl blocking buffer containing 0.25 µg of secondary antibody (goat anti-mouse PE conjugated, BD Pharmingen #550589) and incubated for 15 minutes on ice. Cells were analyzed for fluorescence in FL-2 using an Automated Microsampler from Cytek hooked up to a FACScalibur (Becton Dickinson).

Based on isotype and relative affinity, two hits were subcloned, re-screened, selected for scale-up and purified using a protein G column. Initial analysis of complement-mediated cytotoxicity on B cell lines revealed two lead murine monoclonal antibodies with potent efficacy in vitro which were subsequently used in detailed expression analysis and efficacy studies and to generate chimeric monoclonal antibodies (discussed below).

B. ELISA Screen of Hybridoma Supernatants for Binding to CLL-1

Antigen was coated at 1 µg/ml in Carbonate-Bicarbonate buffer (Sigma #C-3041) on MaxiSorp 96-well plates (Nunc) and incubated overnight at 4° C. After three washes with 300 µg/well TBST (0.1 M Tris-HCl, 0.15 M NaCl, 0.05% Tween-20), wells were blocked using 300 µg/well 2% BSA (Sigma #A9647) in PBS for one hour at room temperature. Hybridoma supernatants were diluted 1:2 in Iscove's Media (Gibco #31980-030) with 10% FBS (Gibco #20012-027) and 100 µl were added to each well followed by incubation for 2 hours on a plate shaker at room temperature. Three washes with TBST were followed by addition of 100 µl of secondary antibody, goat anti-mouse Ig-HRP (BioRad #170-6516), diluted 1:10,000 in 0.5% BSA/PBS and incubation for one hour on a plate shaker. After five washes with TBST, 100 µl TMB substrate (KPL #50-76-03) were added and color was allowed to develop for 10 minutes. Plates were read at 450 nm on a SpectraMax plate reader (Molecular Devices).

C. Generation of anti-CLL-1 Chimeric Monoclonal Antibodies

Chimeric mAbs against CLL-1 were generated as follows: RNA was isolated from hybridoma fusion cells expressing the anti-CLL-1 mAb of interest. Using standard RACE/RT-PCR techniques, the heavy and light variable regions were cloned into two separate expression vectors in fusion with cDNA encoding for human $IgG_1$ constant regions. The resulting plasmids were co-transfected into CHO cells and stable cell lines were selected secreting full-length chimeric mAbs. Conditioned medium of these cell lines was subjected to protein G purification to yield purified chimeric mAbs. Initial analysis revealed two lead chimeric mAbs: 21.16 and 1075.7, both of which were $IgG_1$ and were subsequently used in detailed expression analysis and efficacy studies (discussed below).

EXAMPLE 3

Expression In Primary Cells and Cancer Lines

Figure 1D:
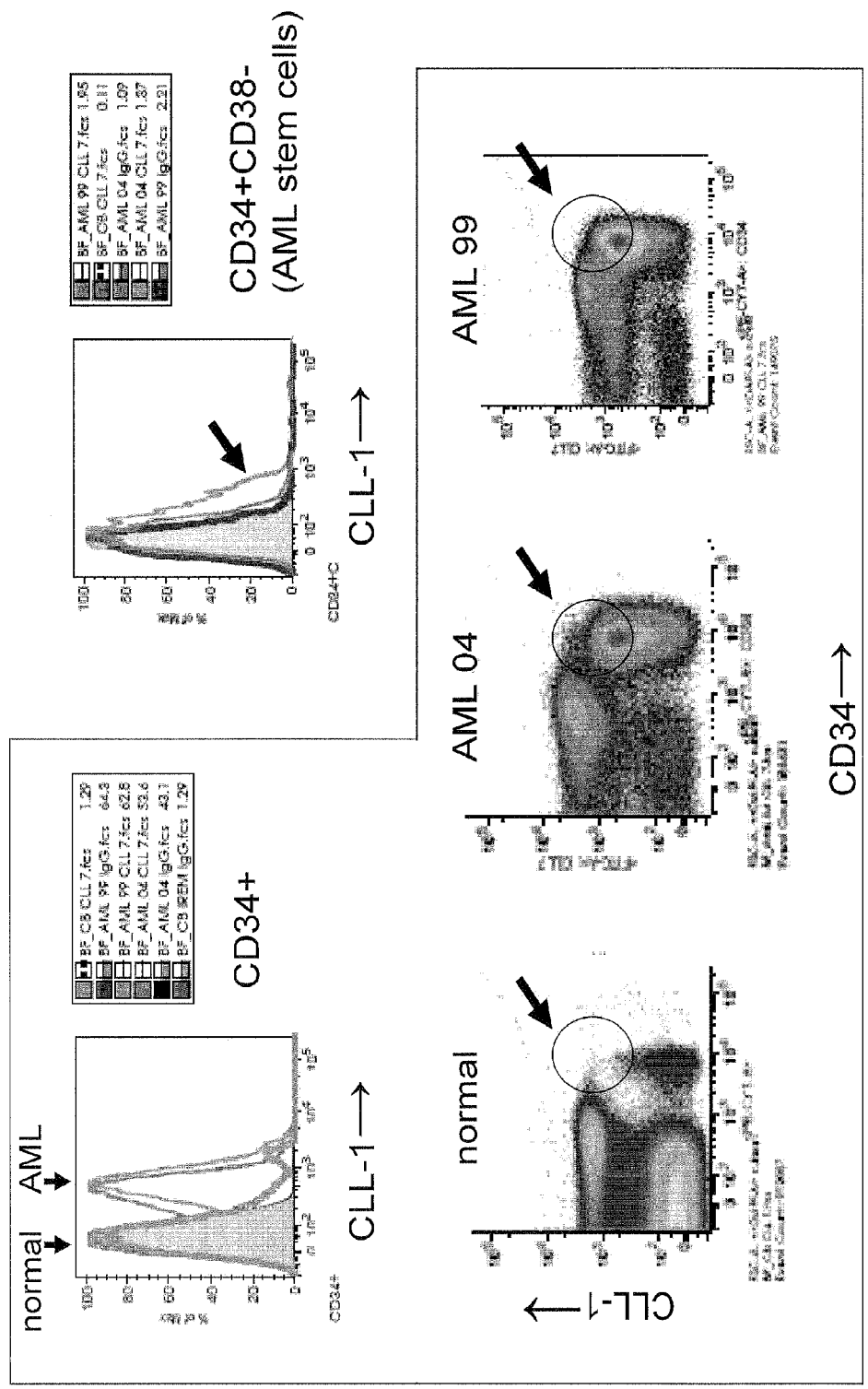
FIG. 1D: Expression of CLL-1 in AML stem cells and normal stem cells.

Fluorescein (FITC)-labeled mAb 21.16 was used to analyze expression of CLL-1 normal and leukemia cells. Normal human peripheral blood cells were assayed for CLL-1 expression by flow cytometry as described above (FIG. 1A). Markers for normal monocytes, granulocytes, platelets and dendritic cells were used to identify the various cell populations as indicated. The analysis confirmed previously reported expression on monocytes and granulocytes (Bakker et al, *Cancer Res.* 64:8443-8450 (2004); Marshall et al, *J. Biol. Chem.* 279:14792-14802 (2004)). CLL-1 was also found on mature and precursor dendritic cells indicating that CLL-1 is expressed in myeloid, but not lymphoid, cells. Similar results were found in normal bone marrow (not shown). In addition, leukemia cell lines representing various stages of AML (FAB classification) were analyzed and found to express relatively high levels of CLL-1 (FIG. 1B). Interestingly, CLL-1 expression was found in AML blasts and CD34+/CD38− AML stem cells (FIG. 1C), but not in normal stem cells (FIG. 1D). CLL-1 expression was also assayed in blast cells obtained from AML patients and was found to be expressed in most cases (see Table 4).

TABLE 4

| Number of Cases | Percent CLL-1 Positive |
|---|---|
| 8 AML without maturation | 38% |
| 7 AML with maturation | 86% |
| 5 acute myelomonocytic leukemia | 100% |
| 13 acute monocytic leukemia | 100% |
| 4 AML with multilineage dysplasia | 100% |
| 2 AML with inv(16)(p13q22) | 50% |
| 1 AML with 11q23 abnormality | 100% |
| 1 persistent AML | 100% |
| 1 AML from CMPD | 0% |
| 4 unclassified | 75% |
| Total: 45 cases | 80% |

In an immunohistochemistry and tissue microarray experiment, analysis of normal tissues revealed expression of CLL-1 in spleen and lung with macrophage infiltration, all other normal tissues were negative (see Table 5). In AML patient samples, CLL-1 expression was observed in all but one case (see Table 6).

TABLE 5

| Tissue | Anti-CLL-1 mAb | Negative Control |
|---|---|---|
| Heart | Negative (5/5 case) | Negative (5/5 case) |
| Liver | Negative (5/5) | Negative (5/5) |
| Colon | Negative (5/5) | Negative (5/5) |
| Breast | Negative (5/5) | Negative (5/5) |
| Kidney | Negative (unspecific background) | Negative (5/5) |
| Brain | Negative (5/5) | Negative (5/5) |
| Lung | "+" with macrophate | Negative (5/5) |
| Uterus | Negative (5/5) | Negative (5/5) |
| Small intestine | Negative (unspecific background) | Negative (5/5) |
| Skin | Negative (5/5) | Negative (5/5) |
| Prostate | Negative (5/5) | Negative (5/5) |
| Pancreas | Negative (5/5) | Negative (5/5) |
| Ovary | Negative (5/5) | Negative (5/5) |
| Tonsil | Negative (5/5) | Negative (5/5) |
| Bladder | Negative (5/5) | Negative (5/5) |
| Testis | Negative (5/5) | Negative (5/5) |
| Stomach | Negative (5/5) | Negative (5/5) |
| Spleen | "+" with splenic lining cells | Negative (5/5) |

TABLE 6

| Diagnosis | % positive case | % of blasts in bone marrow aspirate | Anti-CLL-1 mAb staining* |
|---|---|---|---|
| AML persistent | 100 (3/3) | 7-48 | 4+ (2); 3+ (1) |
| AML favor AMML | 100 (1/1) | 80 | 4+ |
| AML (FAB-M0 or M1) | 100 (4/4) | 77-95 | 4+ (3); 3+ (1) |
| AML (FAB-M2 | 100 (14/14) | 35-64 | 4+ (13); 2+ (1) |
| AML (FAB-M4) | 100 (4/4) | 22-74 | 4+ |
| AML (FAB-M4eo) | 0 (0/1) | 43 | Neg. |
| AML (FAB-M5) | 100 (2/2) | 89, 90 | 4+ |
| MAL (FAB-M6) | 100 (1/1) | 26 | 1+ |
| Unclassified | 100 (8/8) | 38-89 | 4+ (6); 3+ (2) |
| Total: 38 cases | 97.3 (37/38) | | |

*"1+" = 10-25%; "2+" = 25-50%; "3+" = 50-75%; "4+" > 75% positive of blasts

EXAMPLE 4

Affinity Measurements for mAbs 21.16 and 1075.7

Kinetic rate constants ($k_a$ and $k_d$) were determined using surface plasmon resonance and affinities ($K_D$) were then calculated from the rate constants ($k_d/k_a$). Surface plasmon resonance was carried out on a BIAcore system (Biacore International AB, Uppsala, Sweden). Chimeric monoclonal antibodies (21.16 or 1075.7) were diluted to 2 μg/ml and then captured on the biosensor surface using an anti-mouse mAb. Antigen was diluted to a starting concentration of 46 nM and tested for binding to the mAb samples using a 3-fold dilution series. Each of 5 concentrations was tested twice except the highest concentration which was tested 5 times in total, two times with a short dissociation of 300 seconds followed by three times with a dissociation of 60 minutes. The data sets from the long dissociation experiments were globally fit with the shorter association experiments to determine binding constants for the interactions. The analysis was carried out in HBS, pH 7.4 buffer at 25° C. (Canziani et al, *Anal. Biochem.* 352:301-307 (2004)). The $k_a$, $k_d$, and $K_D$ values for 21.16 and 1075.7 are listed in Table 7 below.

TABLE 7

| mAb | $k_a (M^{-1}s^{-1})$ | $k_d (s^{-1})$ | $K_D (M)$ |
|---|---|---|---|
| 21.16 | 5.54(4)e5 | 0.00845(8) | $1.53 \times 10^{-9}$ |
| 1075.7 | 4.17(1)e5 | 1.5(2)e−4 | $0.36 \times 10^{-9}$ |

EXAMPLE 5

Cytotoxic Activity of Anti-CLL-1 Antibodies

Complement-dependent cytotoxicity (CDC) assays were performed using mAbs 21.16 and 1075.7 on a variety of immune cell lines. Human acute myeloid leukemia cell line HL-60 was obtained from ATCC. HL-60 cells were cultured in RPMI 1640 (Gibco #61870), 20% fetal bovine serum (Gibco #26140-079) and 1% Pen/Strep (Gibco #15070-063). 283 cells (parental and stable transfectants expressing CLL-1) were cultured in DMEM, 10% fetal bovine serum and 1% penstrep (37° C.; 5% $CO_2$).

Using cells at log phase of growth, 100,000 cells/well were plated in a 96 well plate, in 50 μl complete media (CM: RPMI 1640 (or DMEM), 10% fetal bovine serum and 1% Pen/Strep). 50 μl of 2× antibody/$IgG_2b$ isotype, made up in CM, were added to each well and the plates were left at room temperature for 20 minutes. 2-10 μl of freshly prepared baby rabbit complement (Cedarlane labs #CL3441) were added to respective wells, and plates placed in the incubator for 1 hr. After equilibrating plates to RT, viability was measured using CELLTITER-GLO™ (Promega #G7571). 100 μl of CELL-TITER-GLO™ reagent were added to each well and luminescence was measured on a VERITAS™ microplate luminometer (Turner Biosystems, Sunnyvale, Calif., USA). Data was normalized to complement+isotype.

Figure 2A:
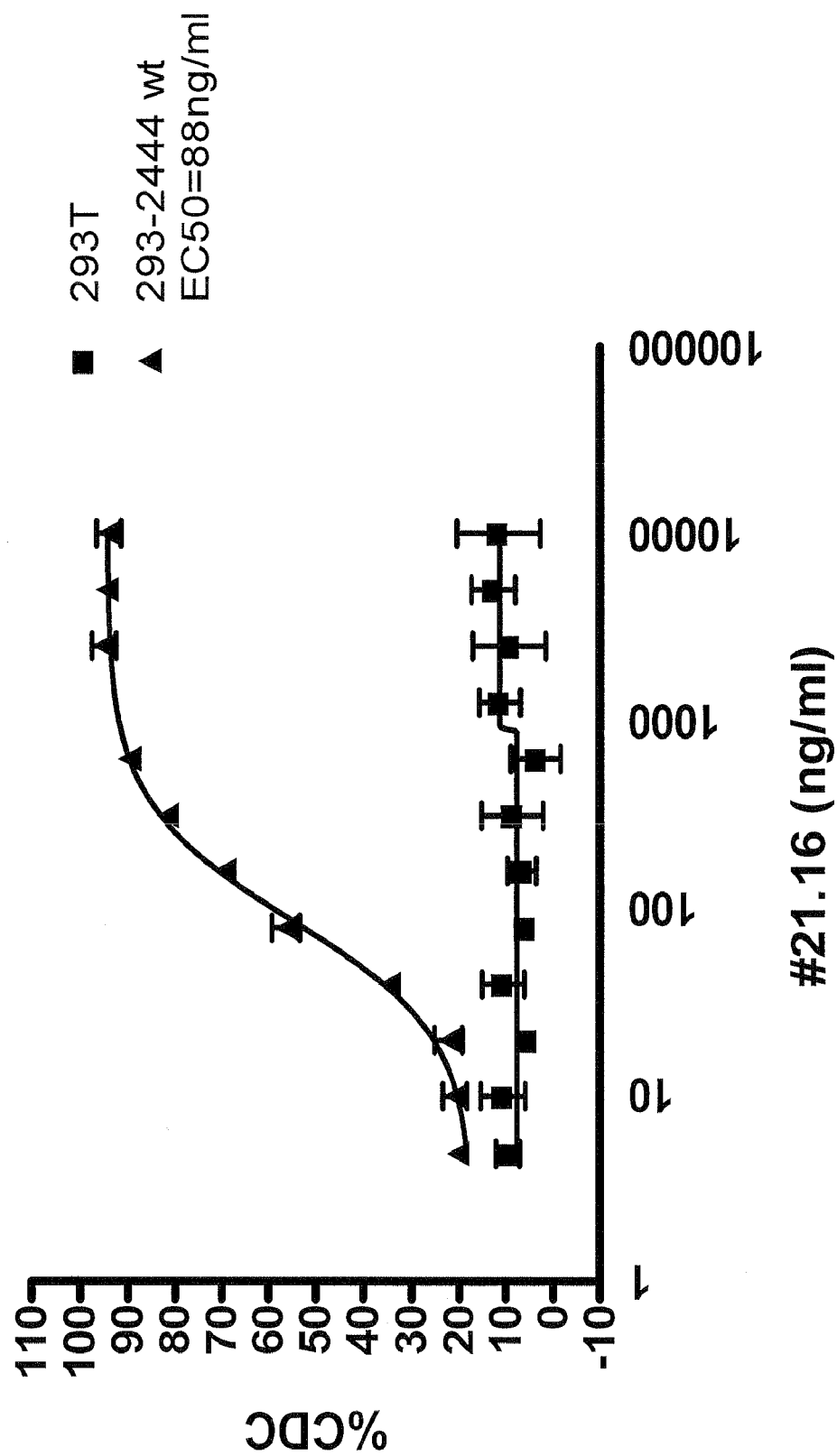
FIG. 2A: CDC analysis of 21.16 mAb in parental HEK293 cells (squares) and HEK293 cells stably transfected with CLL-1 (triangles).

Assays were performed to determine whether the cytotoxic activity mediated by anti-CLL-1 mAbs was dependent on the presence of CLL-1 on the cell membrane. HEK293 (human embryonic kidney) cells were stably transfected with CLL-1 and CDC dose-response assays were carried out on these transfectants as well as on the parental line. Incubation of HEK293 cells expressing CLL-1 with varying concentrations of mAb 21.16 in the presence of complement led to potent cytotoxic activity with an $EC_{50}$ of around 88 ng/ml. Parental HEK293 cells appeared to be resistant, whereas HEK293 +CLL-1 cells were sensitive to anti-CLL-1-induced CDC (FIG. 2A). These results confirm specificity of anti-CLL-1 mAbs: expression of CLL-1 is necessary for the induction of CDC activity.

Figure 2B:
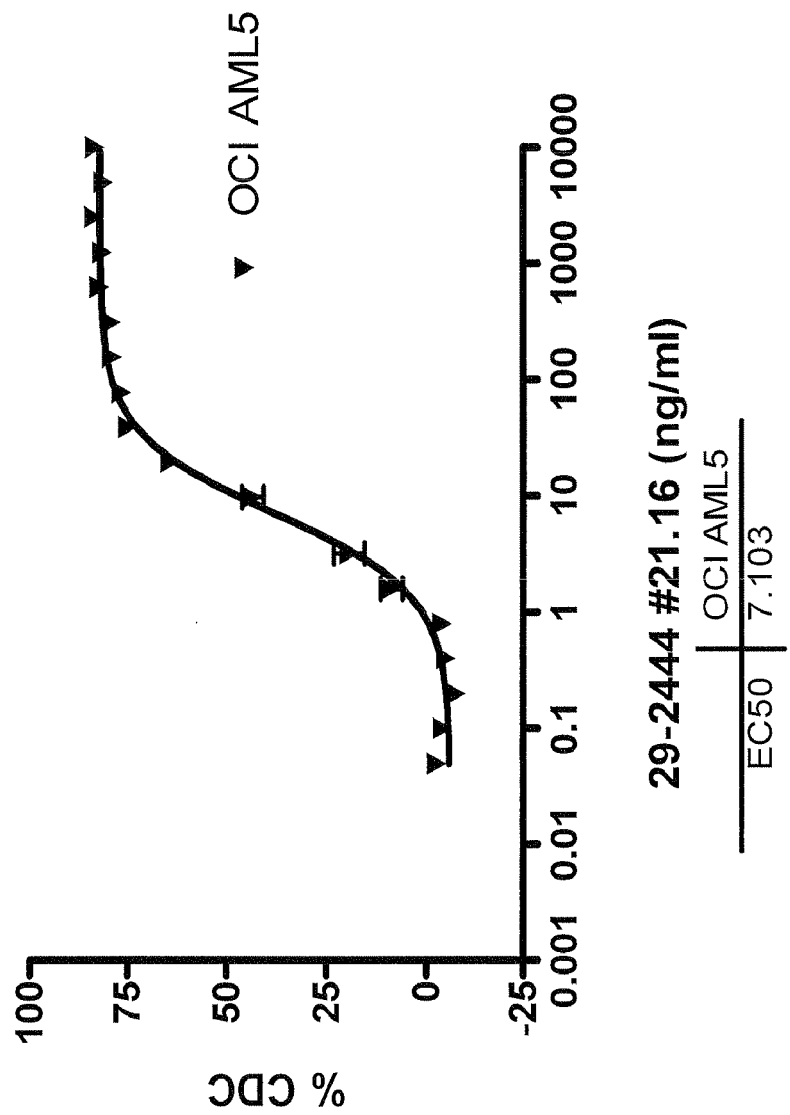
FIG. 2B: CDC analysis of 21.16 mAb in OCI-AML5 cells.
Figure 2C:
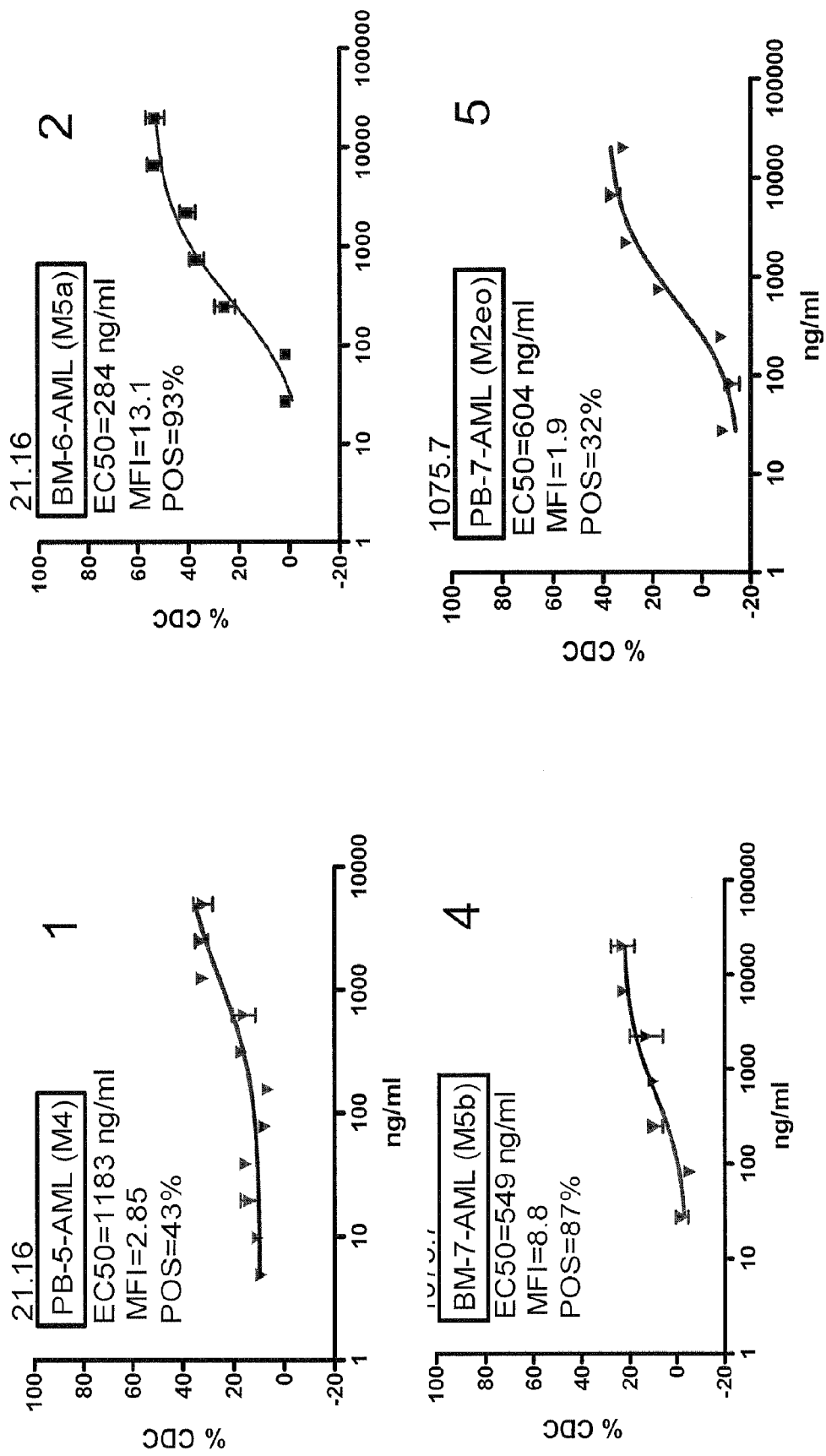
FIG. 2C: CDC analysis of 21.16 mAb and 1075.7 mAb in AML patient samples.

Incubation of another AML cell line, OCI AML5, with varying concentrations of mAb 21.16 in the presence of complement led to potent cytotoxic activity with an $EC_{50}$ of around 7.1 ng/ml (FIG. 2B). An isotype control antibody displayed no CDC activity (not shown). CDC assays were also performed on cancer target cells from AML patients. Cytotoxicity was observed in a dose-dependent manner in all AML-derived samples tested, with $EC_{50}$s in the range of from about 2 µg/ml to about 12 µg/ml (FIG. 2C).

Figure 2D:
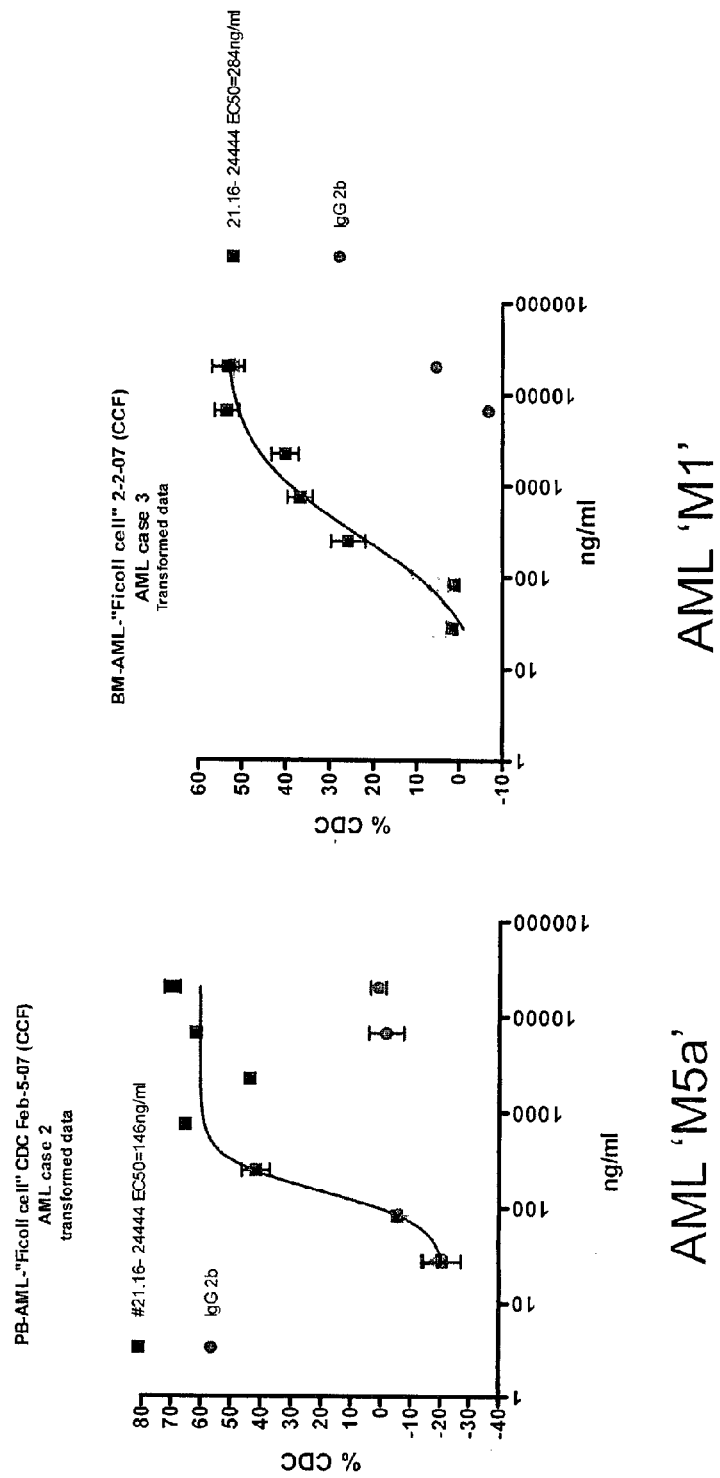
FIG. 2D: Ex vivo cytotoxicity assay in acute myelogenous leukemia (AML, stage M1 and M5a, FAB classification) patient samples using 21.16 mAb (square=21.16 mAb; circle=isotype control).

Ex vivo cytotoxicity assays were also performed using mAb 21.16 on two patient AML samples (FAB stage M1 and M5a). Samples were prepared as described above. Again, cytotoxicity was observed in a dose-dependent manner with an $EC_{50}$ of 146 ng/ml for AML "M5a" and an $EC_{50}$ of 284 ng/ml for AML "M1" (FIG. 2D).

ADCC assays are performed using the anti-CLL-1 mAbs. Human NK cells are isolated from buffy coat by negative selection using Rosette Sep NK cell enrichment cocktail from Stem Cell Technologies (Vancouver, BC, Canada), according to manufacturer's instructions. Mouse splenocytes are isolated as described in Coleman et al. (*J. Immunother.* 29:489-498 (2006)). Specific lysis of target cells is determined by using a standard 4 hr $^{51}Cr$ release assay in a 96 well plate format as previously described (Coleman et al., 2006, supra). No pre-incubation step of effector cells and antibody is performed. Percent lysis is calculated using the following standard equation: ((TEST−BGD)/(Max−BGD))×100 where TEST is sample release, BGD is spontaneous release and Max is Triton-X mediated release. Percent specific lysis has effector control subtracted.

EXAMPLE 6

In Vivo Anti-Tumor Activity of Anti-CLL-1 Antibodies

A. Leukemia Xenograft Model in Immunodeficient Mice

The xenograft HL-60 model was carried out as described in Naumovski et al (Mol. Cancer Ther. 4:968-976 (2005)). Young adult female SCID mice at age of 6-8 weeks were used (Charles River Laboratory). Each mouse was subcutaneously inoculated with $1 \times 10^7$ leukemia cells in a volume of 100 µl on the rear back of the mouse. Xenografts were allowed to establish to an average size of 50-100 $mm^3$ after which xenograft-bearing mice were randomized into various conditional groups as follows (10 mice/group):

1. Saline control
2. Isotype control (human IgG1) (0.5 mg/mouse)
3. Chimeric CLL-1 mAb (clone #1075.7) (5 mg/kg)
4. Chimeric CLL-1 mAb (clone #1075.7) 0.5 mg/kg)

Figure 3:
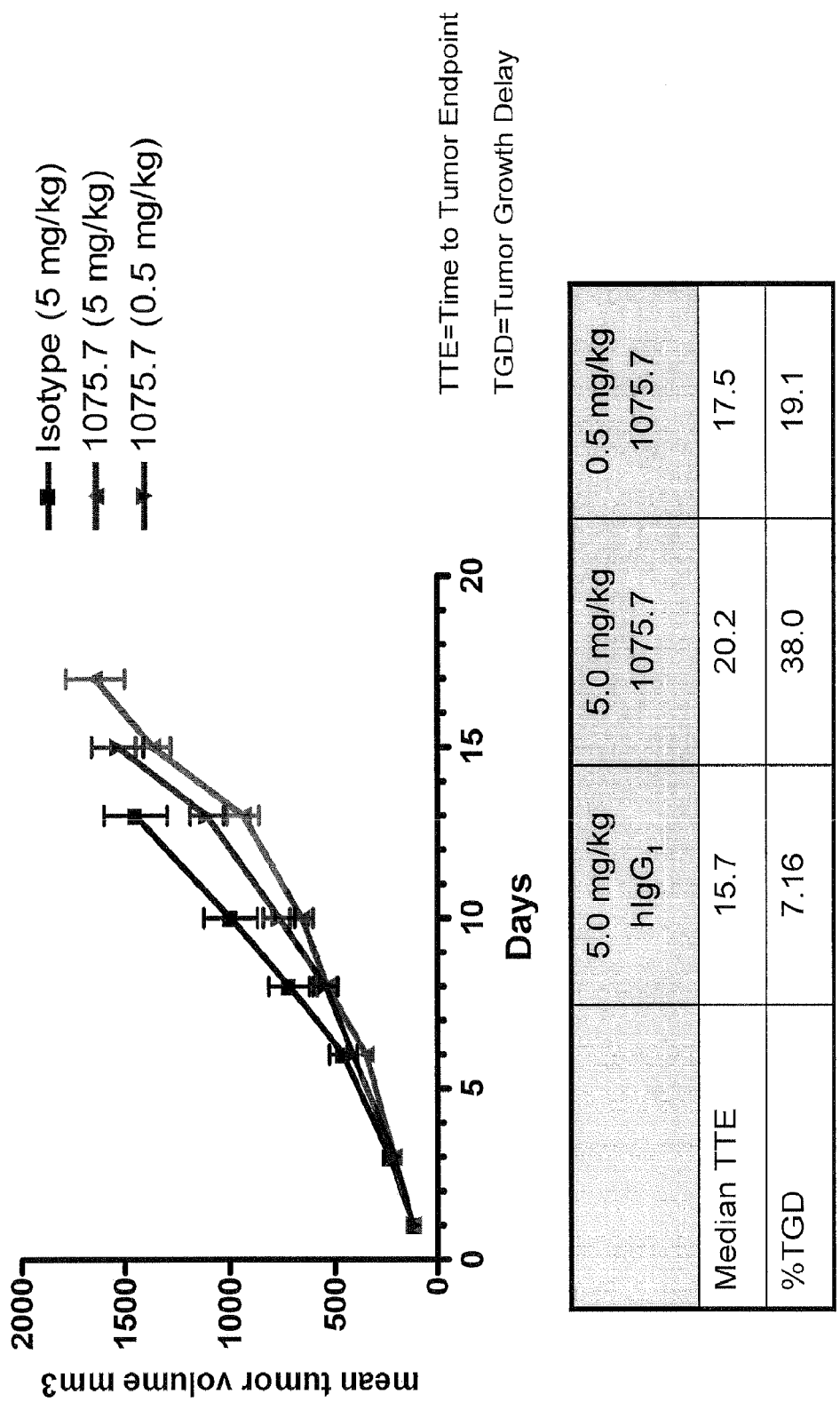
FIG. 3: Anti-tumor activity of anti-CLL-1 chimeric mAb 1075.7 in the HL-60 xenograft model.

Anti-CLL-1 mAbs were given to each mouse at the designated dose via intraperitoneal (ip) injection at frequency of twice a week. Each mouse was measured for tumor size using a caliper on alternate days. Animal body weight and any sign of morbidity were also closely monitored. The anti-CLL-1 mAb treatment lasted for two weeks at which point mice were harvested, tumor xenografts were extirpated, weighed, and correlated with the tumor size measurement. As can be seen in FIG. 3, the anti-CLL-1 mAb delayed tumor growth.

B. Disseminated Model

The efficacy of anti-CLL-1 mAbs are further examined in a disseminating model (such as that described in Perentesis et al, *Clin. Cancer Res.* 3:2217-2227 (1997)). HL-60 cells, or other suitable human leukemia cells, are maintained in Iscove's modified Dulbecco's medium supplemented with 10% fetal bovine serum, 50 U/ml penicillin and 50 µg/ml streptomycin according to the manufacturer's suggestion. Leukemia cells are harvested at log growth phase. Harvested leukemia cells are confirmed of high viability (>95%) and resuspended into a buffer such as HBSS or PBS.

Young adult female SCID mice at age of 6-8 weeks are used (Charles River Laboratory). One day following sublethal total body irradiation with 2 Gy, each mouse receives an intraperitoneal (ip) injection of $4 \times 10^6$ HL-60 cells. Administration of anti-CLL-1 mAb starts 24 h after leukemia cell inoculation. Anti-CLL-1 mAb is given to each mouse at designated dose via intraperitoneal injection at frequency of twice a week, and the anti-CLL-1 treatment lasts for two weeks. Mice with disseminated leukemia cells are monitored daily signs of toxicity and survival. All mice are euthanized after 6 months; however, those mice exhibiting hind limb paralysis or those that are moribund are euthanized by $CO_2$ asphyxiation according to the Institutional Animal Care and Use Committee (IACUC) regulations.

EXAMPLE 7

Internalization of Anti-CLL-1 Antibodies

Figure 4:
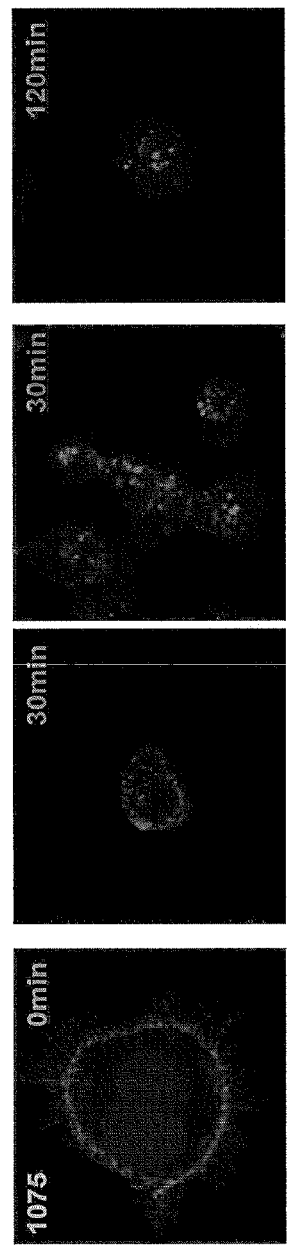
FIG. 4: Internalization of anti-CLL-1 mAb 1075.7 in transfected 293 cells.

HEK293 cells that stably expressed CLL-1 were grown on coverslips and incubated with Alexa488-conjugated anti-CLL-1 antibodies on ice. After three washes with PBS/BSA, cells were incubated at 37° C. for various periods of time (eg. 0, 30, 120 min) and fixed in PBS/4% PFA. After mounting in Vectashield (Vector Laboratories, Burlingame, Calif.), the slides were analyzed on a fluorescence microscope. As can be seen in FIG. 4, the anti-CLL-1 antibodies are internalized within 30 minutes of treatment.

Toxin conjugated anti-CLL-1 antibodies are analyzed for internalization using the aforementioned method. Toxin conjugated anti-CLL-1 antibodies are also assayed for cytotoxicity as described in Example 6.

We claim:

1. An isolated antibody or antigen-binding fragment thereof, comprising:
   a) a heavy chain comprising a first variable region comprising CDR1 (amino acids 49 to 58), CDR2 (amino acids 73 to 89), and CDR3 (amino acids 122 to 132) from SEQ ID NO: 5; and
   b) a light chain comprising a second variable region comprising CDR1 (amino acids 47 to 56), CDR2 (amino acids 72 to 78), and CDR3 (amino acids 111 to 120) from SEQ ID NO: 7,
   wherein the antibody binds CLL-1 with high affinity.

2. The isolated antibody or antigen-binding fragment thereof of claim 1, wherein:
   a) the heavy chain, comprising a first variable region, comprises a sequence that has at least 99% identity to the amino acid sequence as set forth in SEQ ID NO: 5; and
   b) the light chain, comprising a second variable region, comprises a sequence that has at least 99% identity to the amino acid sequence as set forth in SEQ ID NO: 7,
   wherein the antibody binds to CLL-1 with high affinity.

3. The antibody of claim 1, wherein the heavy chain and the light chain are connected by a flexible linker to form a single chain antibody.

4. The antibody of claim 3, which is a single-Fv antibody.

5. The antibody of claim 1, which is selected from the group consisting of an Fab antibody, an Fab' antibody, an (Fab')$_2$ antibody, a humanized antibody, and a chimeric antibody.

6. A pharmaceutical composition comprising the antibody of claim 1, further comprising a suitable carrier.

7. An isolated cell line that produces an antibody according to claim 1.

8. The antibody of claim 1, wherein said antibody is a humanized form thereof.

9. The antibody of claim 1, wherein said antibody is conjugated to a cytotoxic molecule.

10. The antibody of claim 9, wherein said cytotoxic molecule is selected from the group consisting of a radioisotope, a toxin, a chemotherapeutic agent, a drug, and a growth inhibitory agent.

* * * * *